United States Patent
Poitout et al.

(10) Patent No.: US 8,227,485 B2
(45) Date of Patent: Jul. 24, 2012

(54) BENZIMIDAZOLE AND IMIDAZOPYRIDINE DERIVATIVES AND USE THEREOF AS A MEDICAMENT

(75) Inventors: Lydie Poitout, Le Kremlin Bicetre (FR); Valerie Brault, Saint-Arnoult-en Yvelines (FR); Carole Sackur, Paris (FR); Pierre Roubert, Paris (FR); Pascale Plas, Chatillon (FR)

(73) Assignee: Ipsen Pharma S.A.S., Paris (FR)

( * ) Notice: Subject to any disclaimer, the term of this patent is extended or adjusted under 35 U.S.C. 154(b) by 1370 days.

(21) Appl. No.: 11/441,116

(22) Filed: May 26, 2006

(65) Prior Publication Data

US 2006/0281784 A1 Dec. 14, 2006

Related U.S. Application Data

(63) Continuation of application No. PCT/FR2004/003007, filed on Nov. 24, 2004.

(30) Foreign Application Priority Data

Nov. 28, 2003 (FR) ..................... 03 13988

(51) Int. Cl.
*A61K 31/4745* (2006.01)
*C07D 403/02* (2006.01)

(52) U.S. Cl. ........ 514/303; 514/322; 514/338; 514/394; 546/117; 546/199; 546/273.1; 546/305.1; 546/307.4

(58) Field of Classification Search .................. 514/303, 514/322, 338, 394; 546/117, 199, 273.1; 548/305.1, 307.4

See application file for complete search history.

(56) References Cited

U.S. PATENT DOCUMENTS

| | | | | |
|---|---|---|---|---|
| 5,011,838 A | * | 4/1991 | Roberto et al. | 514/234.2 |
| 6,696,437 B1 | * | 2/2004 | Lubisch et al. | 514/217.09 |
| 6,825,219 B2 | * | 11/2004 | Cywin et al. | 514/338 |
| 7,355,052 B2 | * | 4/2008 | Poitout et al. | 548/307.4 |
| 7,495,009 B2 | * | 2/2009 | Poitout et al. | 514/303 |
| 7,495,110 B2 | * | 2/2009 | Poitout et al. | 548/307.1 |
| 7,501,524 B2 | * | 3/2009 | Poitout et al. | 548/307.4 |
| 7,501,525 B2 | * | 3/2009 | Poitout et al. | 548/307.4 |
| 7,550,603 B2 | * | 6/2009 | Zhu et al. | 548/304.7 |

FOREIGN PATENT DOCUMENTS

| | | | |
|---|---|---|---|
| WO | WO 01/10842 | | 2/2001 |
| WO | WO 02/092575 | | 11/2002 |
| WO | WO 03/041708 | * | 5/2003 |
| WO | WO 03/053939 | * | 7/2003 |

OTHER PUBLICATIONS

Poitout et al. "Identification of a novel series . . . " Bioorg. Med. Chem. Lett. v.17, p. 4464-4470 (2007).*
"bioisosters . . . " Med. Chem. Principle and Practice p. 206-209 (1994).*
Patani et al. "Bioisosterism . . . " Chem. Rev. v.96, p. 3147-3176 (1996).*
Rubini et al. "Synthesis of isosteric . . . " Tetrahedrom. v. 42, p. 6039-45 (1996).*
Lima et al. "Bioisosterism: a useful strategy . . . " Current Med. Chem. v.12, p. 23-49 (2005).*
Wikipedia "lead compound" (2010).*

* cited by examiner

*Primary Examiner* — Celia Chang
(74) *Attorney, Agent, or Firm* — Hunton & Williams LLP

(57) ABSTRACT

The invention relates to novel benzimidazole and imidazopyridine derivatives having general formula (I), which have a good affinity with certain sub-types of melanocortin receptors, particularly MC4 receptors. Said derivatives are particularly suitable for the treatment of pathological states and diseases involving one or more melanocortin receptors. The invention also relates to pharmaceutical compositions containing said products.

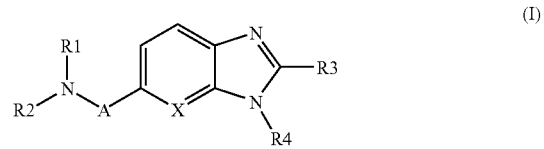

(I)

17 Claims, No Drawings

BENZIMIDAZOLE AND IMIDAZOPYRIDINE DERIVATIVES AND USE THEREOF AS A MEDICAMENT

CROSS REFERENCE TO RELATED APPLICATION

This application is a continuation of PCT/FR2004/003007, filed on Nov. 24, 2004, which in turn claims priority FR 0313988 filed on Nov. 28, 2003.

FIELD OF INVENTION

A subject of the present application is novel benzimidazole and imidazo-pyridine derivatives. These products have a good affinity for certain melanocortin receptor subtypes, in particular MC4 receptors. They are particularly useful for treating pathological states and diseases in which one or more melanocortin receptors are involved. The invention also relates to pharmaceutical compositions containing said products and their use for the preparation of a medicament.

BACKGROUND OF INVENTION

The melanocortins represent a group of peptides which derive from the same precursor, proopiomelanocortin (POMC), and which are structurally similar: adrenocorticotropic hormone (ACTH), α-melanocyte-stimulating hormone (α-MSH), β-MSH and γ-MSH (Eipper B. A. and Mains R. E., *Endocr. Rev.* 1980, 1, 1-27). The melanocortins perform numerous physiological functions. They stimulate the synthesis of steroids by the adrenal cortex and the synthesis of eumelanin by the melanocytes. They regulate food intake, energy metabolism, sexual function, neuronal regeneration, blood pressure and heart rate, as well as pain perception, learning, attention and memory. The melanocortins also possess anti-inflammatory and anti-pyretic properties and control the secretion of several endocrine or exocrine glands such as the sebaceous, lachrymal, mammary glands, the prostate and the pancreas (Wikberg J. E. et al. *Pharmacol. Res.* 2000, 42, 393-420; Abdel-Malek Z. A., *Cell. Mol. Life. Sci.* 2001, 58, 434-441).

The effects of the melanocortins are mediated by a family of membrane receptors specific to seven transmembrane domains and G-protein-coupled. Five receptor subtypes, named MC1 to MC5, have been cloned and characterized to date. These receptors differ in their tissue distribution and affinity for the different melanocortins, the MC2 receptors recognizing only ACTH. The stimulation of the melanocortin receptors activates the adenylate cyclase with production of cyclic AMP. If the functional roles specific to each of the receptors are not totally elucidated, the treatment of pathological disorders or diseases can be associated with an affinity for certain subtypes of receptors. Thus the activation of the MC1 receptors has been associated with the treatment of inflammations, whereas blocking them has been associated with the treatment of cutaneous cancers. The treatment of nutritional disorders has been associated with the MC3 and MC4 receptors, the treatment of obesity by the agonists and the treatment of cachexia and anorexia by the antagonists. Other indications associated with the activation of the MC3 and MC4 receptors are sexual activity disorders, neuropathic pain, anxiety, depression and drug addition. The activation of the MC5 receptors has been associated with the treatment of acne and dermatitis.

BRIEF SUMMARY OF THE INVENTION

The applicants have found that the new compounds of general formula (I) described hereafter possess a good affinity for the melanocortin receptors. They act preferentially on the MC4 receptors. Said compounds, melanocortin receptor agonists or antagonists, can be used in order to treat pathological states or metabolic diseases, of the nervous or dermatological system in which one or more melanocortin receptors are involved such as the following examples: inflammatory states, energy homeostasis disorders, food intake disorders, weight disorders (obesity, cachexia, anorexia), sexual activity disorders (erectile disorders), neuropathic pain. Mental disorders can also be mentioned (anxiety, depression), drug addition, skin diseases (acne, dermatitis, cutaneous cancers, melanomas). These compounds can also be used for stimulating nerve regeneration.

DETAILED DESCRIPTION OF THE INVENTION

A subject of the invention is therefore a compound of general formula (I)

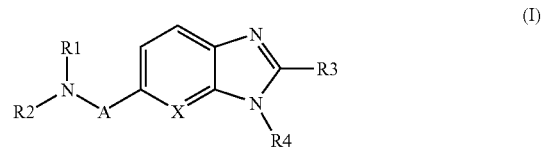

in racemic, enantiomeric form or any combinations of these forms and in which:

A represents —$CH_2$—, —C(O)—, —C(O)—C($R_a$)($R_b$)—;
X represents the —CH— radical or the nitrogen atom;
$R_a$ and $R_b$ represent, independently, the hydrogen atom or a ($C_1$-$C_6$)alkyl radical;
$R_1$ represents the hydrogen atom or a ($C_1$-$C_8$)alkyl radical;
$R_2$ represents a ($C_1$-$C_8$)alkyl radical;
or $R_1$ and $R_2$ form together with the nitrogen atom to which they are attached, a heterobicycloalkyl or a heterocycloalkyl optionally substituted by one or more identical or different ($C_1$-$C_6$)alkyl substituents;
$R_3$ represents —$(CH_2)_p$—$Z_3$, —C(O)—$Z'_3$, —CH(OH)—$Z'_3$ or —C(O)—NH—$Z''_3$;
 $Z_3$ represents a ($C_1$-$C_6$)alkyl, ($C_2$-$C_6$)alkenyl, ($C_1$-$C_6$)alkoxy, ($C_1$-$C_6$)alkyl-carbonyl, ($C_1$-$C_6$)alkoxy-carbonyl, ($C_1$-$C_6$)alkyl-N($R_N$)-carbonyl, ($C_3$-$C_7$)cycloalkyl, heterocycloalkyl, aryl, aryl-thio or heteroaryl radical, $Z_3$ being linked to the —$(CH_2)_p$— radical by a carbon atom,
 the ($C_3$-$C_7$)cycloalkyl and heterocycloalkyl radicals being optionally substituted by one or more identical or different radicals chosen from ($C_1$-$C_6$)alkyl and oxy;
 the heteroaryl radical being optionally substituted by one or more identical or different substituents chosen from: halo, nitro or —(CH—$_2)_p$-$V_{30}$—$Y_3$;
 the aryl radical being optionally substituted by one or more identical or different substituents chosen from: halo, nitro, cyano, ($C_2$-$C_6$)alkenyl, heterocycloalkyl, aryl, aryloxy, aralkyl-oxy, heteroaryl and —$(CH_2)_p$-$V_{31}$—$Y_3$;
 $V_{30}$ represents —O—, —C(O)—, —C(O)—O— or a covalent bond;
 $V_{31}$ represents —O—, —S—, —$SO_2$—, —C(O)—, —C(O)—O—, —N($R_N$)—, —NH—C(O)—, —C(O)—NR'$_3$—, —NH—C(O)—NR'$_3$— or a covalent bond;
 $Y_3$ represents the hydrogen atom or a ($C_1$-$C_6$)alkyl radical optionally substituted by one or more identical or different halo radicals;

$R_N$ represents a hydrogen atom or a $(C_1-C_6)$alkyl radical; or $Z_3$ represents a radical of formula

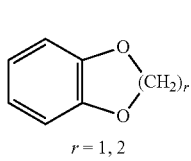 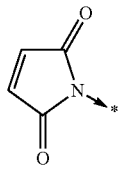

$Z'_3$ represents an aryl radical optionally substituted by one or more identical or different substituents chosen from: halo, nitro and $-(CH_2)_{p'}-V'_3-Y'_3$;

$V'_3$ represents $-O-$, $-C(O)-$, $-C(O)-O-$, $-NH-C(O)-$, $-C(O)-NR'_3-$ or a covalent bond;

$Y'_3$ represents the hydrogen atom or a $(C_1-C_6)$alkyl radical optionally substituted by one or more identical or different halo radicals;

$R'_3$ represents the hydrogen atom, a $(C_1-C_6)$alkyl or $(C_1-C_6)$alkoxy radical;

$A''_3$ represents a $(C_1-C_6)$alkyl, aryl or heteroaryl radical; the alkyl and aryl radicals being optionally substituted by one or more identical or different substituents chosen from halo and $-V''_3-Y''_3$;

$V''_3$ represents $-O-$, $-C(O)-$, $-C(O)-O-$, $-C(O)-NH-$ or a covalent bond;

$Y''_3$ represents the hydrogen atom or a $(C_1-C_6)$alkyl radical optionally substituted by one or more identical or different halo radicals;

p represents an integer from 0 to 6; p' and p'' represent, independently, an integer from 0 to 4; q represents an integer from 0 to 2;

$R_4$ represents a radical of formula $-(CH_2)_s-R'_4$;

$R'_4$ represents a heterocycloalkyl containing at least one nitrogen atom and optionally substituted by $(C_1-C_6)$alkyl; a heteroaryl containing at least one nitrogen atom and optionally substituted by $(C_1-C_6)$alkyl; or a radical of formula $-NW_4W'_4$;

$W_4$ represents the hydrogen atom or $(C_1-C_8)$alkyl;

$W'_4$ represents a radical of formula $-(CH_2)_{s'}-Z_4$ in which $Z_4$ represents the hydrogen atom, a $(C_1-C_8)$alkyl or $(C_3-C_7)$cycloalkyl radical;

s and s' represent, independently, an integer from 0 to 6; or a pharmaceutically acceptable salt of the latter.

In the definitions indicated above, the expression halo represents the fluoro, chloro, bromo or iodo radical, preferably chloro, fluoro or bromo. The expression alkyl (unless otherwise specified), preferably represents a linear or branched alkyl radical having 1 to 6 carbon atoms, such as the methyl, ethyl, propyl, isopropyl, butyl, isobutyl, sec-butyl and tert-butyl, pentyl or amyl, isopentyl, neopentyl, 2,2-dimethyl-propyl, hexyl, isohexyl or 1,2,2-trimethyl-propyl radicals. The term $(C_1-C_8)$alkyl designates a linear or branched alkyl radical having 1 to 8 carbon atoms, such as the radicals containing 1 to 6 carbon atoms as defined above but also heptyl, octyl, 1,1,2,2-tetramethyl-propyl, 1,1,3,3-tetramethyl-butyl. The term alkyl-carbonyl designates the radicals in which the alkyl radical is as defined above such as for example methyl-carbonyl, ethyl-carbonyl. The term alkyl-N($R_N$)-carbonyl designates the radicals in which the alkyl radical is as defined above such as for example methyl-aminocarbonyl, ethyl-aminocarbonyl, N-propyl-N-methylaminocarbonyl, N,N-diethylaminocarbonyl.

By alkenyl, unless otherwise specified, is meant a linear or branched alkyl radical containing 2 to 6 carbon atoms and having at least one unsaturation (double bond), such as for example vinyl, allyl, propenyl, butenyl or pentenyl.

The term alkoxy designates the radicals in which the alkyl radical is as defined above such as for example the methoxy, ethoxy, propyloxy or isopropyloxy radicals but also linear, secondary or tertiary butoxy, pentyloxy. The term alkoxycarbonyl preferably designates the radicals in which the alkoxy radical is as defined above such as for example methoxycarbonyl, ethoxycarbonyl.

The term $(C_3-C_7)$cycloalkyl designates a saturated carbonaceous monocyclic system comprising 3 to 7 carbon atoms, and preferably the cyclopropyl, cyclobutyl, cyclopentyl, cyclohexyl or cycloheptyl rings. The expression heterocycloalkyl designates a condensed saturated monocyclic or bicyclic system containing 2 to 7 carbon atoms and at least one heteroatom. This radical can contain several identical or different heteroatoms. Preferably, the heteroatoms are chosen from oxygen, sulphur or nitrogen. As an example of heterocycloalkyl, there can be mentioned rings containing at least one nitrogen atom such as pyrrolidine, imidazolidine, pyrazolidine, isothiazolidine, thiazolidine, isoxazolidine, oxazolidine, piperidine, piperazine, azepane (azacycloheptane), azacyclooctane, diazepane, morpholine, decahydroisoquinoline (or decahydroquinoline) but also rings containing no nitrogen atom such as tetrahydrofuran or tetrahydrothiophene. As examples of a heterocycloalkyl optionally substituted by oxy and alkyl, there can be mentioned the lactones and the lactams.

The term heterobicycloalkyl designates a non-condensed saturated hydrocarbon bicyclic system containing 5 to 8 carbon atoms and at least one heteroatom chosen from nitrogen, oxygen and sulphur. As examples of a heterobicycloalkyl, there can be mentioned aza-bicycloheptane aza-bicyclooctane such as 7-aza-bicyclo[2,2,1]heptane, 2-aza-bicyclo[2,2,2]octane or 6-aza-bicyclo[3,2,1]octane.

The expression aryl represents an aromatic radical, constituted by a condensed ring or rings, such as for example the phenyl, naphthyl or fluorenyl radical. The expression arylthio represents a radical, the aryl radical of which is as defined above such as for example phenylthio. The expression aryloxy represents the radicals in which the aryl radical is as defined above such as for example phenyloxy, napthyloxy.

The term aralkyl (arylalkyl) preferably designates the radicals in which the aryl and alkyl radicals are as defined above such as for example benzyl or phenethyl. The expression aralkyloxy designates the radicals in which the aralkyl radicals are as defined above such as for example benzyloxy, phenethyloxy.

The expression heteroaryl designates an aromatic radical, constituted by a condensed ring or rings, with at least one ring containing one or more identical or different heteroatoms chosen from sulphur, nitrogen or oxygen. As examples of a heteroaryl radical, there can be mentioned the radicals containing at least one nitrogen atom such as pyrrolyl, imidazolyl, pyrazolyl, isothiazolyl, thiazolyl, isoxazolyl, oxazolyl, triazolyl, thiadiazolyl, pyridyl, pyrazinyl, pyrimidyl, quinolyl, isoquinolyl, quinoxalinyl, indolyl, benzoxadiazoyl, benzothiazolyl, carbazolyl but also the radicals containing no nitrogen atom such as thienyl, benzothienyl, furyl, benzofuryl or pyranyl.

Also in the present application, the $(CH_2)_i$ radical (i being an integer which can represent p, p', p'', s and s' as defined above), represents a linear or branched hydrocarbon chain of I carbon atoms. Thus the $-(CH_2)_3-$ radical can represent $-CH_2-CH_2-CH_2-$ but also $-CH(CH_3)-CH_2-$, $-CH_2CH(CH_3)-$ or $-C(CH_3)_2-$.

The invention preferably relates to compounds of formula I as defined above and characterized in that X represents the —CH— radical; or a pharmaceutically acceptable salt of the latter.

Preferably also, the invention relates to compounds of formula I as defined above and characterized in that $R_1$ represents the hydrogen atom or a $(C_1\text{-}C_6)$alkyl radical, and $R_2$ represents a $(C_1\text{-}C_8)$alkyl radical; and very preferentially $R_1$ represents a $(C_1\text{-}C_6)$alkyl radical and $R_2$ represents a $(C_1\text{-}C_6)$ alkyl radical; or a pharmaceutically acceptable salt of the latter.

Preferably also, the invention relates to compounds of formula I as defined above and characterized in that A represents —$CH_2$—; or a pharmaceutically acceptable salt of the latter.

Preferably also, the invention relates to compounds of formula I as defined above and characterized in that A represents —C(O)—C($R_a$)($R_b$)— and $R_a$ and $R_b$ represent, independently, the methyl radical; or a pharmaceutically acceptable salt of the latter.

Preferably also, the invention relates to compounds of formula I as defined above and characterized in that A represents —C(O)—; or a pharmaceutically acceptable salt of the latter.

Preferably also, the invention relates to compounds of formula I as defined above and characterized in that
$R_4$ represents a radical of formula —$(CH_2)_s$—$R'_4$;
$R'_4$ represents a heterocycloalkyl containing at least one nitrogen atom optionally substituted by $(C_1\text{-}C_6)$alkyl; or a radical of formula —$NW_4W'_4$;
$W_4$ represents the hydrogen atom or $(C_1\text{-}C_8)$alkyl;
$W'_4$ represents a radical of formula —$(CH_2)_{s'}$—$Z_4$ in which $Z_4$ represents the hydrogen atom or a $(C_1\text{-}C_8)$alkyl radical;
s and s' represent, independently, an integer from 1 to 6; or a pharmaceutically acceptable salt of the latter.

Very preferentially, the invention relates to compounds of formula I as defined above and characterized in that $R_4$ represents a radical of formula —$(CH_2)_s$—$R'_4$; $R'_4$ represents a radical of formula —$NW_4W'_4$;
$W_4$ represents a $(C_1\text{-}C_8)$alkyl radical;
$W'_4$ represents a radical of formula —$(CH_2)_{s'}$—$Z_4$ in which $Z_4$ represents the hydrogen atom or a $(C_1\text{-}C_8)$alkyl radical;
s and s' represent, independently, an integer from 2 to 6; or a pharmaceutically acceptable salt of the latter.

Very preferentially also, the invention relates to compounds of formula I as defined above and characterized in that $R_4$ represents a radical of formula —$(CH_2)_s$—$R'_4$;
$R'_4$ represents a heterocycloalkyl containing at least one nitrogen atom and optionally substituted by $(C_1\text{-}C_6)$ alkyl; and s represents an integer from 2 to 6;
and more particularly $R'_4$ represents the piperidine or pyrrolidine ring; s represents an integer from 1 to 4; or a pharmaceutically acceptable salt of the latter.

Preferably also, the invention relates to compounds of formula I as defined above and characterized in that $R_3$ represents —$(CH_2)_p$—$Z_3$ and
$Z_3$ represents a $(C_1\text{-}C_6)$alkyl, $(C_1\text{-}C_6)$alkenyl $(C_1\text{-}C_6)$ alkoxy, $(C_1\text{-}C_6)$alkyl-carbonyl, $(C_1\text{-}C_6)$alkoxy-carbonyl, $(C_1\text{-}C_6)$alkyl-N($R_N$)carbonyl, $(C_3\text{-}C_7)$cycloalkyl, heterocycloalkyl, aryl, aryl-thio or heteroaryl radical,
the $(C_3\text{-}C_7)$cycloalkyl and heterocycloalkyl radicals being optionally substituted by one or more identical or different radicals chosen from $(C_1\text{-}C_6)$alkyl and oxy;
the heteroaryl radical being optionally substituted by one or more identical or different substituents chosen from: halo, nitro or —$(CH_2)p$-$V_{30}$—$Y_3$;
the aryl radical being optionally substituted by one or more identical or different substituents chosen from: halo, nitro, $(C_2\text{-}C_6)$alkenyl, heterocycloalkyl, aryl, aryloxy, aralkyl-oxy, heteroaryl and —$(CH_2)_p$-$V_{31}$—$Y_3$;
$V_{30}$ represents —O—, —C(O)—, —C(O)—O— or a covalent bond;
$V_{31}$ represents —O—, —S—, —$SO_2$—, —C(O)—, —C(O)—O—, —N($R_N$)—, —NH—C(O)—, —C(O)—$NR'_3$— or a covalent bond;
$Y_3$ represents the hydrogen atom or a $(C_1\text{-}C_6)$alkyl radical optionally substituted by one or more identical or different halo radicals;
$R_N$ represents a hydrogen atom or a $(C_1\text{-}C_6)$alkyl radical;
or $Z_3$ represents a radical of formula

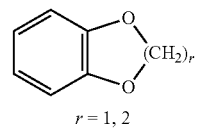

$r = 1, 2$ or a pharmaceutically acceptable salt of the latter;

Preferably also, the invention relates to compounds of formula I as defined above and characterized in that $Z_3$ represents a $(C_1\text{-}C_6)$alkyl, $(C_1\text{-}C_6)$alkyl-carbonyl, $(C_1\text{-}C_6)$alkoxy-carbonyl, $(C_1\text{-}C_6)$alkyl-N($R_N$)-carbonyl, $(C_3\text{-}C_7)$cycloalkyl, aryl or heteroaryl radical, the aryl and heteroaryl radicals being optionally substituted;
and very preferentially
the heteroaryl radical is optionally substituted by one or more identical or different substituents chosen from: halo and —$(CH_2)_p$-$V_{30}$—$Y_3$;
the aryl radical is optionally substituted by one or more identical or different substituents chosen from: nitro and —$(CH_2)_p$-$V_{31}$—$Y_3$;
$V_{30}$ represents —O—, —C(O)—, —C(O)—O— or a covalent bond;
$V_{31}$ represents —O—, —C(O)—, —C(O)—O— or —$SO_2$—;
$Y_3$ represents a $(C_1\text{-}C_6)$alkyl radical;
p and p' represent, independently, an integer from 0 to 4; or a pharmaceutically acceptable salt of the latter.

Very preferentially also, the invention relates to compounds of formula I as defined above and characterized in that $Z_3$ represents a $(C_1\text{-}C_6)$alkyl radical; or a pharmaceutically acceptable salt of the latter.

Very preferentially also, the invention relates to compounds of formula I as defined above and characterized in that $Z_3$ represents a $(C_1\text{-}C_6)$alkyl-carbonyl, $(C_1\text{-}C_6)$alkoxy-carbonyl or $(C_1\text{-}C_6)$alkyl-N($R_N$)-carbonyl radical; or a pharmaceutically acceptable salt of the latter.

Very preferentially also, the invention relates to compounds of formula I as defined above and characterized in that $Z_3$ represents a heteroaryl optionally substituted by one or more identical or different substituents chosen from: halo and —$(CH_2)_{p'}$-$V_{30}$—$Y_3$;
$V_{30}$ represents —O—, —C(O)—, —C(O)—O— or a covalent bond;
$Y_3$ represents a $(C_1\text{-}C_6)$alkyl radical;
p' represents an integer from 0 to 4;
and more particularly $Z_3$ represents the thienyl, furyl, benzofuryl, benzothienyl, thiazolyl, pyrazolyl, imidazolyl, pyridinyl, indolyl radical; or a pharmaceutically acceptable salt of the latter.

Very preferentially also, the invention relates to compounds of formula I as defined above and characterized in that $Z_3$ represents a $(C_3\text{-}C_7)$cycloalkyl or aryl radical, the aryl radical being optionally substituted by one or more identical or different substituents chosen from: nitro or —$(CH_2)_p$—$V_{31}$—$Y_3$;

$V_{31}$ represents —O—, —C(O)—, —C(O)—O— or —SO$_2$—;
$Y_3$ represents a ($C_1$-$C_6$)alkyl radical;
p' represents an integer from 0 to 4;
and more particularly the ($C_3$-$C_7$)cycloalkyl radical is chosen from cyclopentyl and cyclohexyl; the aryl radical is the phenyl radical; or a pharmaceutically acceptable salt of the latter.

Very preferentially also, the invention relates to compounds of formula I as defined above and characterized in that $R_3$ represents —C(O)—Z'$_3$; or a pharmaceutically acceptable salt of the latter.

Very preferentially also, the invention relates to compounds of formula I as defined above and characterized in that Z'$_3$ represents a phenyl radical optionally substituted by one or more identical or different substituents of formula —(CH$_2$)$_{p''}$-V'$_3$—Y'$_3$;
V'$_3$ represents —O—;
Y'$_3$ represents a ($C_1$-$C_6$)alkyl radical;

p'' represents an integer from 0 to 4; or a pharmaceutically acceptable salt of the latter.

Very preferentially also, the invention relates to compounds of formula I as defined above and characterized in that $R_3$ represents —C(O)—NH—Z''$_3$
Z''$_3$ represents a —(CH$_2$)$_q$-A''$_3$ radical;
A''$_3$ represents a ($C_1$-$C_6$)alkyl, phenyl or thienyl radical;
the alkyl and aryl radicals being optionally substituted by one or more identical or different substituents of formula -V''$_3$—Y''$_3$;
V''$_3$ represents —O—, —C(O)—, —C(O)—O— or a covalent bond;
Y''$_3$ represents the hydrogen atom or a ($C_1$-$C_6$)alkyl radical;
q represents an integer from 0 to 1; or a pharmaceutically acceptable salt of the latter.

In the present Application, the symbol ->* corresponds to the attachment point of the radical. When the attachment site is not specified on the radical, this means that the attachment is carried out on one of the sites available on this radical for such an attachment.

Following the definitions of the variable groups A, X, $R_1$, $R_2$, $R_3$ and $R_4$, the compounds according to the invention can be prepared in liquid phase according to the different procedures A to D described below.

A. Preparation According to Reaction Diagram A

The compounds of formula I according to the invention in which A represents —C(O)—, can be prepared according to the following diagram. A:

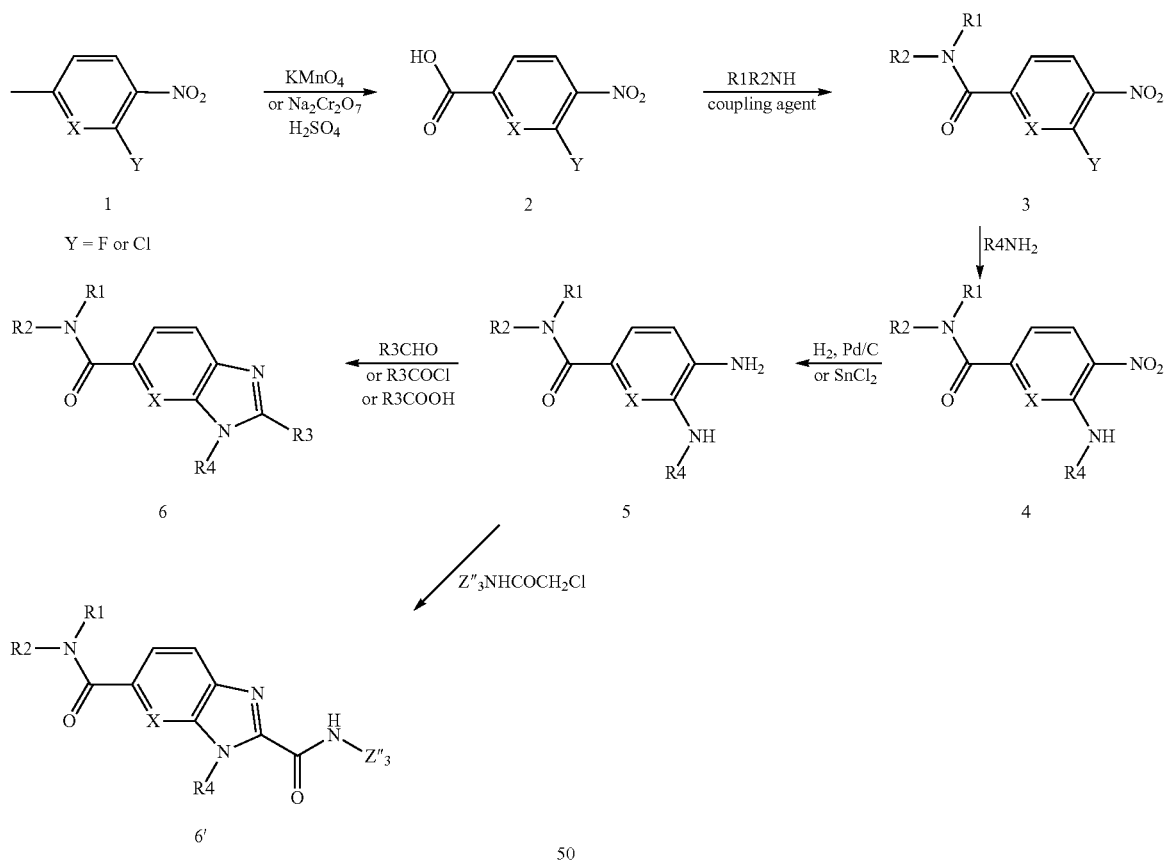

As described in diagram A, the methylated derivative (1) (for X=CH commercial compound; for X=N compound prepared according to the procedure of Baumgarten et al., *J. Am. Chem. Soc*, 1952, 74, 3828-3831, from 6-methyl-3-nitro-pyridine-amine) can be oxidized to carboxylic acid (2) by an aqueous solution of potassium permanganate at a temperature of 100° C. for 3 to 6 hours (according to the procedure of Schmelkes et al., *J. Am. Chem. Soc,* 1944, 1631), or by an aqueous solution of sodium dichromate in the presence of sulphuric acid at a temperature of 20-90° C. for 1 to 3 hours (according to the procedure of Howes et al., *European J. Med. Chem,* 1999, 34, 225-234). The carboxylic acid (2) can be coupled with a primary or secondary amine in the presence of a coupling agent such as diisopropylcarbodiimide (DIC), dicyclohexylcarbodiimide (DCC), 1-(3-dimethylaminopropyl)-3-ethylcarbodiimide hydrochloride (EDC) or carbonyldiimidazole (CDI) with or without 1-hydroxybenzotriazole (HOBt) in an inert organic solvent such as methylene chloride, tetrahydrofuran or dimethylformamide at ambient temperature for 3 to 24 hours in order to produce the corresponding amide (3). Treatment of the fluorinated or chlorinated derivative (3) by a primary amine in the presence of an inorganic base such as cesium or potassium carbonate in an inert organic solvent such as dimethylformamide or acetonitrile at a temperature of 20-100° C. for 2 to 48 hours produces the derivative (4). The nitro function of the compound (4) is reduced by treatment with stannous chloride dihydrate in an inert solvent such as ethyl acetate or dimethylformamide at a temperature of 60-80° for 3 to 15 hours, or by catalytic hydrogenation in the presence of 10% palladium on carbon in an inert solvent such as methanol, ethanol, ethyl acetate or a mixture of these solvents, at a temperature of 18-25° C., for 2 to 8 hours in order to produce dianiline (5). The derivative (5) can then be treated by an aldehyde in the presence of an oxidizing agent such as nitrobenzene, DDQ in an aprotic solvent such as dimethylformamide at a temperature of 60-180° C. for 2 to 24 hours, or in a microwave at a temperature of 150-200° C. for 5 to 30 minutes, in order, to produce benzimidazole (6). Alternatively, the derivative (5) can react either with an acid chloride, or with a carboxylic acid in the presence of a coupling agent such as diisopropylcarbodiimide (DIC), dicyclohexylcarbodiimide (DCC), 1-(3-dimethylaminopropyl)-3-ethylcarbodiimide hydrochloride (EDC), carbonyldiimidazole (CDI), 2-(1H-benzotriazole-1-yl)-1,1,3,3-tetramethyluronium hexafluorophosphate (HBTU), 2-(1H-benzotriazole-1-yl)-1,1,3,3-tetramethyluronium tetrafluoroborate (TBTU) or O-(7-azobenzotriazol-1-yl)-1,1,3,3-tetramethyluronium hexafluorophosphate (HATU) in an inert organic solvent such as methylene chloride, tetrahydrofuran or dimethylformamide at ambient temperature for 3 to 24 hours in order to produce the corresponding amide. The amide thus obtained produces benzimidazole (6) by treatment with an acid, such as acetic acid, hydrochloric acid, polyphosphoric acid at a temperature of 20-100° C. for 2 to 24 hours or in a microwave at a temperature of 80-150° C. for 5 to 30 minutes. The derivative (5) can also react with an imidate ester or a chloroacetamide derivative in an organic solvent such as dimethylformamide or methanol or ethanol, in the presence or absence of a tertiary base, sulphur, at a temperature of 20-100° C. for 3 to 24 hours, or in a microwave at a temperature of 80-130° C. for 5 to 30 minutes in order to produce the benzimidazole derivative (6').

Example A1

2-(4-methoxyphenyl)-N,N-bis(3-methylbutyl)-1-(3-piperidin-1-ylpropyl)-1H-benzimidazole-6-carboxamide hydrochloride

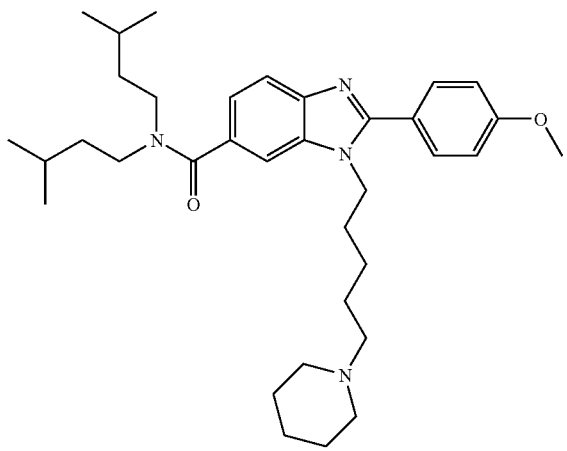

Stage 1

3-fluoro-4-nitrobenzoic acid

A mixture of 3-fluoro-4-nitrotoluene (10 g, 1 eq) and potassium permanganate (25.5 g, 2.5 eq) in water (1 l) is heated to reflux for 6 hours then cooled down to ambient temperature. The mixture is filtered on celite and the aqueous phase is washed twice with diethyl ether (2×300 ml). The aqueous phase is acidified with an aqueous solution of concentrated hydrochloric acid (12N) then concentrated under reduced pressure at 40° C. to a volume of approximately 300 ml. The precipitate formed is filtered then washed with petroleum ether and dried in order to produce the expected compound in the form of a white solid (6.9 g; 58% yield).

NMR $^1$H (400 MHz, DMSO-$d_6$): δ 7.93 (m, 2H), 8.25 (m, 1H), 13.95 (m, 1H).

Stage 2

3-fluoro-N,N-bis(3-methylbutyl)-4-nitrobenzamide 1-(3-dimethylaminopropyl)-3-ethylcarbodiimide hydrochloride (EDC) (4.4 g, 1.1 eq) in solution in chloroform (25 ml) and 1-hydroxybenzotriazole (HOBt) (3.05 g, 1.1 eq) in solution in THF (40 ml) are successively added to 3-fluoro-4-nitrobenzoic acid (3.8 g, 1 eq) in solution in anhydrous THF (30 ml). The mixture is stirred for 1 hour at a temperature of approximately 20° C. then diisoamylamine (3.6 g, 1.1 eq) in solution in THF (30 ml) is added. After stirring for 16 hours at a temperature of approximately 20° C., the reaction mixture is concentrated under reduced pressure at 40° C. The residue is taken up in dichloromethane (200 ml) and water (70 ml). After decantation and extraction, the combined organic phases are washed with salt water, dried over $Na_2SO_4$ then concentrated under reduced pressure at 40° C. Purification of the compound by flash chromatography on silica gel (eluent: heptane/ethyl acetate 9:1) produces the expected compound in the form of a yellow oil (4.3 g; 65% yield).

MS/LC: Calculated MM=324.4; m/z=325.2 (MH+)

NMR $^1$H (400 MHz, DMSO-$d_6$): δ 0.69 (m, 6H), 0.93 (m, 6H), 1.35-1.60 (m, 6H), 3.09 (m, 2H), 3.41 (m, 2H), 7.38 (d, 1H), 7.63 (d, 1H), 8.21 (t, 1H).

Stage 3

N,N-bis(3-methylbutyl)-4-nitro-3-[(3-piperidin-1-ylpropyl)amino]benzamide

A mixture of 3-fluoro-N,N-bis(3-methylbutyl)-4-nitrobenzamide (430 mg, 1 eq), 3-piperidino-propylamine (212 mg, 1.1 eq) and potassium carbonate (365 mg, 2 eq) in acetonitrile (10 ml) is heated under reflux for 3 hours then concentrated under reduced pressure at 40° C. The residue is taken up in dichloromethane (50 ml) and water (20 ml). After decantation and extraction, the combined organic phases are washed with salt, water, dried over $Na_2SO_4$ then concentrated under reduced pressure at 40° C. Purification of the residue by flash chromatography on silica gel (eluent: heptane/ethyl acetate 1:1 to 100% ethyl acetate) produces the expected compound in the form of a yellow oil (460 mg; 78% yield).

MS/LC: calculated MM=446.6; m/z=447.3 (MH+)

NMR $^1$H (400 MHz, DMSO-$d_6$): δ 0.68 (d, 6H), 0.92 (d, 6H), 1.31-1.69 (m, 2H), 1.74 (m, 2H), 2.32 (m, 6H), 3.10 (m, 2H), 3.38 (m, 4H), 6.53 (d, 1H), 6.91 (m, 1H), 8.09 (d, 1H), 8.44 (t, 1H).

Stage 4

4-amino-N,N-bis(3-methylbutyl)-3-[(3-piperidin-1-ylpropyl)amino]benzamide

N,N-bis(3-methylbutyl)-4-nitro-3-[(3-piperidin-1-ylpropyl)amino]benzamide (1 g) in solution in a mixture of ethyl acetate/ethanol 2:1 (100 ml) and 10% palladium on carbon (100 mg) are introduced into an autoclave. After stirring for 3 hours under a hydrogen atmosphere (3 bars) at a temperature of approximately 20° C., the catalyst is eliminated by filtration on celite and the filtrate is concentrated under reduced pressure at 40° C. in order to produce the expected compound in the form of an oil (910 mg, 97% yield).

MS/LC: Calculated MM 416.6; m/z=417.3 (MH+)

NMR $^1$H (400 MHz, DMSO-$d_6$): δ 0.81 (d, 12H), 1.39-1.69 (m, 12H), 1.73 (m, 2H), 2.32 (m, 6H), 3.03 (m, 2H), 3.38 (m, 4H), 4.62 (s, 1H), 4.76 (s, 2H), 6.36 (s, 1H), 6.42 (AB, 1H), 6.50 (AB, 1H).

Stage 5

2-(4-methoxyphenyl)-N,N-bis(3-methylbutyl)-1-(3-piperidin-1-ylpropyl)-1H-benzimidazole-6-carboxamide hydrochloride p-anisaldehyde (27 mg, 1.3 eq) is added to a solution of 4-amino-N,N-bis(3-methylbutyl)-3-[(3-piperidin-1-ylpropyl)amino]benzamide (62 mg) in nitrobenzene (2 ml). The mixture is heated at 130° C. for 6 hours. Purification of the mixture by flash chromatography on silica gel (eluent: 100% dichloromethane to dichloromethane/methanol 9:1) produces the expected compound in the form of the free base. The corresponding hydrochloride salt is formed by the addition of a 1N solution of hydrochloric acid in diethyl ether. The precipitate obtained is filtered and dried in order to produce the expected monohydrochloride compound (58 mg, 68% yield).

MS/LC: Calculated MM 532.8; m/z=533.5 (MH+)

NMR $^1$H (400 MHz, DMSO-$d_6$): δ 0.68 (d, 6H), 0.95 (d, 6H), 1.26-1.69 (m, 2H), 2.27 (m, 2H), 2.72 (m, 2H), 3.03 (m, 2H), 3.25 (m, 4H), 3.45 (m, 2H), 3.91 (s, 3H), 4.56 (t, 2H), 7.27 (AB, 2H), 7.50 (AB, 1H), 7.87 (AB, 1H), 7.92 (AB, 1H), 8.15 (s, 1H), 10.89 (s, 1H).

Example A2

2-(4-methoxybenzyl)-N,N-bis(3-methylbutyl)-1-(3-piperidin-1-ylpropyl)-1H-benzimidazole-6-carboxamide hydrochloride

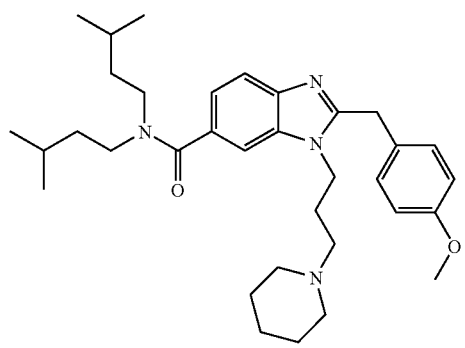

4-methoxyphenylacetylchloride (32 mg, 1.1 eq) is added to a solution of 4-amino-N,N-bis(3-methylbutyl)-3-[(3-piperidin-1-ylpropyl)amino]benzamide (66 mg) in acid acetic (2 ml). The mixture is heated at 100° C. for 18 hours then cooled down and concentrated under reduced pressure. A saturated aqueous solution of sodium hydrogen carbonate is added to the residue obtained dissolved in dichloromethane. After decantation and extractions, the combined organic phases are washed with salt water, dried over $Na_2SO_4$ and concentrated under reduced pressure. Purification of the residue obtained by flash chromatography on silica gel (eluent: 100% dichloromethane to dichloromethane/methanol 9:1) produces the expected compound in the form of the free base. The corresponding hydrochloride salt is formed by the addition of a 1N solution of hydrochloric acid in diethyl ether. The precipitate obtained is filtered and dried in order to produce the expected monohydrochloride compound (51 mg, 59% yield).

MS/LC: Calculated MM=546.8; m/z=547.5 (MH+)

NMR $^1$H (400 MHz, DMSO-$d_6$): δ 0.63 (d, 6H), 0.94 (d, 6H), 1.24-1.92 (m, 12H), 2.11 (m, 2H), 2.73 (m, 2H), 3.03-3.29 (m, 6H), 3.40 (m, 2H), 3.74 (s, 3H), 4.56 (t, 2H), 4.62 (s, 2H), 6.96 (AB, 2H), 7.43 (m, 3H), 7.79 (AB, 1H), 8.03 (s, 1H), 11.02 (s, 1H).

Example A3

2-[3-(methylamino)-3-oxopropyl]-N,N-bis(3-methylbutyl)-1-(3-piperidin-1-ylpropyl)-1H-benzimidazole-6-carboxamide hydrochloride

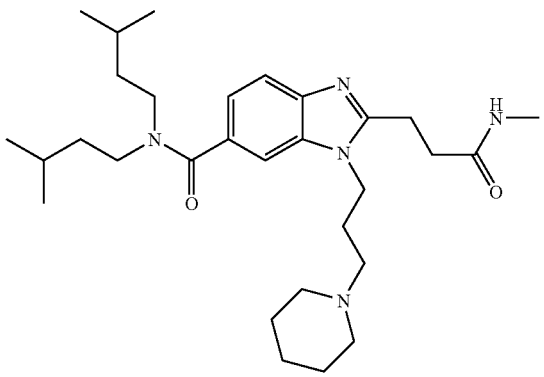

TBTU (67 mg, 1 eq) and diisopropylethylamine (70 μL, 2 eq) are successively added to a solution of N-methylsuccinimic acid (26 mg, 1 eq) in DMF (1 ml). After stirring for 30 minutes at ambient temperature, a solution of 4-amino-N,N-bis(3-methylbutyl)-3-[(3-piperidin-1-ylpropyl)amino]benzamide (66 mg) in DMF (1 ml) is added to the mixture. The mixture is stirred for 15 hours at a temperature of approximately 20° C. then diluted in ethyl acetate (10 ml) and a saturated aqueous solution of sodium hydrogen carbonate (4 ml) is added. After decantation and extractions, the combined organic phases are washed with salt water, dried over $Na_2SO_4$ and concentrated under reduced pressure at 40° C. The oil thus obtained is solubilized in acetic acid (2 ml). The mixture is heated at 100° C. for 18 hours then cooled down to ambient temperature and concentrated under reduced pressure at 40° C. A saturated aqueous solution of sodium hydrogen carbonate is added to the residue obtained dissolved in dichloromethane. After decantation and extractions, the combined organic phases are washed with salt water, dried over $Na_2SO_4$ and concentrated under reduced pressure. Purification of the residue obtained by flash chromatography on silica gel (eluent: dichloromethane 100% to dichloromethane/methanol 85:15) produces the expected compound in the form of the free base. The corresponding hydrochloride salt is formed by the addition of a 1N solution of hydrochloric acid in diethyl ether. The precipitate obtained is filtered and dried in order to produce the expected monohydrochloride compound (64 mg, 54% yield).

MS/LC: Calculated MM=511.8; m/z=512.4 (MH+)

NMR ¹H (400 MHz, DMSO-d₆): δ 0.65 (d, 6H), 0.94 (d, 6H), 1.24-1.90 (m, 12H), 2.29 (m, 2H), 2.56 (d, 3H), 2.82 (m, 2H), 2.93 (t, 2H), 3.16 (m, 4H), 3.33-3.52 (m, 6H), 4.63 (t, 2H), 7.46 (AB, 1H), 7.43 (m, 3H), 7.82 (AB, 1H), 8.10 (s, 1H), 8.20 (m, 1H), 10.86 (s, 1H).

Example A4

2-(1-benzofuran-2-yl)-N,N-dibutyl-1-(3-piperidin-1-ylpropyl)-1H-benzimidazole-6-carboxamide hydrochloride

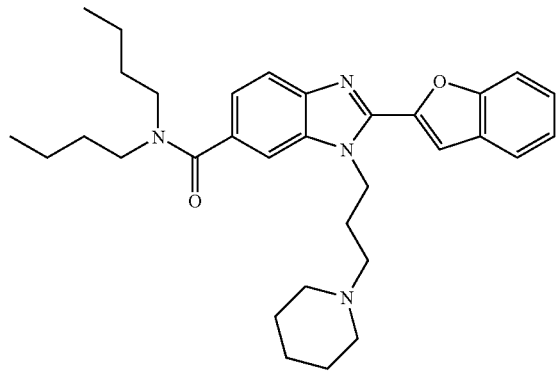

1-benzofuran-2-carbaldehyde (450 mg) is added to a solution of 4-amino-N,N-dibutyl-3-[(3-piperidin-1-ylpropyl)amino]benzamide (1 g) in nitrobenzene (5 ml), placed in a "Personal Chemistry®" reaction tube. The tube is sealed with a cap, placed in the "Personal Chemistry®" microwave and heated under magnetic stirring at 200° C. for 20 minutes. Purification of the mixture obtained by flash chromatography on silica gel (eluent: 100% dichloromethane to dichloromethane/methanol 95:5) produces the expected compound in the form of the free base. The corresponding hydrochloride salt is formed by the addition of a 1N solution of hydrochloric acid in diethyl ether. The precipitate obtained is filtered and dried in order to produce the expected hydrochloride compound (780 mg, 54% yield).

MS/LC: Calculated MM=514.7; m/z=515.5 (MH+)

NMR ¹H (400 MHz, DMSO-d₆): δ 0.70 (broad s, 3H), 0.95 (broad s, 3H), 1.28-1.88 (m, 12H), 2.36 (m, 2H), 2.83 (m, 2H), 2.93 (t, 2H), 3.22 (m, 4H), 3.36 (d, 2H), 3.42 (m, 2H), 4.78 (t, 2H), 7.33 (AB, 1H), 7.42 (t, 1H), 7.52 (t, 1H), 7.79 (AB, 1H), 7.87 (AB, 1H), 7.91 (s, 1H), 7.96 (s, 1H).

Example A5 ethyl 4-({[6-{[bis(3-methylbutyl)amino]carbonyl}-1-(3-piperidin-1-ylpropyl)-1H-benzimidazol-2-yl]carbonyl}amino)benzoate hydrochloride

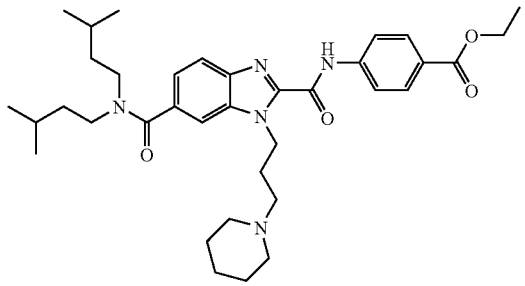

Triethylamine (100 μL), ethyl 4-[(chloroacetyl)amino]benzoate (173 mg) and sulphur (12 mg) are successively added to a solution of 4-amino-N,N-bis(3-methylbutyl)-3-[(3-piperidin-1-ylpropyl)amino]benzamide (100 mg) in etha- nol (3 ml), placed in a "Personal Chemistry®" reaction tube. The tube is sealed with a cap, placed in the "Personal Chemistry®" microwave and heated under magnetic stirring at 130° C. for 20 minutes. The ethanol is then evaporated off and water and dichloromethane are added to the residue. After decantation and extraction, the combined organic phases are washed with salt water, dried over Na₂SO₄ then concentrated under reduced pressure at 40° C. Purification of the compound by flash chromatography on silica gel (eluent: 100% dichloromethane to dichloromethane/ethanol 85:15) produces the expected compound in the form of the free base. The corresponding hydrochloride salt is formed by the addition of a solution of 1N hydrochloric acid in diethyl ether. The precipitate obtained is filtered and dried in order to produce the expected monohydrochloride compound (80 mg, 51% yield).

MS/LC: Calculated MM=617.8; m/z=618.5 (MH+)

NMR ¹H (400 MHz, DMSO-d₆): δ 0.62 (broad s, 6H), 0.95 (broad s, 6H), 1.32 (t, 3H), 1.37-1.75 (m, 12H), 2.30 (m, 2H), 2.83 (m, 2H), 2.93 (t, 2H), 3.17 (m, 4H), 3.37-3.48 (m, 4H), 4.30 (q, 2H), 4.77 (t, 2H), 7.30 (AB, 1H), 7.87 (AB, 1H), 7.88 (s, 1H), 7.97 (AB, 1H), 8.06 (AB, 1H), 10.14 (s, 1H), 11.25 (s, 1H).

According to reaction diagram A and in a manner analogous to the procedures described for the synthesis of 2-(4-methoxyphenyl)-N,N-bis(3-methylbutyl)-1-(3-piperidin-1-ylpropyl)-1H-benzimidazole-6-carboxamide hydrochloride, 2-(4-methoxybenzyl)-N,N-bis(3-methylbutyl)-1-(3-piperidin-1-ylpropyl)-1H-benzimidazole-6-carboxamide, of 2-[3-(methylamino)-3-oxopropyl]-N,N-bis(3-methylbutyl)-1-(3-piperidin-1-ylpropyl)-1H-benzimidazole-6-carboxamide, 2-(1-benzofuran-2-yl)-N,N-dibutyl-1-(3-piperidin-1-ylpropyl)-1H-benzimidazole-6-carboxamide or ethyl 4-({[6-{[bis(3-methylbutyl)amino]carbonyl}-1-(3-piperidin-1-ylpropyl)-1H-benzimidazol-2-yl]carbonyl}amino)benzoate, the following compounds were prepared:

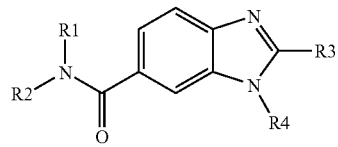

in which R₁R₂N represents one of the radicals below:

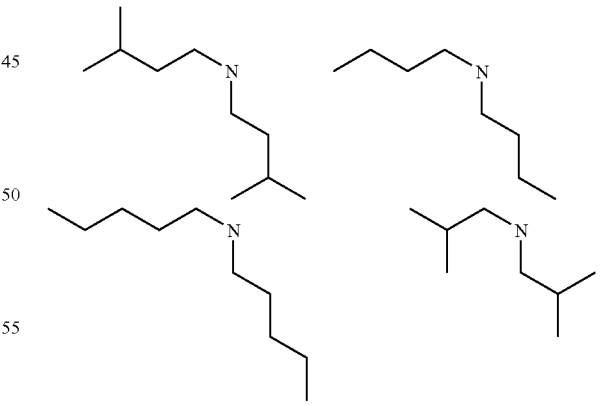

R₃ represents one of the radicals below:

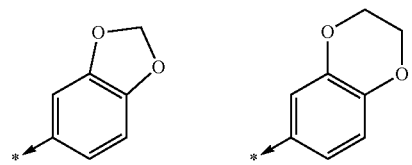

-continued 1 or more substitutions chosen from:

U=H, F, Cl, Br, I, NO₂, OMe, OEt, OPh, SMe, SEt, SCF₃, Me, Et, iPr, tBu, CN, CF₃, OCF₃, C(O)OMe, C(O)OEt, C(O)Me, C(O)Et, C(O)NHMe, C(O)NH₂, NMe₂, NEt₂, NHCOMe, Phe, OCH₂Ph SO₂Me

V=H, F, Cl, Br, I, NO₂, OMe, Me, Et, iPr, CF₃, OCF₃, C(O)OMe, C(O)Me, C(O)NHMe, SO₂Me

-continued
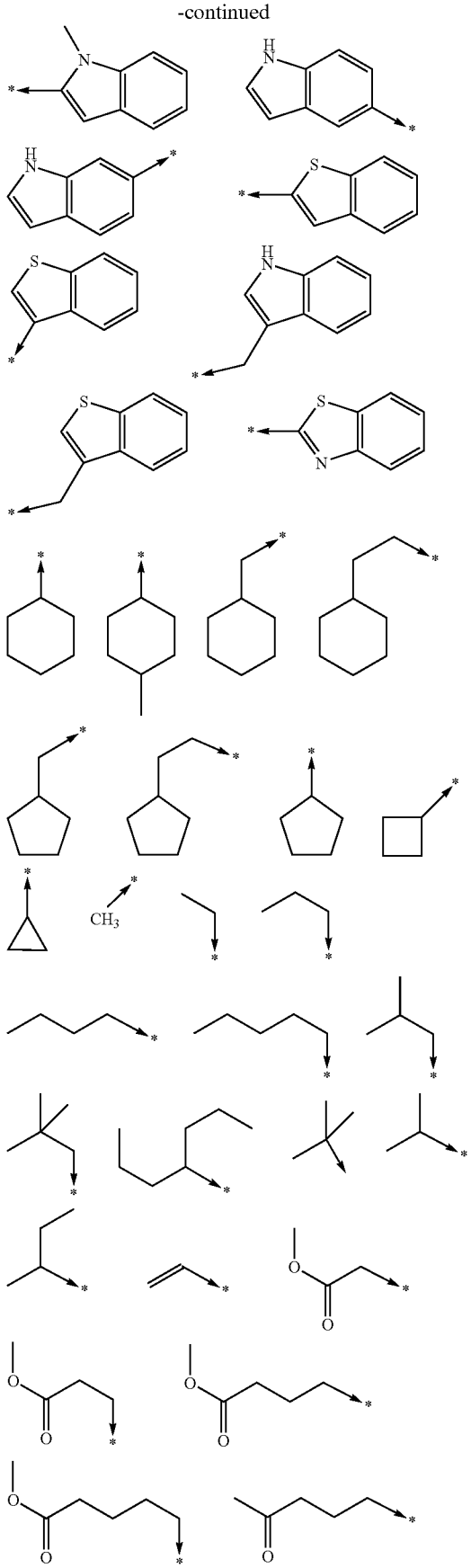
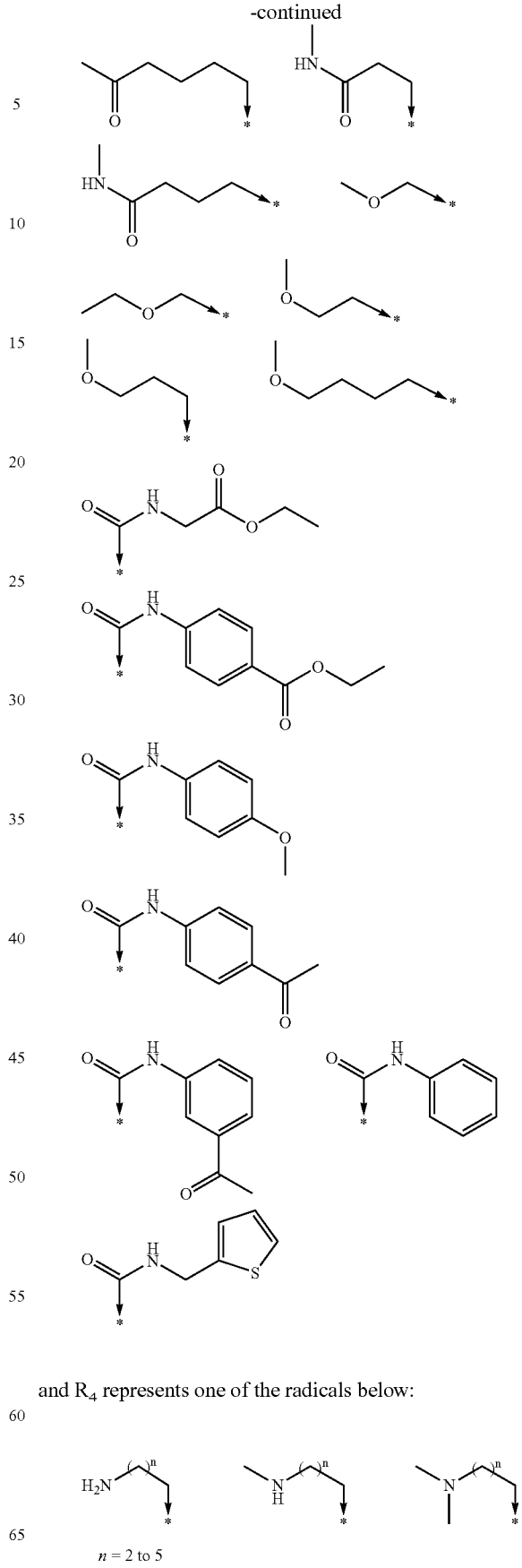
and R₄ represents one of the radicals below:
$n$ = 2 to 5

-continued

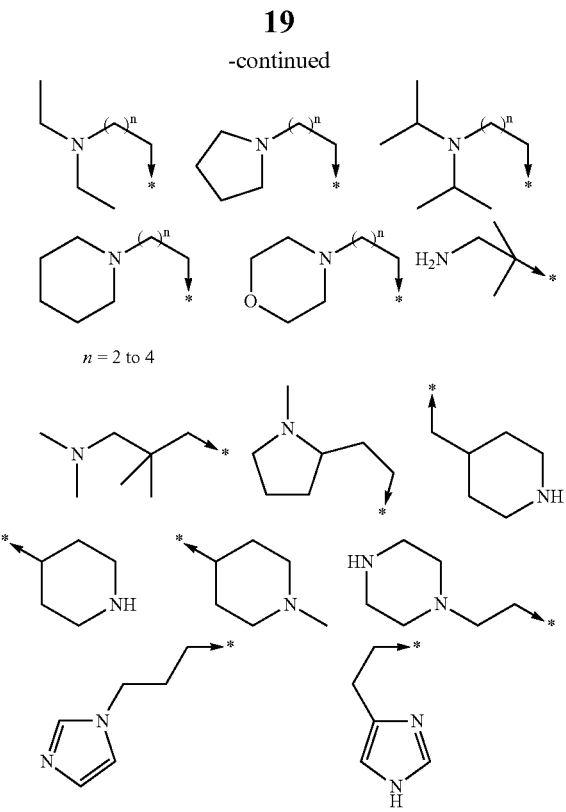

n = 2 to 4

B. Preparation According to Reaction Diagram B

The compounds of formula I according to the invention in which A represents —(CO)— and $R_3$ represents —C(O)—$Z'_3$ ($Z'_3$ representing an aryl radical symbolized by Ar) can be prepared according to the following diagram B:

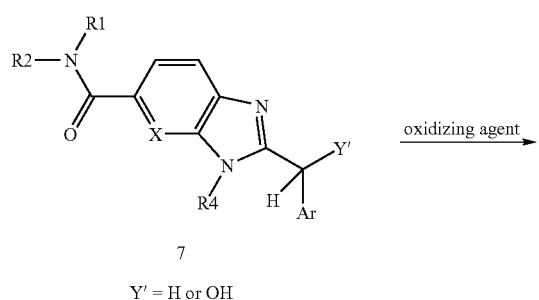

Y' = H or OH

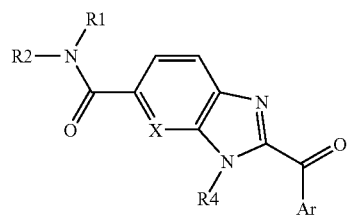

As described in diagram B, the derivative (7) can be oxidized by manganese dioxide in an aprotic solvent such as tetrahydrofuran, dioxane or by chromium trioxide in an acid such as acetic acid, at a temperature of 20-80° C. for 10-96 hours in order to produce the derivative (8).

Example B1

2-(4-methoxybenzoyl)-N,N-bis(3-methylbutyl)-1-(3-piperidin-1-ylpropyl)-1H-benzimidazole-6-carboxamide hydrochloride

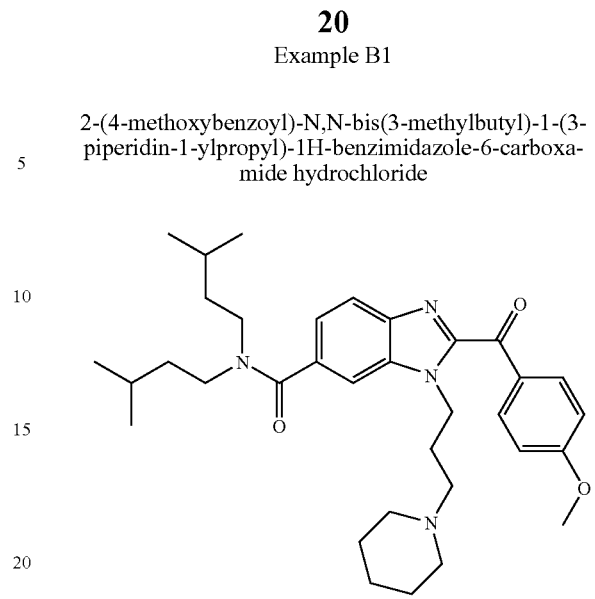

Manganese dioxide (500 mg) is added to a solution of 2-(4-methoxybenzyl)-N,N-bis(3-methylbutyl)-1-(3-piperidin-1-ylpropyl)-1H-benzimidazole-6-carboxamide (171 mg, prepared according to Example A2) in 1,4 dioxane (5 ml). The mixture is heated at 70° C. for 24 hours then a new portion of manganese dioxide (500 mg) is added. After stirring for another 24 hours at 70° C., a portion of manganese dioxide (500 mg) is again added and stirring at 70° C. is continued for another 24 hours then the mixture is cooled down to ambient temperature, concentrated under reduced pressure and filtered on celite. The filtrate is concentrated under reduced pressure at 40° C. in order to produce the expected compound in the form of the free base. The corresponding hydrochloride salt is formed by the addition of a 1N solution of hydrochloric acid in diethyl ether. The precipitate obtained is filtered, washed with diethyl ether then recrystallized from a dichloromethane/diethyl ether mixture and dried in order to produce the expected hydrochloride compound (50 mg, 26% yield).

MS/LC: Calculated MM=560.8; m/z=561.4 (MH+)

NMR $^1$H (400 MHz, DMSO-$d_6$): δ 0.65 (d, 6H), 0.95 (d, 6H), 1.25-1.79 (m, 12H), 2.28 (m, 2H), 2.82 (m, 2H), 3.16 (m, 4H), 3.32-3.48 (m, 4H), 3.89 (s, 3H), 4.61 (t, 2H), 7.13 (AB, 2H), 7.30 (AB, 1H), 7.89 (AB, 1H), 8.33 (AB, 2H), 10.48 (s, 1H).

According to reaction diagram B and in a manner analogous to the procedure described for the synthesis of 2-(4-methoxybenzoyl)-N,N-bis(3-methylbutyl)-1-(3-piperidin-1-ylpropyl)-1H-benzimidazole-6-carboxamide hydrochloride, the following compounds were prepared:

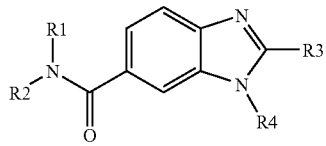

in which $R_1R_2N$ represents one of the radicals below:

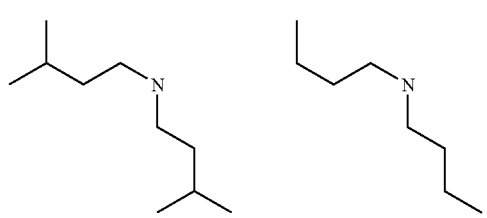

-continued

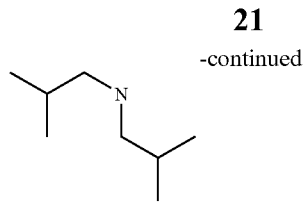

R₃ represents one of the radicals below:

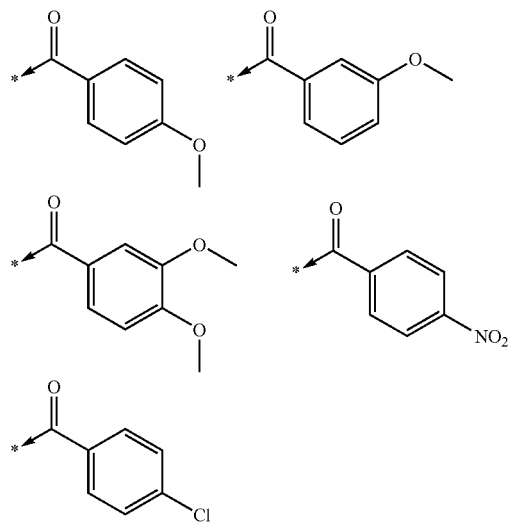

and R₄ represents the radical below:

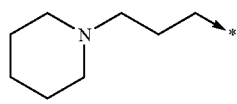

C. Preparation According to Reaction Diagram C

The compounds of formula I according to the invention in which A represents —CH₂— can be prepared according to the following diagram C:

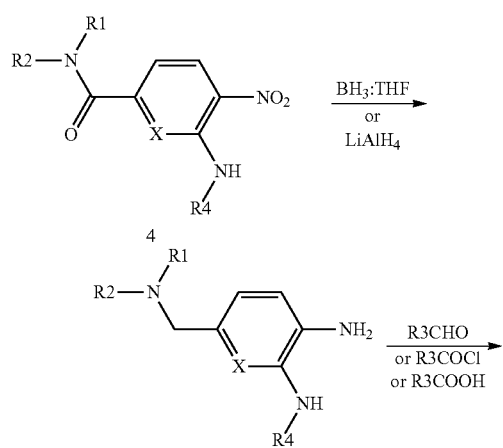

-continued

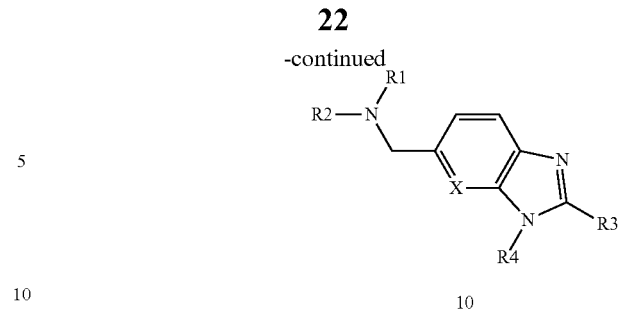

As described in diagram C, the derivative (4) prepared according to reaction diagram A, can be reduced to compound (9) using borane or lithium aluminium hydride in an aprotic solvent such as tetrahydrofuran or diethyl ether at a temperature of 0 to 70° C., for 3 to 24 hours. The dianiline (9) can then be treated by an aldehyde in the presence of an oxidizing agent such as nitrobenzene, at a temperature of 60-140° C. for 2 to 24 hours in an aprotic solvent such as dimethylformamide, in order to produce benzimidazole (10). Alternatively, the derivative (9) can react either with an acid chloride, or with a carboxylic acid in the presence of a coupling agent such as diisopropylcarbodiimide (DIC), dicyclohexylcarbodiimide (DCC), 1-(3-dimethylaminopropyl)-3-ethylcarbodiimide hydrochloride (EDC), carbonyldiimidazole (CDI), 2-(1H-benzotriazole-1-yl)-1,1,3,3-tetramethyluronium hexafluorophosphate (HBTU), 2-(1H-benzotriazole-1-yl)-1,1,3,3-tetramethyluronium tetrafluoroborate (TBTU) or O-(7-azobenzotriazol-1-yl)-1,1,3,3-tetramethyluronium hexafluorophosphate (HATU) in an inert organic solvent such as methylene chloride, tetrahydrofuran or dimethylformamide at ambient temperature for 3 to 24 hours in order to produce the corresponding amide.

The amide thus obtained produces benzimidazole (10) by treatment with an acid, such as acetic acid, hydrochloric acid, polyphosphoric acid at a temperature of 20-100° C. for 2 to 24 hours. The derivative (9) can also react with an imidate ester or a chloroacetamide derivative in an inert organic solvent such as dimethylformamide at a temperature of 20-100° C. for 3 to 24 hours in order to produce the benzimidazole derivative (10).

Preparation According to Reaction Diagram C':

The compounds (10) can also be prepared according to the following diagram C':

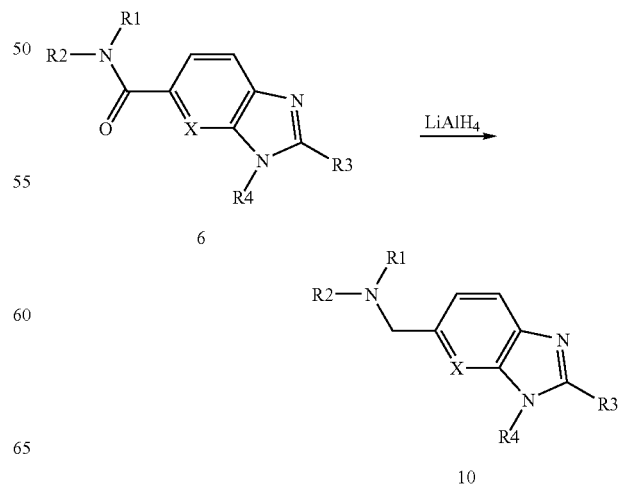

As described in diagram C', the amide (6) prepared according to reaction diagram A, can be reduced to the corresponding amine (10) using borane or lithium aluminium hydride in an aprotic solvent such as tetrahydrofuran or diethyl ether at a temperature of 0 to 70° C., for 1 to 6 hours.

Example C1 methyl 4-[6-{[bis(3-methylbutyl)amino]methyl}-1-(3-piperidin-1-ylpropyl)-1H-benzimidazol-2-yl]benzoate dihydrochloride

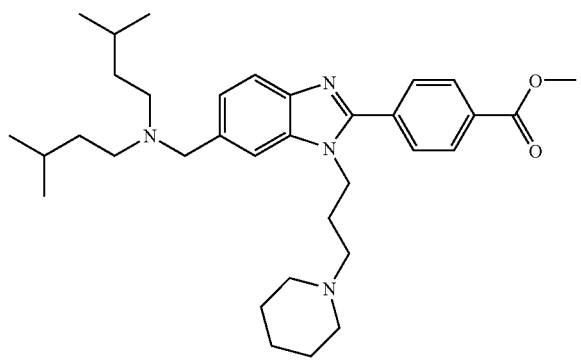

Stage 1

4-{[bis(3-methylbutyl)amino]methyl}-$N^2$-(3-piperidin-1-ylpropyl)benzene-1,2-diamine A solution of lithium aluminium hydride (36 ml; 1N in THF) is added dropwise to a solution of N,N-bis(3-methylbutyl)-4-nitro-3-[(3-piperidin-1-ylpropyl)amino]benzamide (1.6 g) cooled down to 0° C. The mixture is taken to a temperature of 20° C. then heated under reflux for 6 hours and hydrolyzed with water cooled down to 0° C. followed by a 1N soda solution. After the addition of dichloromethane, the mixture is filtered on celite. After decantation of the filtrate and extractions, the combined organic phases are washed with 1N soda then with salt water, dried over $Na_2SO_4$ and concentrated under reduced pressure at 40° C. in order to produce the expected compound in the form of an oil (1.23 g, 85% yield).

MS/LC: Calculated MM=402.7; m/z=403.3 (MH+)

NMR $^1$H (400 MHz, DMSO-$d_6$): δ 0.81 (d, 12H), 1.28 (m, 4H), 1.38 (m, 2H), 1.48 (m, 6H), 1.71 (m, 2H), 2.31 (m, 10H), 3.01 (m, 2H), 3.29 (m, 2H), 4.28 (m, 2H), 4.6 (m, 1H), 6.30 (AB, 1H), 6.38 (s, 1H), 6.43 (AB, 1H).

Stage 2

Methyl 4-[6-{[bis(3-methylbutyl)amino]methyl}-1-(3-piperidin-1-ylpropyl)-1H-benzimidazol-2-yl]benzoate dihydrochloride Methyl-4-formylbenzoate (33 mg, 1 eq) is added to a solution of 4-{[bis(3-methylbutyl)amino]methyl}-$N^2$-(3-piperidin-1-ylpropyl)benzene-1,2-diamine (80 mg) in nitrobenzene (2 ml). The mixture is heated at 130° C. for 18 hours. Purification of the mixture by flash chromatography on silica gel (eluent: 100% dichloromethane to dichloromethane/methanol 7:3) produces the expected compound in the form of the free base. The corresponding hydrochloride salt is formed by the addition of a 1N solution of hydrochloric acid in diethyl ether. The precipitate obtained is filtered and dried in order to produce the expected monohydrochloride compound (47 mg, 41% yield).

MS/LC: Calculated MM=546.8; m/z=547.3 (MH+)

NMR $^1$H (400 MHz, DMSO-$d_6$): δ 0.86 (m, 12H), 1.21-1.75 (m, 12H), 2.36 (m, 2H), 2.81 (m, 2H), 3.05 (m, 6H), 3.91 (s, 3H), 4.33 (m, 2H), 4.47 (d, 2H), 7.46 (AB, 1H), 7.79 (AB, 1H), 7.98 (AB, 1H), 8.16 (AB, 1H), 8.36 (s, 1H), 10.18 (s, 1H), 10.73 (s, 1H).

According to reaction diagram C and in a manner analogous to the procedure described for the synthesis of methyl 4-[6-{[bis(3-methylbutyl)amino]methyl}-1-(3-piperidin-1-ylpropyl)-1H-benzimidazol-2-yl]benzoate dihydrochloride, the following compounds were prepared:

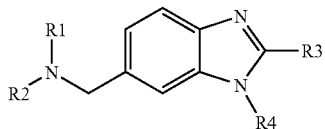

in which $R_1R_2N$ represents one of the radicals below:

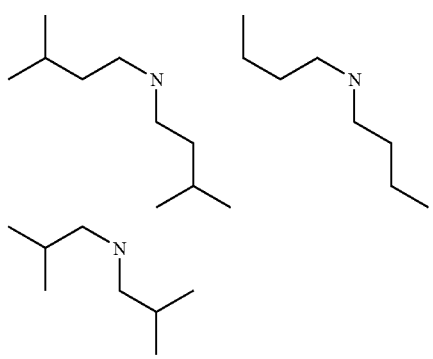

$R_3$ represents one of the radicals below:

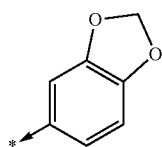

1 or more substitutions chosen from:

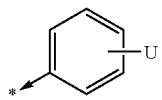

U=H, F, Cl, Br, I, $NO_2$, OMe, SMe, Me, Et, iPr, tBu, $CF_3$, $OCF_3$, C(O)OMe, C(O)OEt, C(O)Me, C(O)Et, C(O)NHMe, C(O)$NH_2$

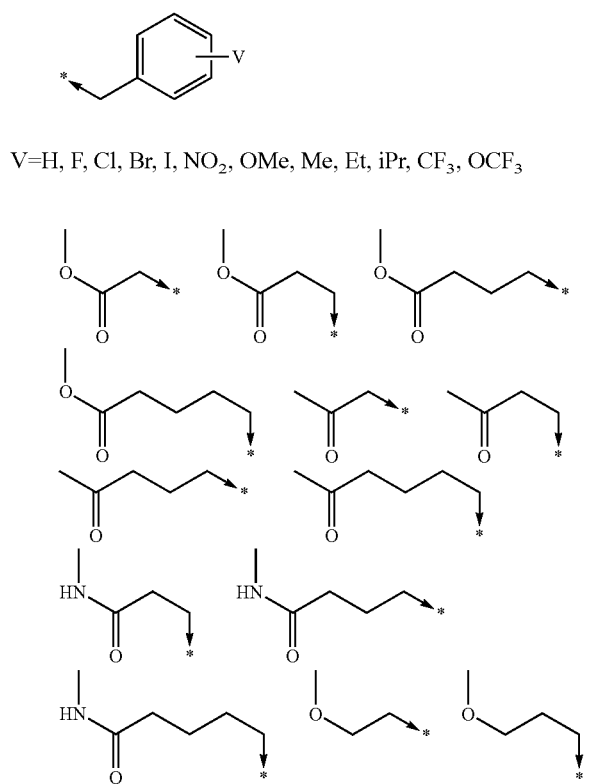
V=H, F, Cl, Br, I, NO₂, OMe, Me, Et, iPr, CF₃, OCF₃
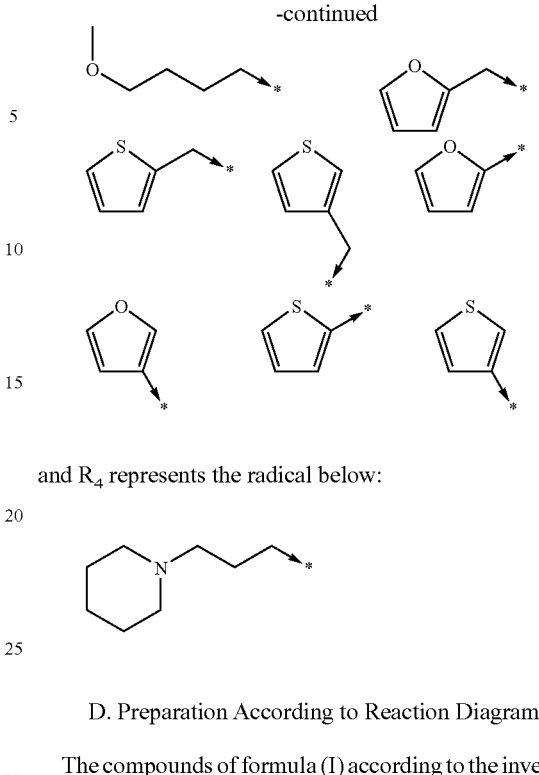
and R₄ represents the radical below:
D. Preparation According to Reaction Diagram D
The compounds of formula (I) according to the invention in which A represents —C(O)—C(R$_a$)(R$_b$)—, can be prepared according to the following diagram D:
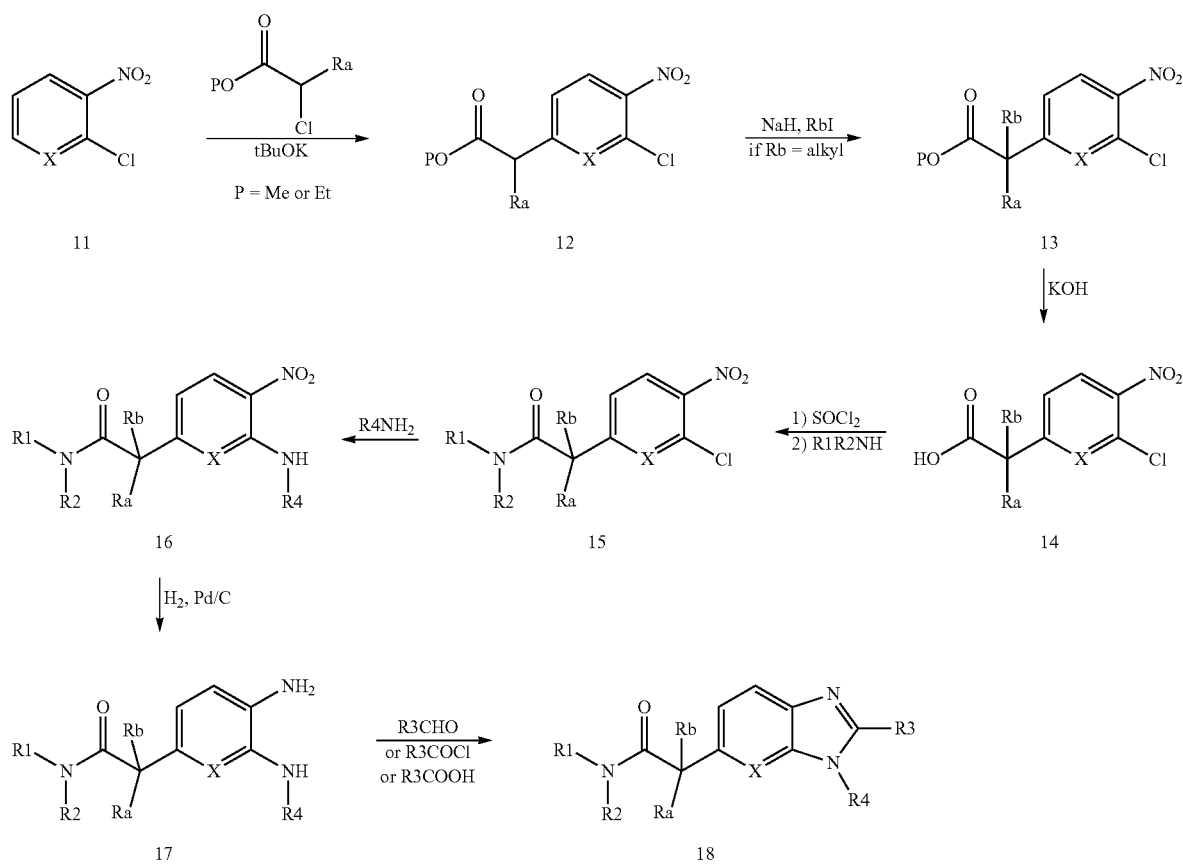

As described in diagram D, the derivative (11) can be alkylated in the presence of a strong base such as potassium tertbutylate, by an α-chloroester derivative, in a polar aprotic solvent such as dimethylformamide at a temperature of 0-20° C. for 0.5-2 hours, in order to produce compound (12). The derivative (13) can be optionally alkylated in the presence of a strong base such as sodium hydride and an alkylating agent such as an alkyl iodide in an aprotic solvent such as dimethylformamide at a temperature of 0-20° C. for 1-4 hours, in order to produce the compound (13). The ester (13) can be saponified in the presence of an inorganic base such as lithium or potassium hydroxide in a mixture of polar solvents such as water and methanol at a temperature of 20-80° C. for 1-6 hours. The resulting carboxylic acid (14) can be coupled with a primary or secondary amine in the presence of a coupling agent such as diisopropylcarbodiimide (DIC), dicyclohexylcarbodiimide (DCC), 1-(3-dimethylaminopropyl)-3-ethylcarbodiimide hydrochloride (EDC) or carbonyldiimidazole (CDI), with or without 1-hydroxybenzotriazole (HOBt) in an inert organic solvent such as methylene chloride, tetrahydrofuran or dimethylformamide at a temperature of approximately 20° C. for 3 to 24 hours. Alternatively the acid (14) can be treated with thionyl or oxalyl chloride in an aprotic solvent such as dichloromethane or toluene at a temperature of 40-60° C. for 2-16 hours then the acid chloride thus obtained can react with a primary or secondary amine, in the presence of a tertiary base such as triethylamine, diisopropylethylamine in an aprotic solvent such as dichloromethane or tetrahydrofuran at a temperature of 0-20° C. for 0.5-4 hours in order to produce the amide (15). Treatment of the fluorinated or chlorinated derivative (15) by a primary amine in the presence of an inorganic base such as cesium or potassium carbonate in an inert organic solvent such as dimethylformamide or acetonitrile at a temperature of 20-100° C. for 2 to 48 hours produces the derivative (16). The nitro function of the compound (16) is reduced by treatment with dihydrated stannous chloride in an inert solvent such as ethyl acetate or dimethylformamide at a temperature of 60-80° C. for 3 to 15 hours, or by catalytic hydrogenation in the presence of 10% palladium on carbon in an inert solvent such as methanol, ethanol, ethyl acetate or a mixture of these solvents, at a temperature of 18-25° C., for 2 to 8 hours in order to produce dianiline (17). The dianiline (17) can then be treated by an aldehyde in the presence of an oxidizing agent such as nitrobenzene, or DDQ in an aprotic solvent such as dimethylformamide, at a temperature of 60-140° C. for 2 to 24 hours in order to produce benzimidazole (18). Alternatively, the derivative (17) can react either with an acid chloride, or with a carboxylic acid in the presence of a coupling agent such as diisopropylcarbodiimide (DIC), dicyclohexylcarbodiimide (DCC), 1-(3-dimethylaminopropyl)-3-ethylcarbodiimide hydrochloride (EDC), carbonyldiimidazole (CDI), 2-(1H-benzotriazole-1-yl)-1,1,3,3-tetramethyluronium hexafluorophosphate (HBTU), 2-(1H-benzotriazole-1-yl)-1,1,3,3-tetramethyluronium tetrafluoroborate (TBTU) or O-(7-azobenzotriazol-1-yl)-1,1,3,3-tetramethyluronium hexafluorophosphate (HATU) in an inert organic solvent such as methylene chloride, tetrahydrofuran or dimethylformamide at ambient temperature for 3 to 24 hours in order to produce the corresponding amide. The amide thus obtained produces benzimidazole (18) by treatment with an acid, such as acetic acid, hydrochloric acid, polyphosphoric acid at a temperature of 20-100° C. for 2 to 24 hours. The derivative (17) can also react with an imidate ester or a chloroacetamide derivative in an inert organic solvent such as dimethylformamide at a temperature of 20-100° C. for 3 to 24 hours in order to produce the benzimidazole derivative (18).

Example D1

N,N-diisobutyl-2-[2-(4-methoxyphenyl)-1-(3-piperidin-1-ylpropyl)-1H-benzimidazol-6-yl]-2-methylpropanamide

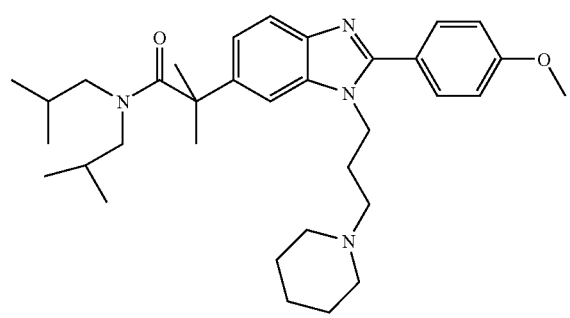

Stage 1 ethyl 2-(3-chloro-4-nitrophenyl)propanoate

Potassium tert-butylate (11.22 g, 2 eq) is added to a solution of DMF (80 ml) cooled down to 0° C. A solution of 1-chloro-2-nitrobenzene (7.87 g, 1 eq) and ethyl 2-chloropropanoate (7 ml, 1.1 eq) is added dropwise over 45 minutes to the mixture keeping the reaction temperature below 5° C. At the end of the addition, stirring is maintained for 2 hours at 0° C. then the mixture is hydrolyzed at this temperature by a 1N hydrochloric acid solution and ethyl acetate is added. After decantation and extractions, the combined organic phases are washed with salt water, dried over $Na_2SO_4$ and concentrated under reduced pressure. Purification by flash chromatography on silica gel (eluent: heptane/dichloromethane 8:2 to 6:4) produces the expected compound in the form of a yellow oil (8.28 g; 64% yield).

NMR $^1$H (400 MHz, DMSO-$d_6$): δ 1.14 (t, 3H), 1.42 (d, 3H), 3.99 (q, 1H), 4.08 (m, 2H), 7.52 (AB, 1H), 7.71 (s, 1H), 8.05 (AB, 1H).

Stage 2 ethyl 2-(3-chloro-4-nitrophenyl)-2-methylpropanoate

A solution of ethyl 2-(3-chloro-4-nitrophenyl)propanoate (14.1 g) is added dropwise to a suspension of sodium hydride (60% in oil, 2.4 g, 1.1 eq) in DMF (15 ml), cooled down to 0° C. After stirring for 1 hour at this temperature, a solution of methyl iodide (3.72 ml, 1.1 eq) in DMF (40 ml) is added dropwise to the mixture. Stirring is continued for 3 hours at ambient temperature. The reaction medium is cooled down to 0° C. then ethyl acetate, water saturated with sodium hydrogen carbonate, then water are added dropwise. After decantation and extractions, the combined organic phases are washed with salt water, dried over $Na_2SO_4$ and concentrated under reduced pressure in order to produce the expected compound in the form of an oil which crystallizes. The crystals are washed with heptane and dried (13.8 g; 94% yield).

NMR $^1$H (400 MHz, DMSO-$d_6$): δ 1.12 (t, 3H), 1.54 (s, 6H), 4.09 (q, 1H), 7.50 (AB, 1H), 7.66 (s, 1H), 8.04 (AB, 1H).

Stage 3

2-(3-chloro-4-nitrophenyl)-2-methylpropanoic acid

A 2N potassium hydroxide solution (18 ml) is added to a solution of ethyl 2-(3-chloro-4-nitrophenyl)-2-methylpropanoate (1 g) in methanol (20 ml) at a temperature of approximately 20° C. The mixture is then heated at 80° C. for 1.5 hours then cooled down to ambient temperature. The methanol is evaporated off by concentration of the mixture under reduced pressure. The remaining aqueous phase is washed with dichloromethane then cooled down to 0° C. and acidified by acetic acid. After the addition of dichloromethane, decantation and extractions, the combined organic phases are washed with salt water, dried over $Na_2SO_4$ and concentrated under reduced pressure in order to produce the expected compound in the form of an oil which crystallizes (852 mg, 95% yield).

NMR $^1$H (400 MHz, DMSO-$d_6$): δ 1.52 (s, 6H), 7.53 (AB, 1H), 7.66 (s, 1H), 8.04 (AB, 1H), 12.72 (s, 1H).

Stage 4

2-(3-chloro-4-nitrophenyl)-N,N-diisobutyl-2-methylpropanamide

Thionyl chloride (0.54 ml, 4 eq) is added to a solution of 2-(3-chloro-4-nitrophenyl)-2-methylpropanoic acid (500 mg) in dichloromethane (1 ml). The mixture is heated under reflux for 16 hours then cooled down to ambient temperature. The solvent is evaporated off under reduced pressure at 40° C. (co-evaporation with toluene). Diisopropylethylamine (0.42 ml, 1.2 eq) and the diisobutylamine (0.36 ml, 1 eq) are successively added to a solution of the acid chloride thus obtained in dichloromethane (1 ml), cooled down to 0° C. At the end of the addition, stirring is continued for 3 hours at ambient temperature then the mixture is concentrated under reduced pressure at 40° C. The residue is dissolved in ethyl ether and the organic phase is washed successively with 1N soda, a saturated sodium hydrogen carbonate solution, salt water than dried over $Na_2SO_4$ and concentrated under reduced pressure at 40° C. Purification by flash chromatography on silica gel (eluent: heptane/ethyl acetate 8:2 to 7:3) produces the expected compound in the form of an oil which crystallizes (0.585 g; 82% yield).

MS/LC: Calculated MM=354.9; m/z=355.2 (MH+)
NMR $^1$H (400 MHz, CDCl$_3$): δ 0.58 (d, 6H), 0.90 (d, 6H), 1.58 (m, 6H), 1.74 (m, 1H), 1.95 (m, 1H), 2.65 (d, 2H), 3.27 (d, 2H), 7.30 (AB, 1H), 7.44 (s, 1H), 7.91 (AB, 1H).

Stage 5

N,N diisobutyl-2-methyl-2-{4-nitro-3-[(3-piperidin-1-ylpropyl)amino]phenyl}propanamide A mixture of 2-(3-chloro-4-nitrophenyl)-N,N-diisobutyl-2-methylpropanamide (2.39 g), 3-piperidino-propylamine (1.9 g, 2 eq) and potassium carbonate (1.8 g, 2 eq) in DMF (40 ml) is heated at 100° C. for 24 hours then cooled down to ambient temperature. Water and ethyl acetate are added to the medium. After decantation and extractions, the combined organic phases are washed with salt water, dried over $Na_2SO_4$ and concentrated under reduced pressure. Purification of the residue obtained by flash chromatography on silica gel (eluent: dichloromethane 100% to dichloromethane/methanol 6:4) produces the expected compound in the form of a yellow oil (1.6 g, 51% yield).

MS/LC: Calculated MM=460.7; m/z=461.4 (MH+)
NMR $^1$H (400 MHz, CDCl$_3$): δ 0.57 (d, 6H), 0.89 (d, 6H), 1.50 (m, 2H), 1.56 (m, 6H), 1.63 (m, 4H), 1.77 (m, 1H), 1.89 (m, 3H), 2.43 (m, 6H), 2.75 (d, 2H), 3.29 (d, 2H), 3.32 (m, 2H), 6.58 (AB, 1H), 6.67 (s, 1H), 8.15 (AB, 1H), 8.29 (t, 1H).

Stage 6

2-{4-amino-3-[(3-piperidin-1-ylpropyl)amino]phenyl}-N,N-diisobutyl-2-methylpropanamide N,N-diisobutyl-2-methyl-2-{4-nitro-3-[(3-piperidin-1-ylpropyl)amino]phenyl}propanamide (1.6 g) in solution in a mixture of ethyl acetate/ethanol 2:1 (100 ml) and 10% palladium on carbon (160 mg) are introduced into an autoclave. After stirring for 4 hours under a hydrogen atmosphere (3 bars) at a temperature of approximately 20° C., the catalyst is eliminated by filtration on celite and the filtrate is concentrated under reduced pressure at 40° C. in order to produce the expected compound in the form of an oil (1.4 g, 94% yield).

MS/LC: Calculated MM=430.7; m/z=431.4 (MH+)
NMR $^1$H (400 MHz, CDCl$_3$): δ 0.45 (d, 6H), 0.79 (d, 6H), 1.35 (m, 8H), 1.49 (m, 4H), 1.70 (m, 3H), 1.85 (m, 1H), 1.89 (m, 3H), 2.33 (m, 6H), 2.79 (d, 2H), 2.97 (t, 2H), 3.11 (m, 2H), 4.45 (m, 2H), 6.18 (s, 1H), 6.30 (AB, 1H), 6.48 (AB, 1H).

Stage 7

N,N-diisobutyl-2-[2-(4-methoxyphenyl)-1-(3-piperidin-1-ylpropyl)-1H-benzimidazol-6-yl]-2-methylpropanamide hydrochloride A mixture of 2-{4-amino-3-[(3-piperidin-1-ylpropyl)amino]phenyl}-N,N-diisobutyl-2-methylpropanamide (34 mg) and p-anisaldehyde (13 mg) in nitrobenzene (1 ml) is heated at 120° C. for 24 hours then cooled down to ambient temperature. Purification of the mixture by flash chromatography on silica gel (eluent: dichloromethane 100% to dichloromethane/methanol 85:15) produces the expected compound in the form of the free base. The corresponding hydrochloride salt is formed by the addition of a 1N solution of hydrochloric acid in diethyl ether. The precipitate obtained is filtered, washed with diethyl ether and dried in order to produce the expected monohydrochloride compound (12 mg, 60% yield).

MS/LC: Calculated MM=546.8; m/z=547.4 (MH+)
NMR $^1$H (400 MHz, CDCl$_3$): δ 0.44 (d, 6H), 0.83 (d, 6H), 1.30 (m, 2H), 1.58 (s, 6H), 1.71 (m, 6H), 2.18 (m, 2H), 2.72 (m, 4H), 3.01 (m, 2H), 3.21 (m, 4H), 3.89 (s, 3H), 4.54 (t, 2H), 7.23 (AB, 2H), 7.28 (m, 1H), 7.76 (AB, 1H); 7.86 (m, 3H), 10.41 (s, 1H).

According to reaction diagram D and in a manner analogous to the procedure described for the synthesis of N,N-diisobutyl-2-[2-(4-methoxyphenyl)-1-(3-piperidin-1-ylpropyl)-1H-benzimidazol-6-yl]-2-methylpropanamide hydrochloride, the following compounds were prepared:

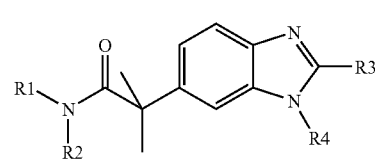

in which $R_1R_2N$ represents one of the radicals below:

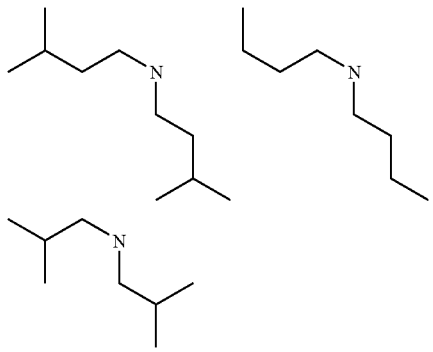

$R_3$ represents one of the radicals below:

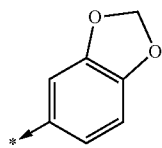

1 or more substitutions chosen from:

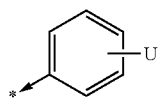

U=H, F, Cl, Br, I, $NO_2$, OMe, Me, Et, iPr, tBu, $CF_3$, $OCF_3$, C(O)OMe,

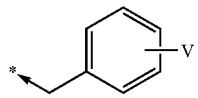

V=H, $NO_2$, OMe

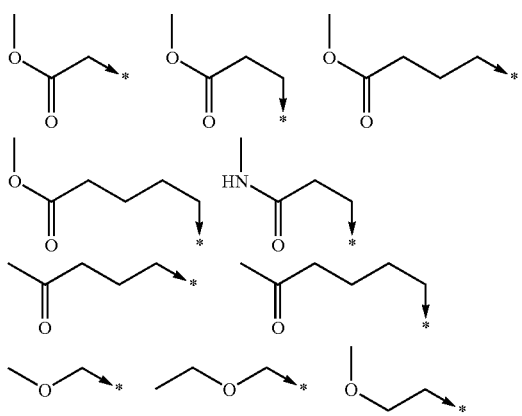

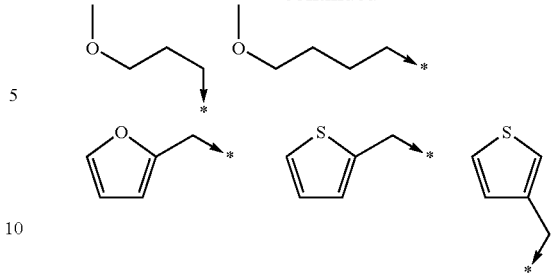

and $R_4$ represents one of the radicals below:

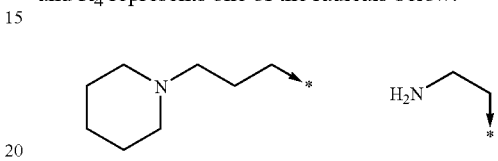

A subject of the present application is also a process for preparing a compound of formula (I) as defined above, characterized in that the compound of general formula:

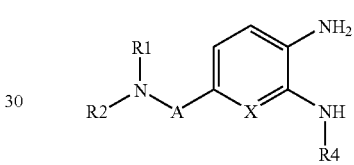

in which A, X, $R_1$, $R_2$, $R_4$ have the meaning indicated above, is treated i) either by an aldehyde of general formula $R_3CHO$ in which $R_3$ has the meaning indicated above, in the presence of an oxidizing agent;

ii) or by an acid chloride of general formula $R_3CHO$ in which $R_3$ has the meaning indicated above, in the presence of an acid;

iii) or by a carboxylic acid of general formula $R_3C(O)OH$ in which $R_3$ has the meaning indicated above, in the presence of a coupling agent followed by treatment of the amide thus formed by an acid.

iv) or by a chloroacetamide derivative of general formula $Z''_3$—NH—C(O)CH$_2$Cl in which $Z''_3$ has the meaning indicated above, in the presence of a tertiary base and sulphur.

During treatment by the aldehyde $R_3CHO$, the oxidizing agent used can be for example nitrobenzene. During treatment by an acid chloride $R_3CHO$, the acid used can be acetic acid. Similarly, during treatment by the carboxylic acid $R_3C(O)OH$, then the treatment of the amide thus formed, the acid used can be acetic acid.

A subject of the invention is also a compound of general formula (I)

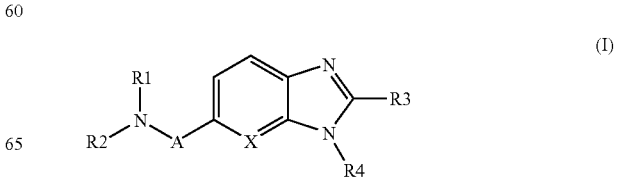

in racemic, enantiomeric form or any combinations of these forms and in which:

A represents —$CH_2$—, —$C(O)$—, —$C(O)$—$C(R_a)(R_b)$—;
X represents —CH— or a nitrogen atom;
$R_a$ and $R_b$ represent, independently, the hydrogen atom or a ($C_1$-$C_6$)alkyl radical;
$R_1$ represents the hydrogen atom or a ($C_1$-$C_8$)alkyl radical;
$R_2$ represents a ($C_1$-$C_8$)alkyl radical;
or $R_1$ and $R_2$ form together, with the nitrogen atom to which they are attached, a heterobicycloalkyl or a heterocycloalkyl optionally substituted by one or more identical or different ($C_1$-$C_6$)alkyl substituents;
$R_3$ represents —$(CH_2)_p$—$Z_3$, —$C(O)$—$Z'_3$, —$CH(OH)$—$Z'_3$ or —$C(O)$—$NH$—$Z''_3$;
  $Z_3$ represents a ($C_1$-$C_6$)alkyl, ($C_1$-$C_6$)alkoxy, ($C_1$-$C_6$)alkyl-carbonyl, ($C_1$-$C_6$)alkoxy-carbonyl, ($C_1$-$C_6$)alkyl-aminocarbonyl, ($C_3$-$C_7$)cycloalkyl, heterocycloalkyl, aryl or heteroaryl radical,
  the ($C_3$-$C_7$)cycloalkyl and heterocycloalkyl radicals being optionally substituted by one or more identical or different radicals chosen from ($C_1$-$C_6$)alkyl and oxy;
  the aryl radical being optionally substituted by one or more identical or different substituents chosen from: halo, nitro or —$(CH_2)_p$-$V_3$—$Y_3$;
  $V_3$ represents —O—, —S—, —$C(O)$—, —$C(O)$—O—, —$NH$—$C(O)$—, —$C(O)$—$NR'_3$—, —$NH$—$C(O)$—$NR'_3$— or a covalent bond; —
  $Y_3$ represents the hydrogen atom or a ($C_1$-$C_6$)alkyl radical optionally substituted by one or more identical or different halo radicals;
  or $Z_3$ represents a radical of formula

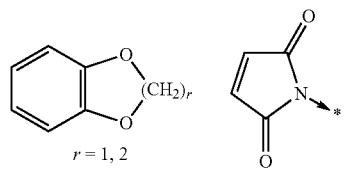

r = 1, 2

$Z'_3$ represents an aryl radical optionally substituted by one or more identical or different substituents chosen from: halo, nitro and —$(CH_2)_{p'}$-$V'_3$—$Y'_3$;
$V'_3$ represents —O—, —$C(O)$—, —$C(O)$—O—, —$NH$—$C(O)$—, —$C(O)$—$NR'_3$— or a covalent bond;
$Y'_3$ represents the hydrogen atom or a ($C_1$-$C_6$)alkyl radical optionally substituted by one or more identical or different halo radicals;
$R'_3$ represents the hydrogen atom, a ($C_1$-$C_6$)alkyl or ($C_1$-$C_6$)alkoxy radical;
$Z''_3$ represents the hydrogen atom or an -$A_3$-$C(O)$—O—(($C_1$-$C_6$)alkyl), -$A_3$-$C(O)$—$NH$—(($C_1$-$C_6$)alkyl) or -$A_3$-$O$—(($C_1$-$C_6$)alkyl) radical;
$A_3$ represents a linear or branched hydrocarbon chain containing 1 to 6 carbon atoms, or an arylene radical;
p, p' and p" represent, independently, an integer from 0 to 4;
$R_4$ represents a radical of formula —$(CH_2)_n$—$R'_4$;
$R'_4$ represents a heterocycloalkyl containing at least one nitrogen atom and optionally substituted by ($C_1$-$C_6$)alkyl; a heteroaryl containing at least one nitrogen atom and optionally substituted by ($C_1$-$C_6$)alkyl; or a radical of formula —$NW_4W'_4$;
  $W_4$ represents the hydrogen atom or ($C_1$-$C_8$)alkyl;
  $W'_4$ represents a radical of formula —$(CH_2)_s$—$Z_4$ in which $Z_4$ represents the hydrogen atom, a ($C_1$-$C_8$)alkyl or ($C_3$-$C_7$)cycloalkyl radical;
  s and s' represent, independently, an integer from 0 to 6; or a pharmaceutically acceptable salt of the latter.

Preferably, the invention relates to compounds of formula I as defined above and characterized in that $R_1$ represents the hydrogen atom or a ($C_1$-$C_8$)alkyl radical, and $R_2$ represents a ($C_1$-$C_8$)alkyl radical; or a pharmaceutically acceptable salt of the latter.

The invention preferably also relates to compounds of formula I as defined above and characterized in that X represents —CH—; or a pharmaceutically acceptable salt of the latter.

Preferentially, the invention also relates to compounds of formula I as defined above and characterized in that A represents —$CH_2$—; or a pharmaceutically acceptable salt of the latter.

Preferentially, the invention also relates to compounds of formula I as defined above and characterized in that A represents —$C(O)$—$C(R_a)(R_b)$— and $R_a$ and $R_b$ represent, independently, the methyl radical; or a pharmaceutically acceptable salt of the latter.

Preferentially also, the invention relates to compounds of formula I as defined above and characterized in that A represents —$C(O)$—; or a pharmaceutically acceptable salt of the latter.

Very preferentially, the invention relates to compounds of formula I as defined above and characterized in that
  $R_4$ represents a radical of formula —$(CH_2)_n$—$R'_4$;
  $R'_4$ represents a heterocycloalkyl containing at least one nitrogen atom chosen from piperidine and pyrrolidine, heterocycle optionally substituted by ($C_1$-$C_6$)alkyl; or a radical of formula —$NW_4W'_4$;
  $W_4$ represents the hydrogen atom or ($C_1$-$C_8$)alkyl;
  $W'_4$ represents a radical of formula —$(CH_2)_s$—$Z_4$ in which $Z_4$ represents the hydrogen atom or a ($C_1$-$C_8$) alkyl radical;
  s and s' represent, independently, an integer from 0 to 6; or a pharmaceutically acceptable salt of the latter.

Very preferentially also, the invention relates to compounds of formula I as defined above and characterized in that
$R_3$ represents —$(CH_2)_p$—$Z_3$ or —$C(O)$—$Z'_3$;
  $Z_3$ represents a ($C_1$-$C_6$)alkoxy, ($C_1$-$C_6$)alkyl-carbonyl, ($C_1$-$C_6$)alkoxy-carbonyl, ($C_1$-$C_6$)alkyl-aminocarbonyl, aryl or heteroaryl radical,
  the aryl radical being optionally substituted by one or more identical or different substituents of formula —$(CH_2)$p-$V_3$—$Y_3$;
  $V_3$ represents —O—, —$C(O)$—, —$C(O)$—O— or —$C(O)$—$NH$—;
  $Y_3$ represents a ($C_1$-$C_6$)alkyl radical;
  $Z'_3$ represents an aryl radical optionally substituted by one or more identical or different substituents of formula —$(CH_2)_p$"-$V'_3$—$Y'_3$;
  $V'_3$ represents —O—;
  $Y'_3$ represents a ($C_1$-$C_6$)alkyl radical;
  p, p' and p" represent, independently, an integer from 0 to 4; or a pharmaceutically acceptable salt of the latter;
and more particularly the aryl radical is the phenyl radical and the heteroaryl radical is chosen from thienyl and furyl.

The compounds I of the present invention possess useful pharmacological properties. Thus it has been discovered that the compounds I of the present invention possess a good affinity for certain subtypes of melanocortin receptors, in particular MC4 receptors.

The compounds of the present invention can thus be used in different therapeutic applications. They can advantageously be used for treating pathological states or metabolic diseases, of the nervous or dermatological system in which one or more melanocortin receptors are involved such as: inflammatory states, energy homeostasis, food intake disorders, weight disorders (obesity, cachexia, anorexia), sexual activity disorders (erectile disorders), neuropathic pain, and also mental disorders (anxiety, depression), drug addition, skin diseases (acne, dermatitis, cutaneous cancers, melanomas). They can also be used for stimulating nerve regeneration. An illustration of the pharmacological properties of the compounds of the invention will be found hereafter, in the experimental part.

A subject of the present application is also pharmaceutical compositions containing, as active ingredient, at least one product of formula I as defined above, as well as the pharmaceutically acceptable salts of said product of formula I, in combination with a pharmaceutically acceptable support.

By pharmaceutically acceptable salt, is meant in particular addition, salts of inorganic acids such as hydrochloride, hydrobromide, hydroiodide, sulphate, phosphate, diphosphate and nitrate or organic acids such as acetate, maleate, fumarate, tartrate, succinate, citrate, lactate, methanesulphonate, p-toluenesulphonate, pamoate and stearate. Salts formed from bases such as sodium or potassium hydroxide also fall within the scope of the present invention when they can be used. For other examples of pharmaceutically acceptable salts, reference can be made to "Salt selection for basic drugs", *Int. J Pharm.* (1986), 33, 201-217.

A subject of the present application is also the use of the compounds according to the present invention, for the preparation of a medicament for the treatment of weight disorders such as obesity, cachexia and anorexia, mental disorders such as anxiety and depression, neuropathic pain, sexual activity disorders such as erectile disorders.

The pharmaceutical composition can be in the form of a solid, for example, powders, granules, tablets, gelatin capsules or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or the glycols, as well as their mixtures, in varying proportions, in water, added to pharmaceutically acceptable oils or fats. The sterile liquid compositions can be used for intramuscular, intraperitoneal or subcutaneous injections and the sterile compositions can also be administered intravenously.

All the technical and scientific terms used in the present text have the meaning known to a person skilled in the art. Moreover, all the patents (or patent applications) as well as the other bibliographical references are incorporated by way of reference.

Experimental Part:

The compounds according to the invention obtained according to the procedures of examples A, B, C, C' and D described previously, are shown in the table below.

The compounds are characterized by their retention time (rt) and their molecular peak determined by mass spectrometry (MH+).

For mass spectrometry, a single quadrupole mass spectrometer (Micromass, Platform model) equipped with an electrospray source is used with a resolution of 0.8 Da at 50% valley. A calibration is carried out monthly between the masses 80 and 1000 Da using a calibrating mixture of sodium iodide and rubidium iodide in solution in an isopropanol/water mixture (1/1 Vol.).

For liquid chromatography, a Waters system including an in-line degasser, a Waters 600 quaternary pump, a Gilson 233 plate sampling injector and a Waters PAD 996 UV detector is used.

The elution conditions used are the following:
Eluent: A water+0.04% trifluoroacetic acid; B acetonitrile

| T (min) | A % | B % |
|---|---|---|
| 1 | 95 | 5 |
| 8.5 | 5 | 95 |
| 10.5 | 5 | 95 |
| 10.6 | 95 | 5 |
| 14.9 | 95 | 5 |
| 15.0 | 95 | 5 |

Flow rate: 1 ml/min; Injection: 10 μl; Column: Uptisphere ODS 3 μm 75*4.6 mm i.d. These examples are presented in order to illustrate the above procedures and should in no case be considered as a limit to the scope of the invention.

| Examples | Molecular Structures | [M & H]+ | rt (min) |
|---|---|---|---|
| 1 | 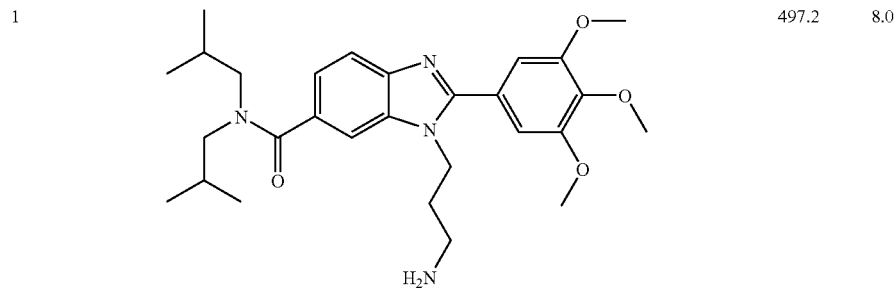 | 497.2 | 8.0 |
| 2 | 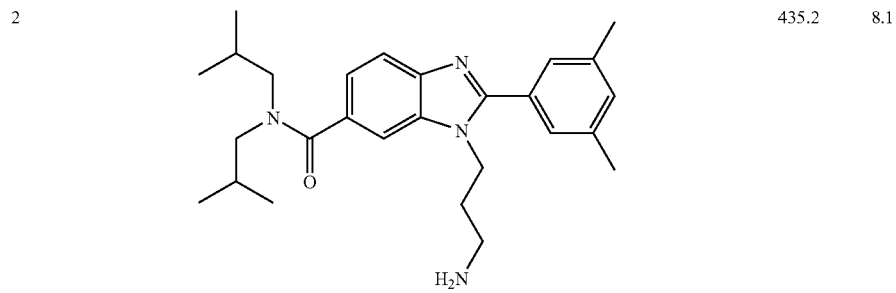 | 435.2 | 8.1 |

-continued

| Examples | Molecular Structures | [M & H]+ | rt (min) |
|---|---|---|---|
| 3 | 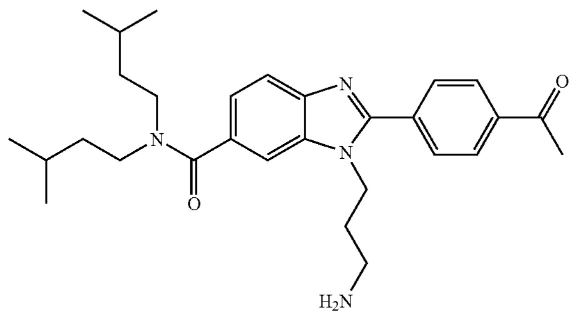 | 477.2 | 8.6 |
| 4 | 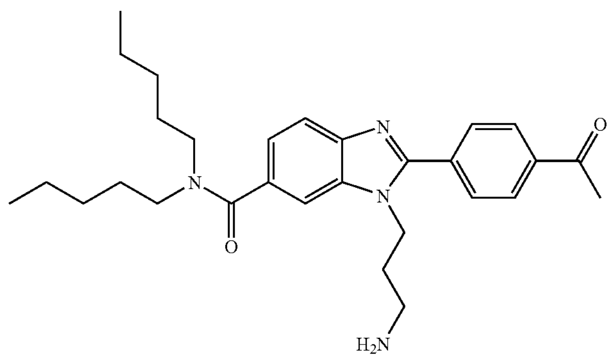 | 477.3 | 8.6 |
| 5 | 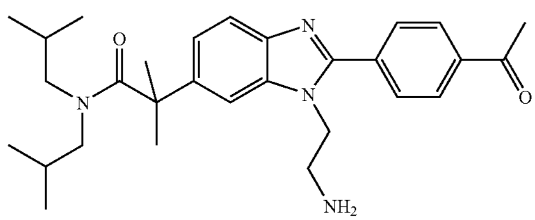 | 477.3 | 7.7 |
| 6 | 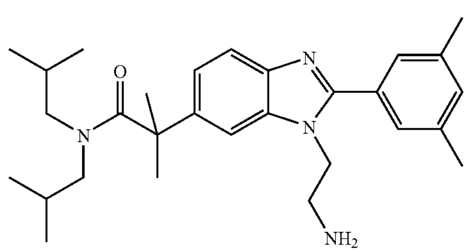 | 463.3 | 7.6 |
| 7 | 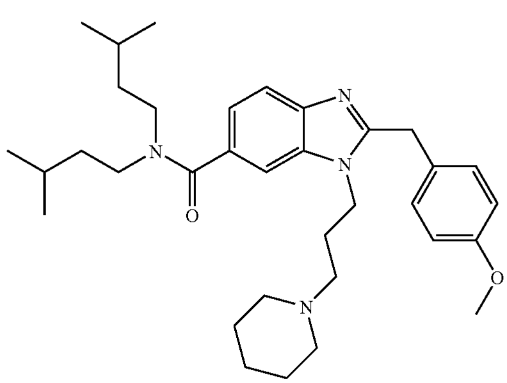 | 547.5 | 8.5 |

-continued

| Examples | Molecular Structures | [M & H]+ | rt (min) |
| --- | --- | --- | --- |
| 8 | 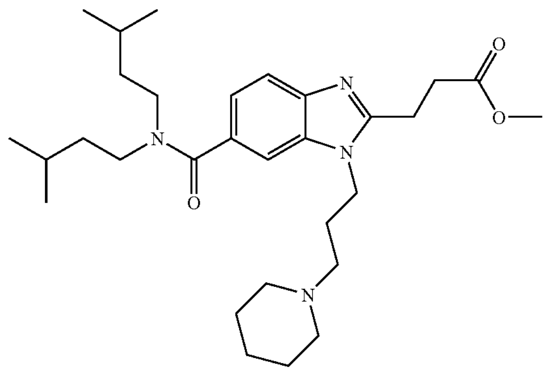 | 513.5 | 8.3 |
| 9 | 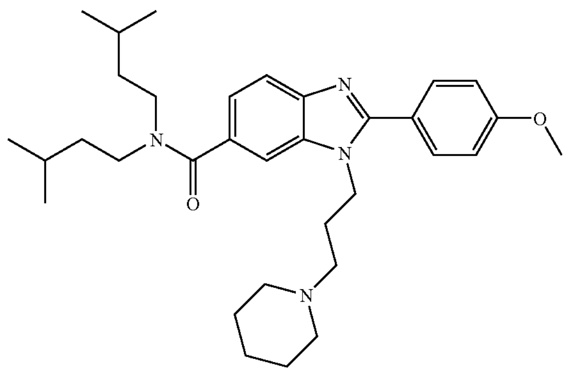 | 533.5 | 8.5 |
| 10 | 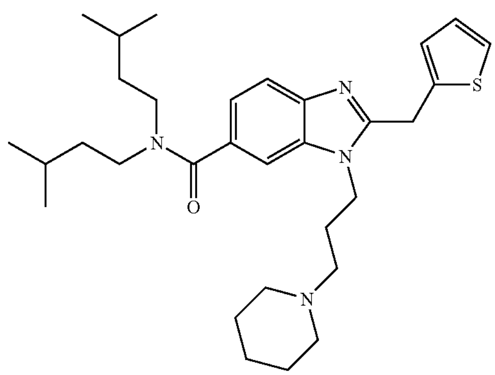 | 523.4 | 8.6 |
| 11 | 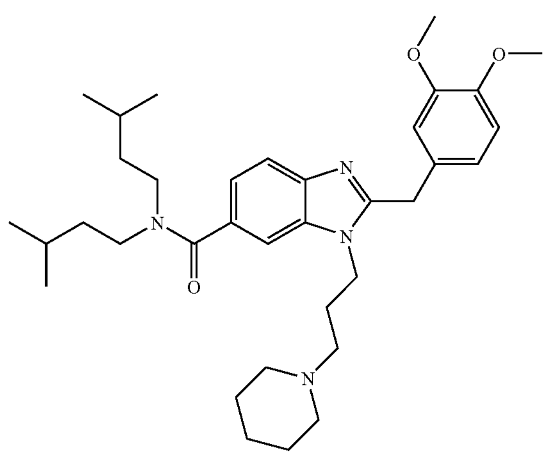 | 577.4 | 8.3 |

| Examples | Molecular Structures | [M & H]+ | rt (min) |
|---|---|---|---|
| 12 | 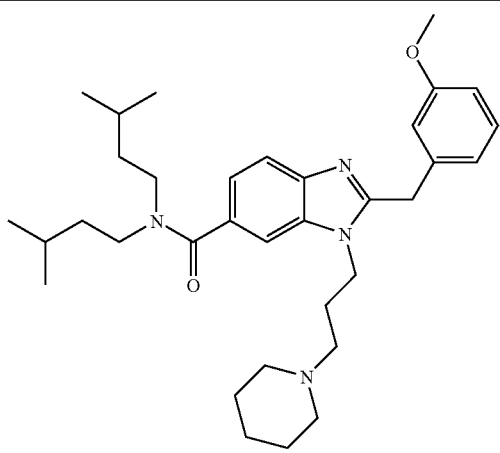 | 547.4 | 8.6 |
| 13 | 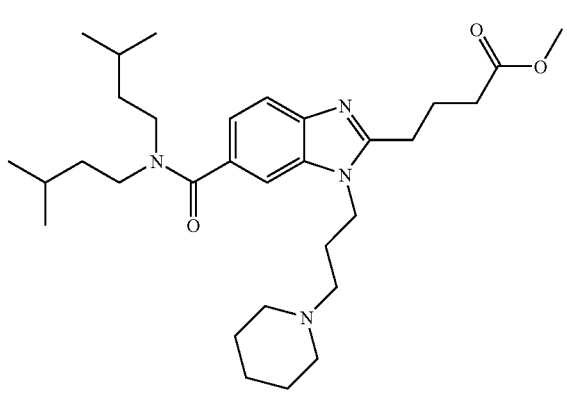 | 527.4 | 8.1 |
| 14 | 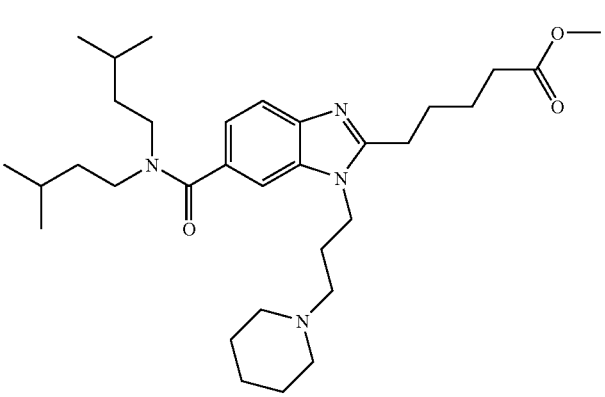 | 541.4 | 8.1 |
| 15 | 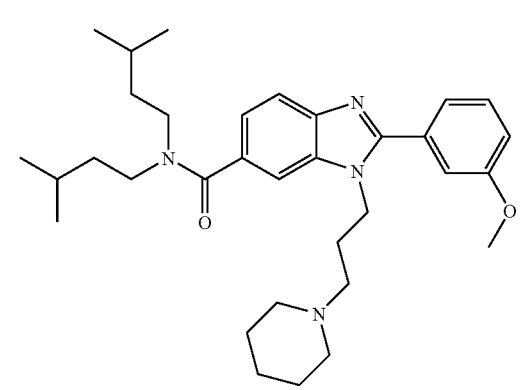 | 533.4 | 8.7 |

-continued

| Examples | Molecular Structures | [M & H]+ | rt (min) |
|---|---|---|---|
| 16 | 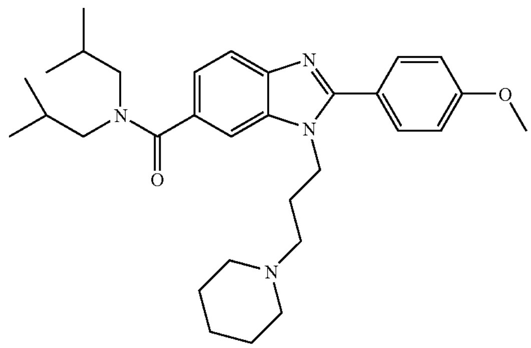 | 505.4 | 8.0 |
| 17 | 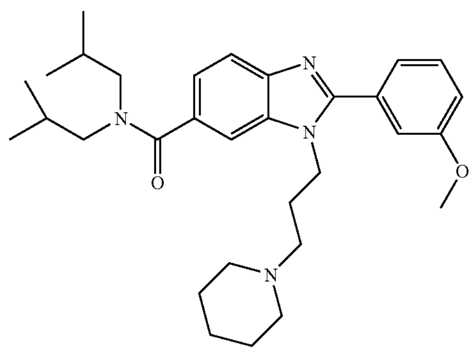 | 505.4 | 8.2 |
| 18 | 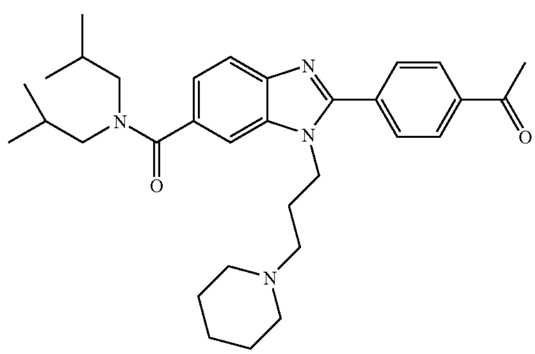 | 517.4 | 8.3 |
| 19 | 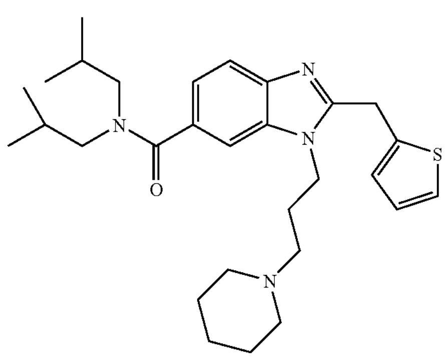 | 495.3 | 8.6 |

-continued

| Examples | Molecular Structures | [M & H]+ | rt (min) |
|---|---|---|---|
| 20 | 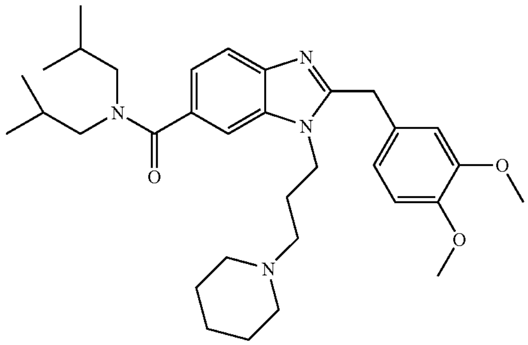 | 549.4 | 8.3 |
| 21 | 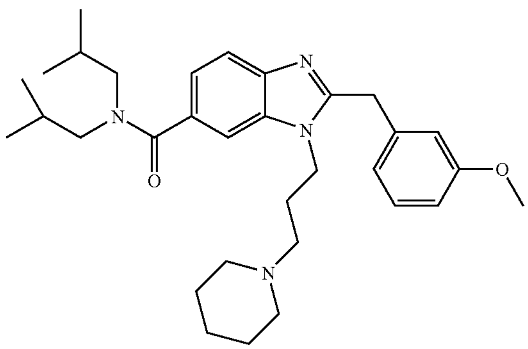 | 519.3 | 8.6 |
| 22 | 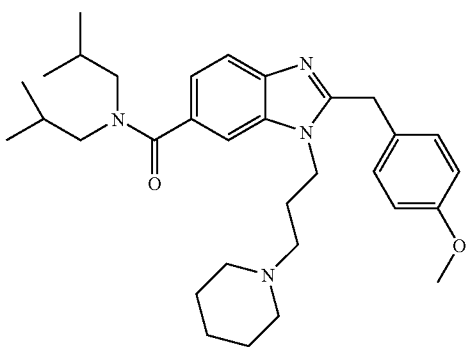 | 519.4 | 8.5 |
| 23 | 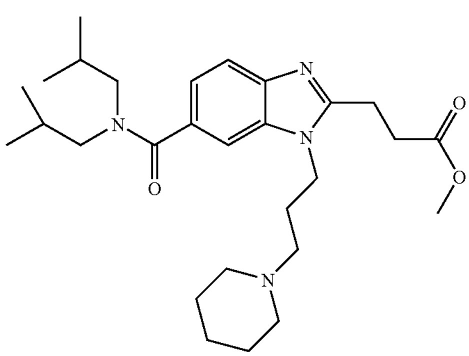 | 485.4 | 8.2 |

-continued

| Examples | Molecular Structures | [M & H]+ | rt (min) |
|---|---|---|---|
| 24 | 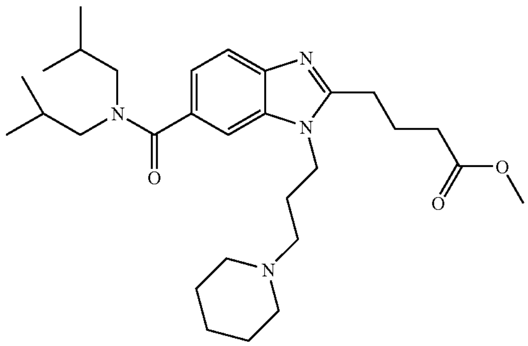 | 499.4 | 8.2 |
| 25 | 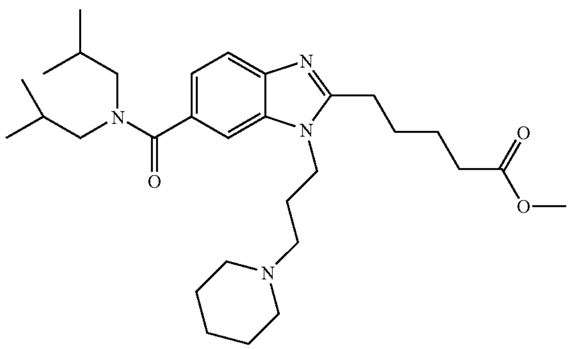 | 513.4 | 8.2 |
| 26 | 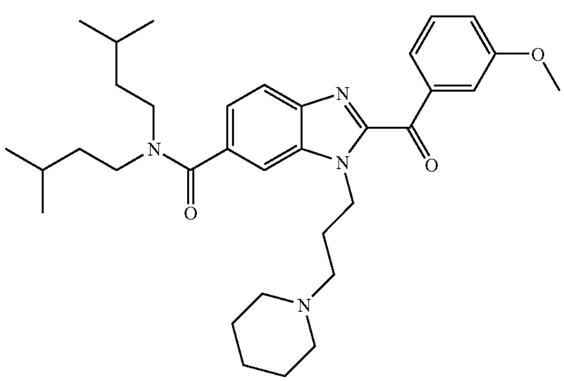 | 561.4 | 10.3 |
| 27 | 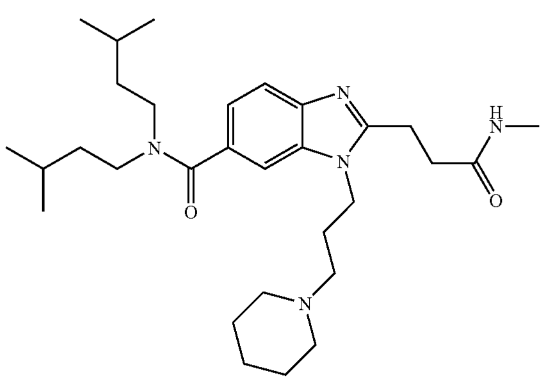 | 512.4 | 8.5 |

| Examples | Molecular Structures | [M & H]+ | rt (min) |
|---|---|---|---|
| 28 | 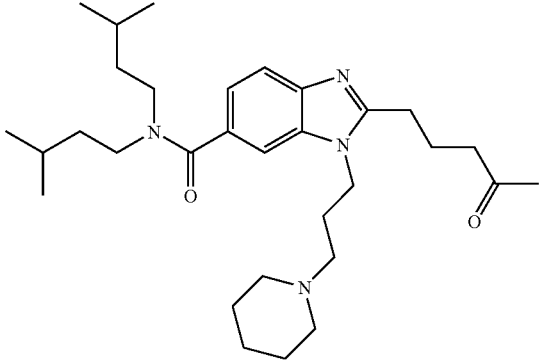 | 511.4 | 8.5 |
| 29 | 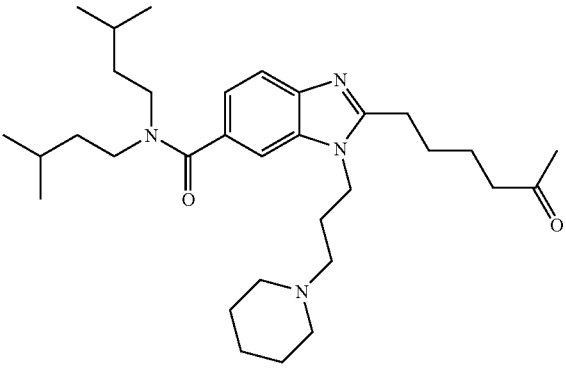 | 525.4 | 8.6 |
| 30 | 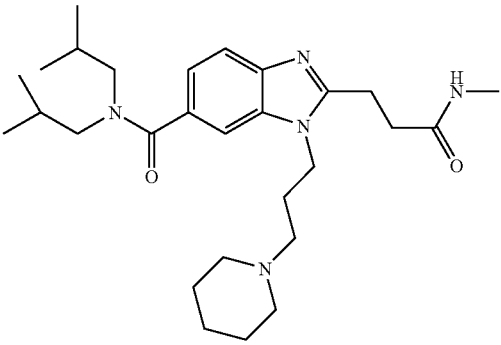 | 484.4 | 8.1 |
| 31 | 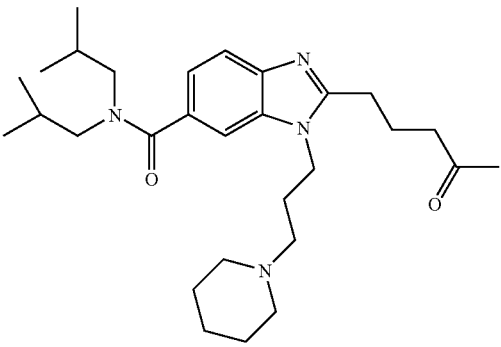 | 483.4 | 8.1 |

-continued
| Examples | Molecular Structures | [M & H]+ | rt (min) |
|---|---|---|---|
| 32 | 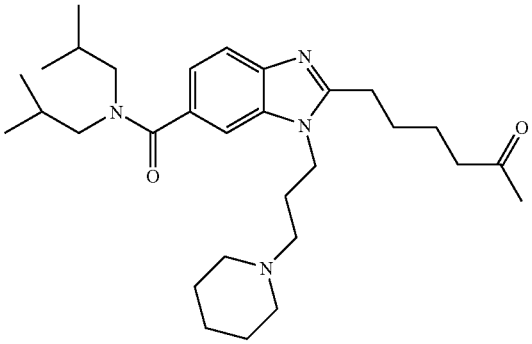 | 497.4 | 8.1 |
| 33 | 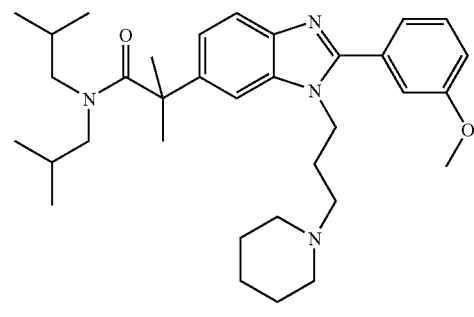 | 547.4 | 8.7 |
| 34 | 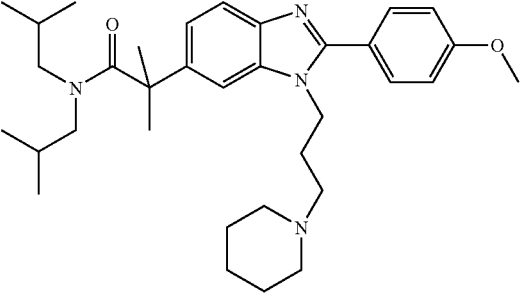 | 547.4 | 8.5 |
| 35 | 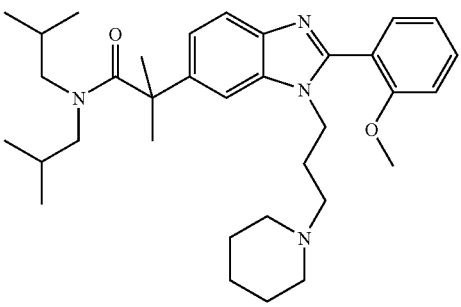 | 547.4 | 8.5 |
| 36 | 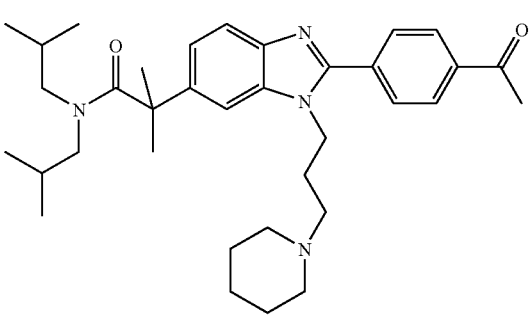 | 559.4 | 8.8 |

| Examples | Molecular Structures | [M & H]+ | rt (min) |
| --- | --- | --- | --- |
| 37 | 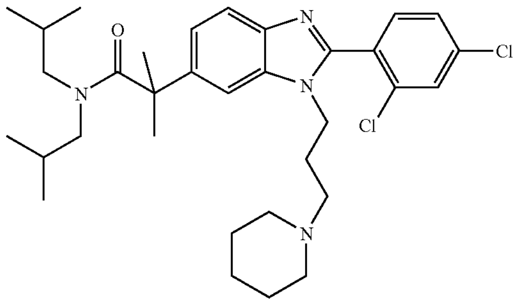 | 585.3 | 9.5 |
| 38 | 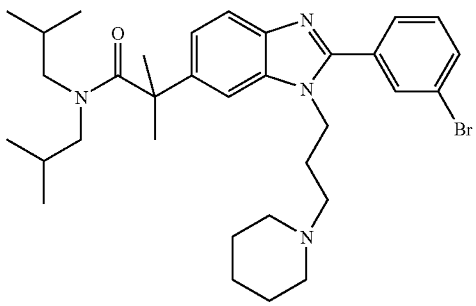 | 595.3 | 9.2 |
| 39 | 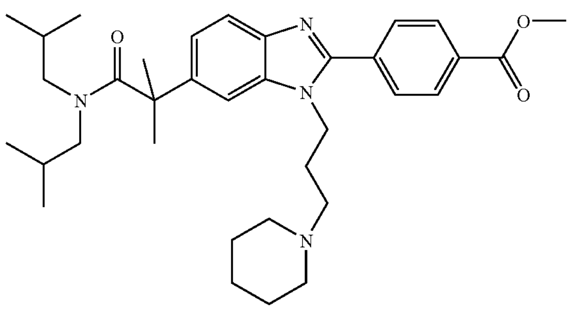 | 575.3 | 9.0 |
| 40 | 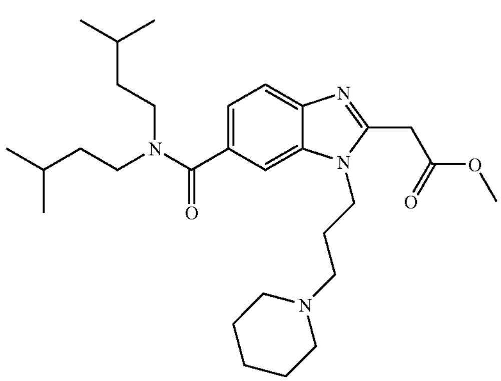 | 499.4 | 8.9 |

-continued

| Examples | Molecular Structures | [M & H]+ | rt (min) |
|---|---|---|---|
| 41 | 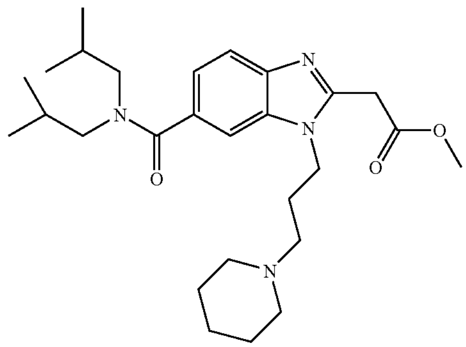 | 471.4 | 8.4 |
| 42 | 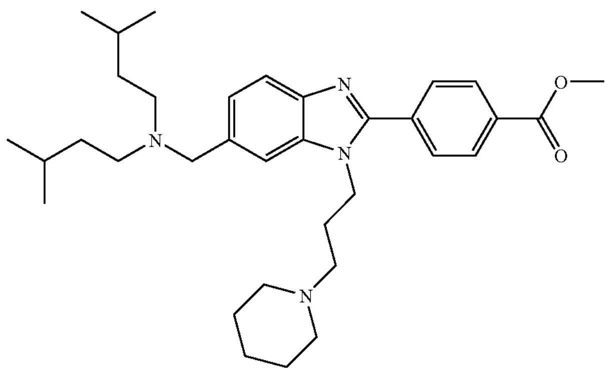 | 547.4 | 8.1 |
| 43 | 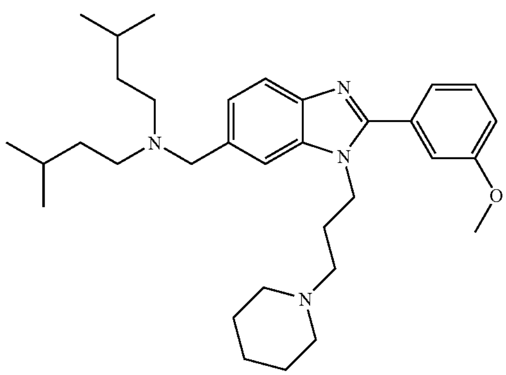 | 519.4 | 8.0 |
| 44 | 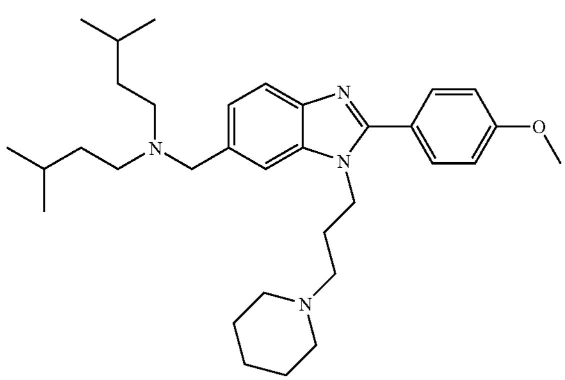 | 519.4 | 8.3 |

-continued

| Examples | Molecular Structures | [M & H]+ | rt (min) |
|---|---|---|---|
| 45 | 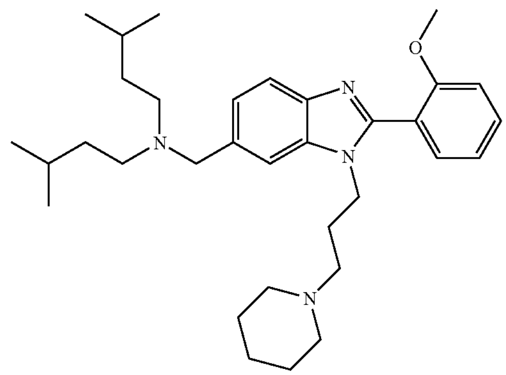 | 519.4 | 7.9 |
| 46 | 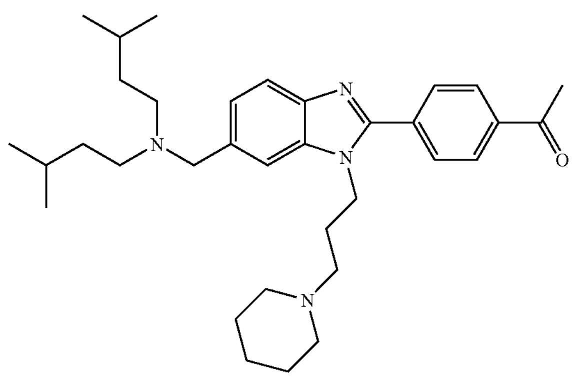 | 531.4 | 8.0 |
| 47 | 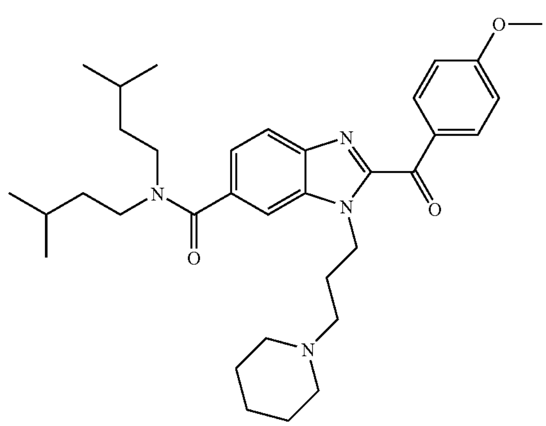 | 561.4 | 10.1 |
| 48 | 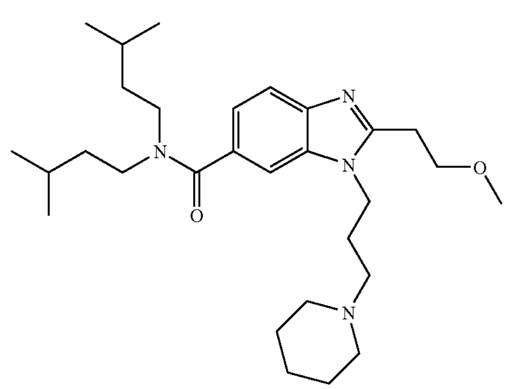 | 485.4 | 8.5 |

| Examples | Molecular Structures | [M & H]+ | rt (min) |
|---|---|---|---|
| 49 | 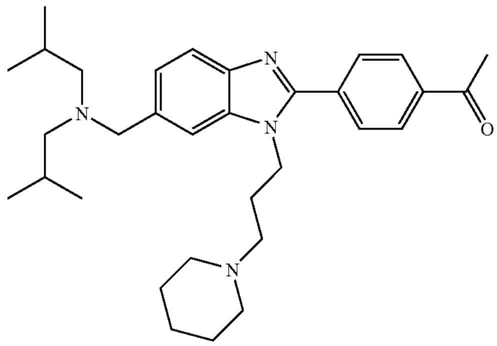 | 503.3 | 7.4 |
| 50 | 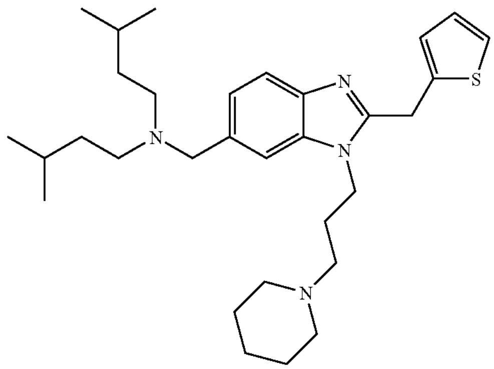 | 509.4 | 7.7 |
| 51 | 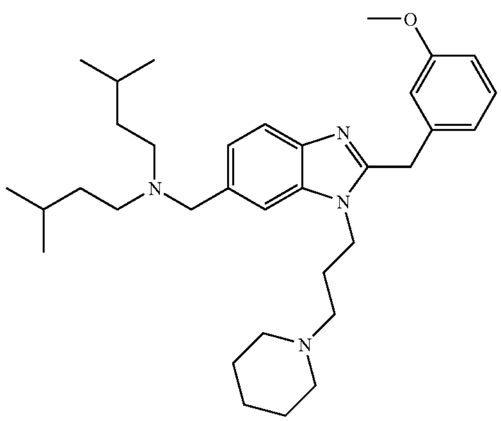 | 533.4 | 7.8 |
| 52 | 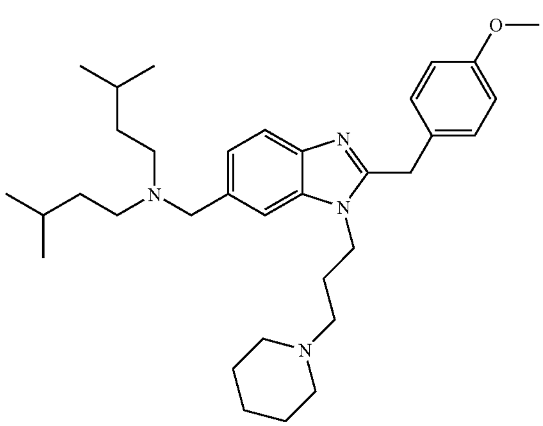 | 533.4 | 7.7 |

-continued

| Examples | Molecular Structures | [M & H]+ | rt (min) |
|---|---|---|---|
| 53 | 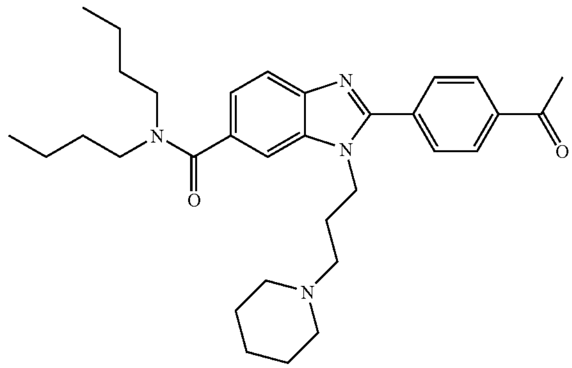 | 517.4 | 8.5 |
| 54 | 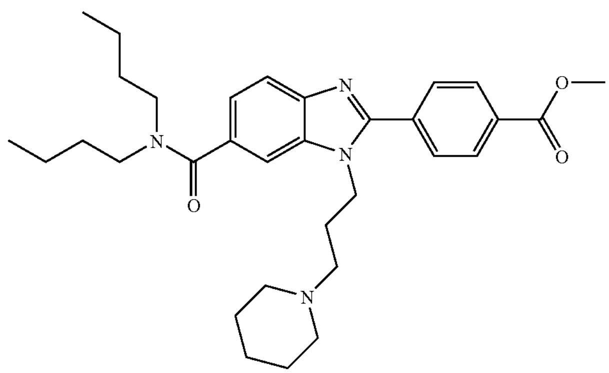 | 533.4 | 8.7 |
| 55 | 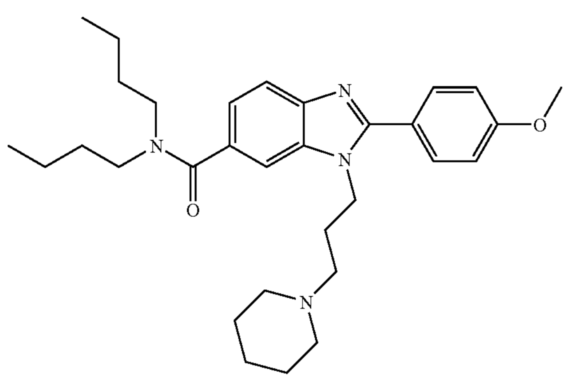 | 505.4 | 8.2 |
| 56 | 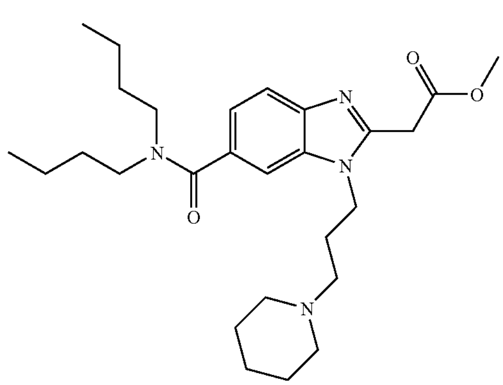 | 471.4 | 8.2 |

-continued
| Examples | Molecular Structures | [M & H]+ | rt (min) |
|---|---|---|---|
| 57 | 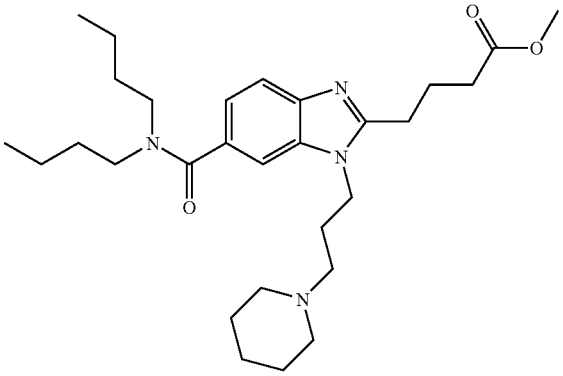 | 499.5 | 7.9 |
| 58 | 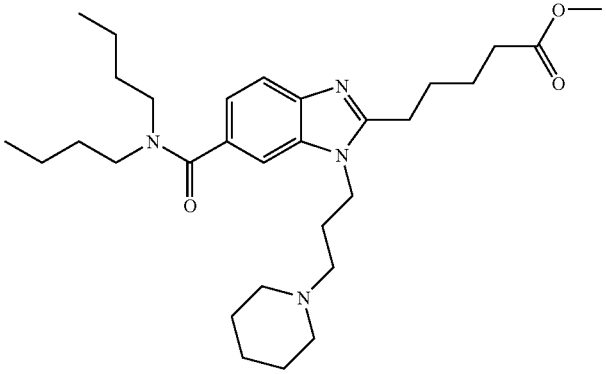 | 513.5 | 8.0 |
| 59 | 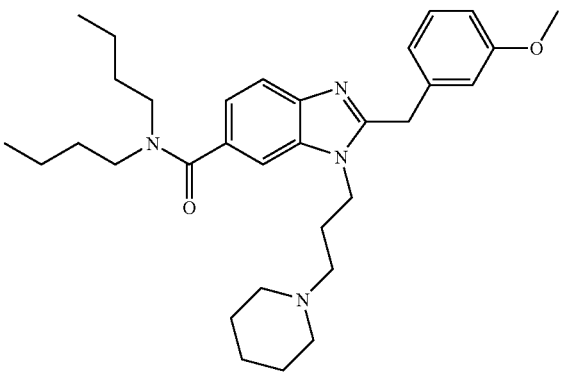 | 519.4 | 8.3 |
| 60 | 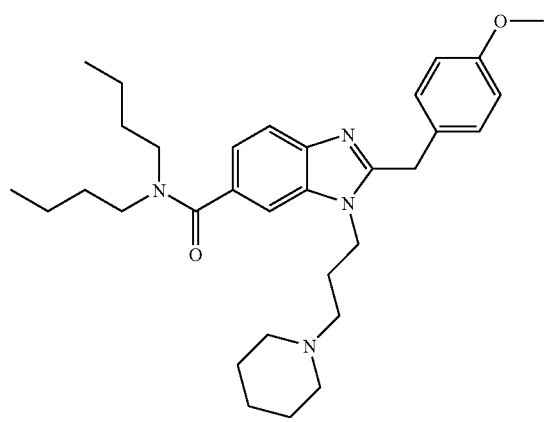 | 519.4 | 8.3 |

-continued
| Examples | Molecular Structures | [M & H]+ | rt (min) |
|---|---|---|---|
| 61 | 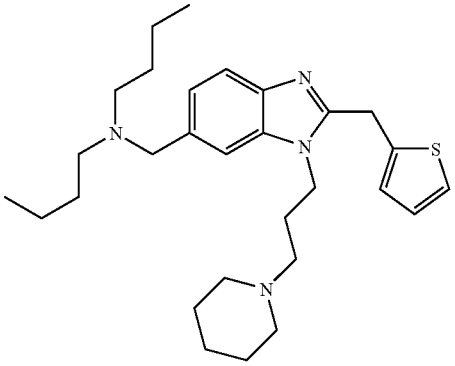 | 481.4 | 7.5 |
| 62 | 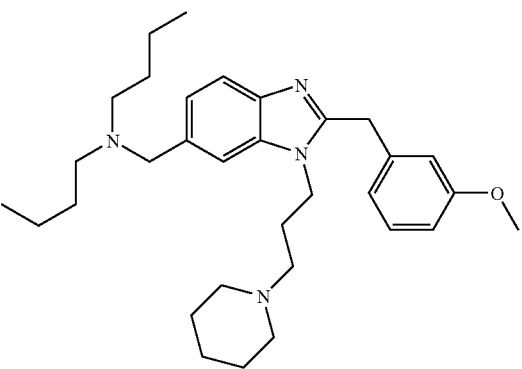 | 505.5 | 7.5 |
| 63 | 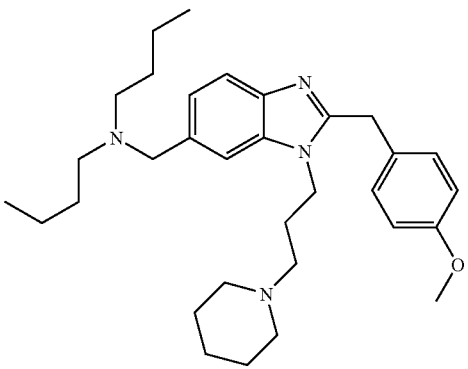 | 505.5 | 7.5 |
| 64 | 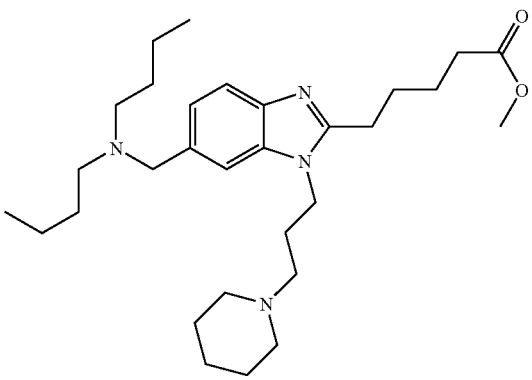 | 499.5 | 7.3 |

-continued
| Examples | Molecular Structures | [M & H]+ | rt (min) |
|---|---|---|---|
| 65 | 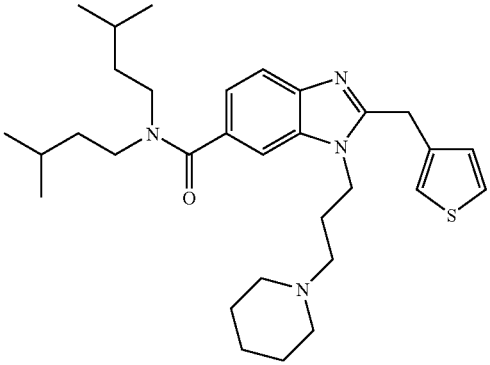 | 523.2 | 7.8 |
| 66 | 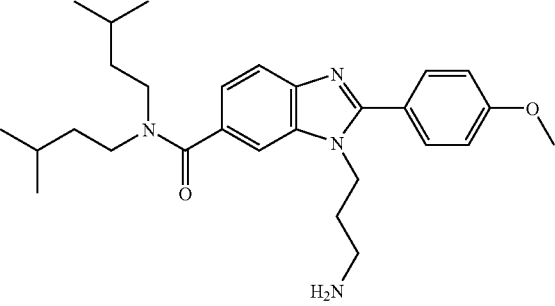 | 465.4 | 8.2 |
| 67 | 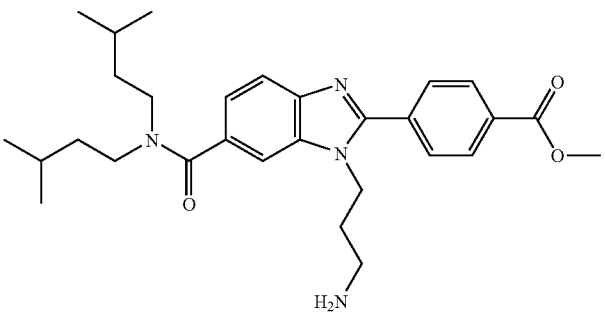 | 493.4 | 8.7 |
| 68 | 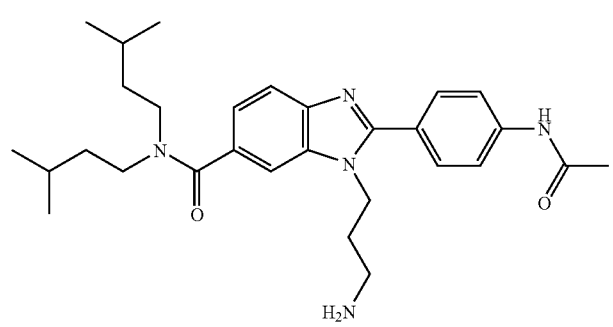 | 492.4 | 8.1 |

-continued

| Examples | Molecular Structures | [M & H]+ | rt (min) |
|---|---|---|---|
| 69 | 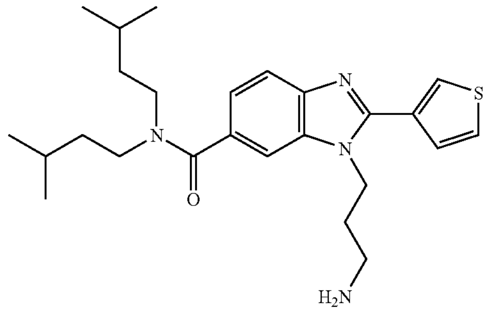 | 441.4 | 8.3 |
| 70 | 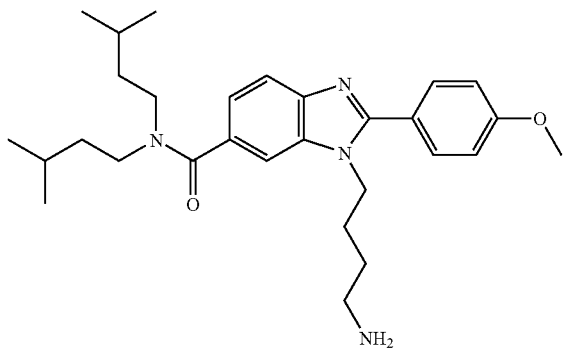 | 479.4 | 8.2 |
| 71 | 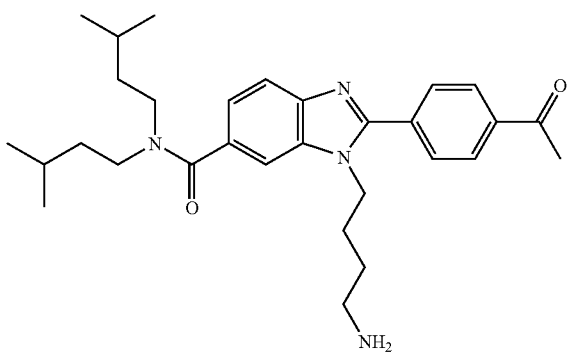 | 491.4 | 8.6 |
| 72 | 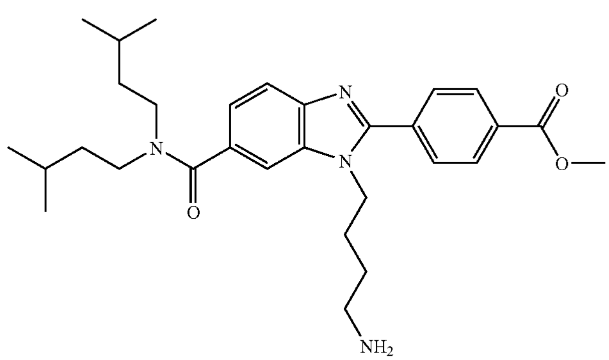 | 507.4 | 8.7 |

-continued
| Examples | Molecular Structures | [M & H]+ | rt (min) |
|---|---|---|---|
| 73 | 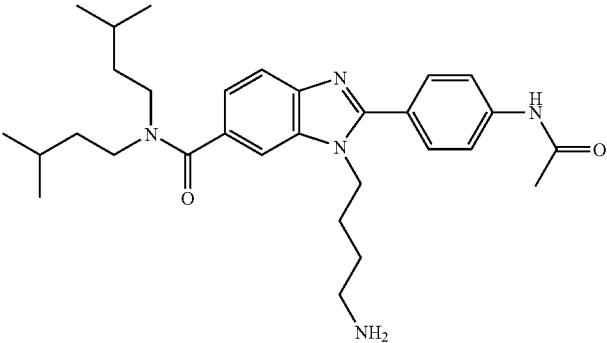 | 506.5 | 8.1 |
| 74 | 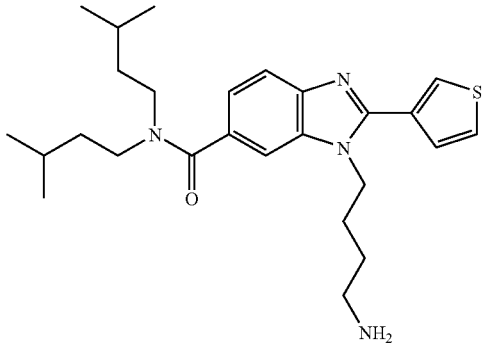 | 455.4 | 8.2 |
| 75 | 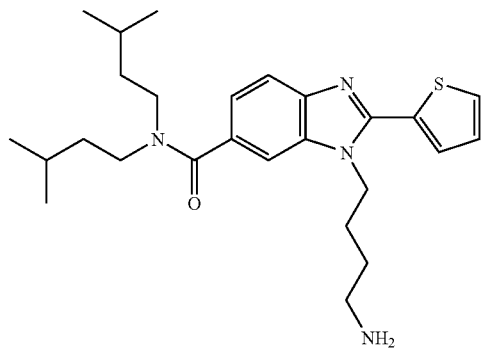 | 455.4 | 8.6 |
| 76 | 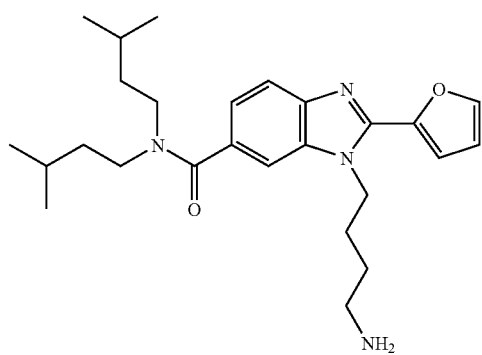 | 439.4 | 8.4 |

-continued

| Examples | Molecular Structures | [M & H]+ | rt (min) |
| --- | --- | --- | --- |
| 77 | 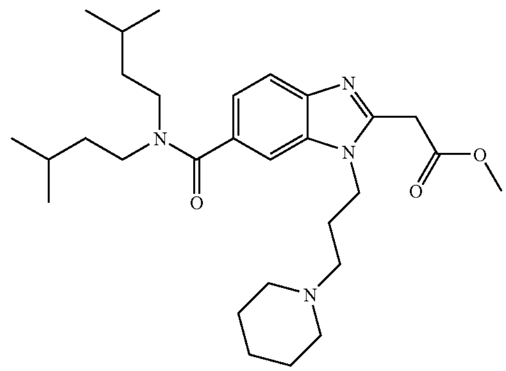 | 499.4 | 8.9 |
| 78 | 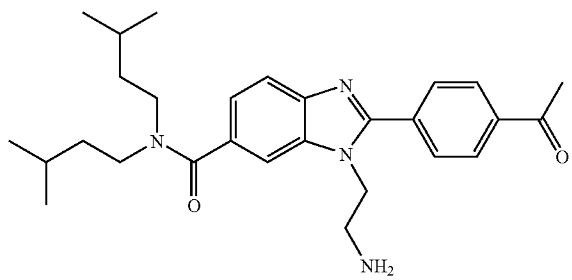 | 463.4 | 8.6 |
| 79 | 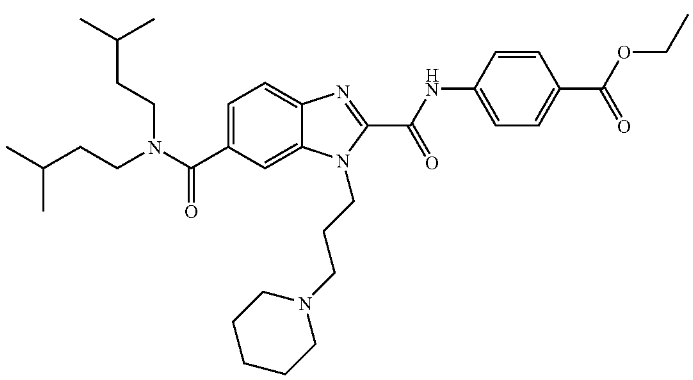 | 618.5 | 10.6 |
| 80 | 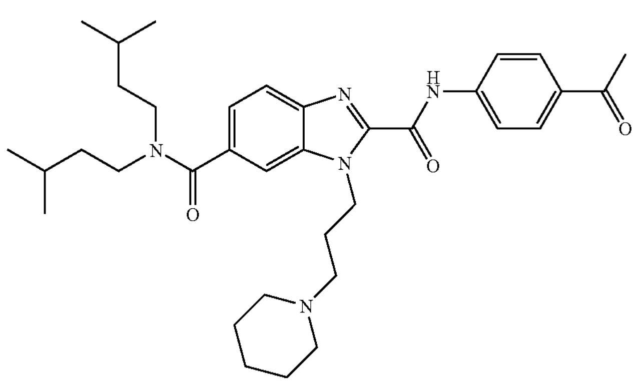 | 588.4 | 9.7 |

| Examples | Molecular Structures | [M & H]+ | rt (min) |
|---|---|---|---|
| 81 | 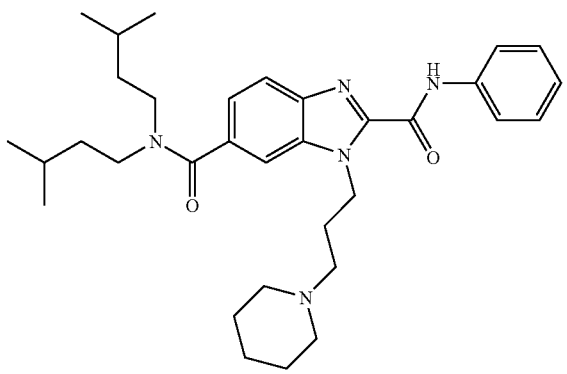 | 546.4 | 9.9 |
| 82 | 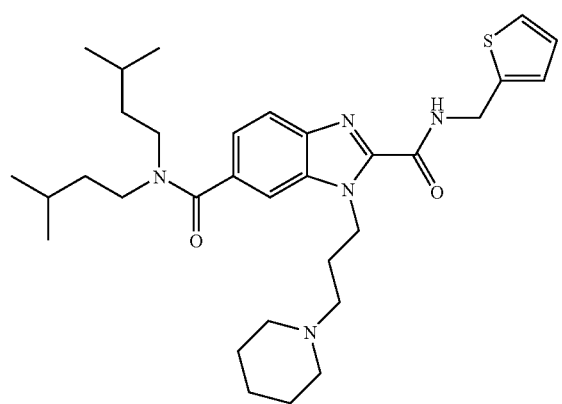 | 566.4 | 9.7 |
| 83 | 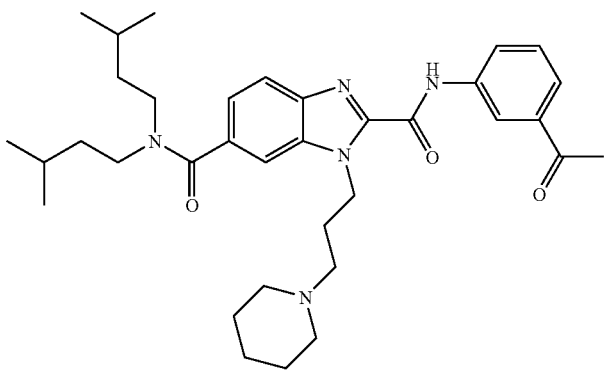 | 588.4 | 10.0 |
| 84 | 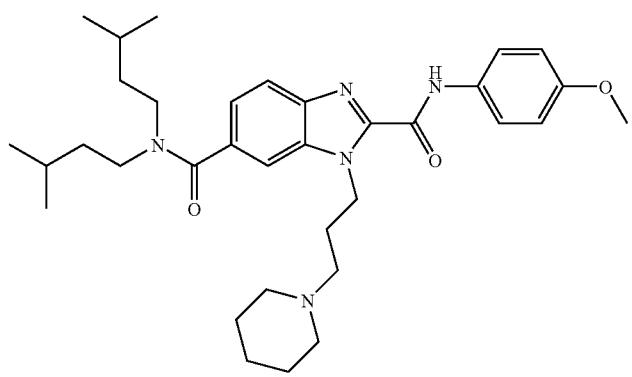 | 576.4 | 10.1 |

-continued
| Examples | Molecular Structures | [M & H]+ | rt (min) |
|---|---|---|---|
| 85 | 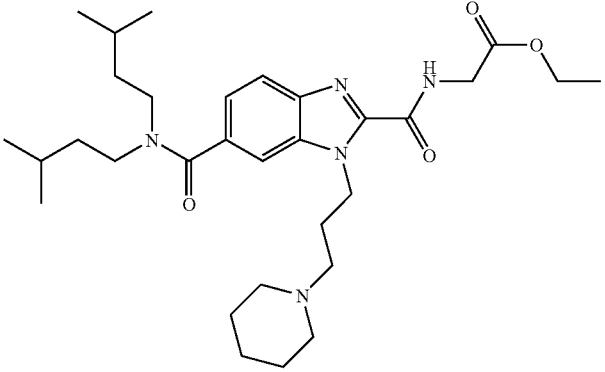 | 556.4 | 9.5 |
| 86 | 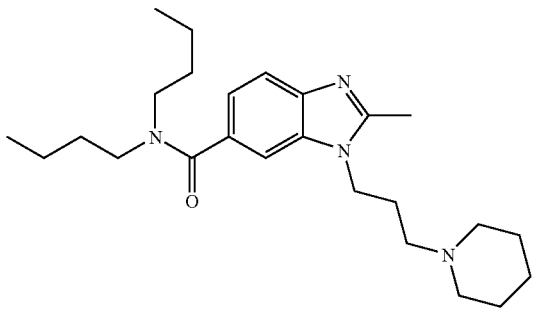 | 413.4 | 7.8 |
| 87 | 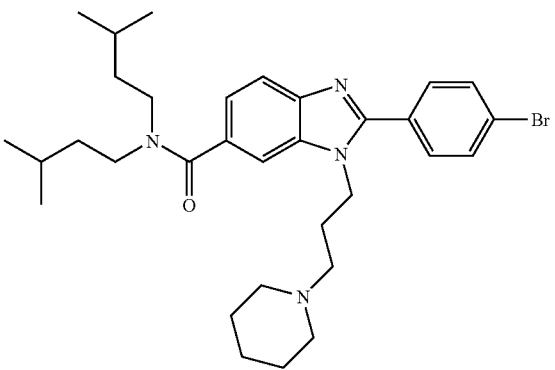 | 581.2 | 9.3 |
| 88 | 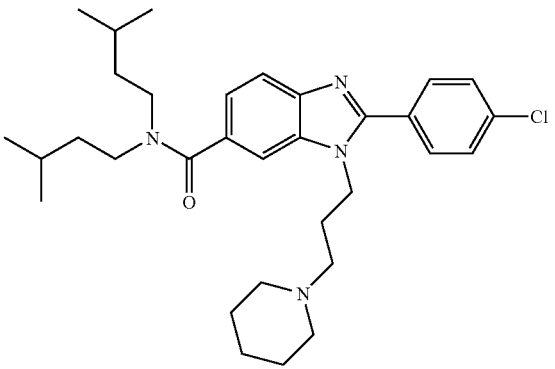 | 537.3 | 9.2 |

-continued

| Examples | Molecular Structures | [M & H]+ | rt (min) |
|---|---|---|---|
| 89 | 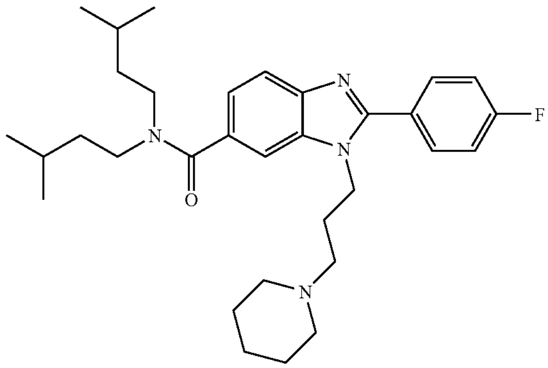 | 521.3 | 8.9 |
| 90 | 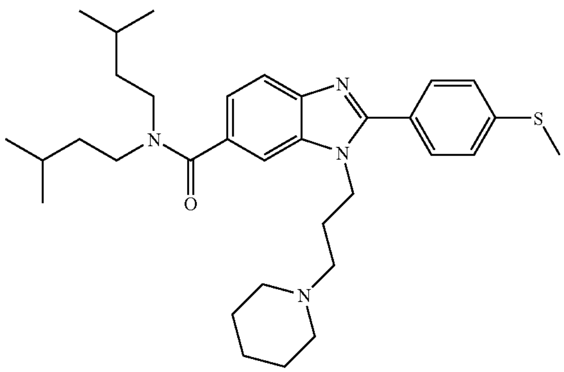 | 549.3 | 8.9 |
| 91 | 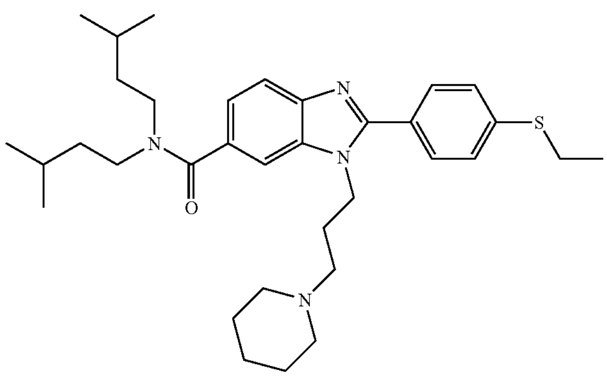 | 563.3 | 9.1 |
| 92 | 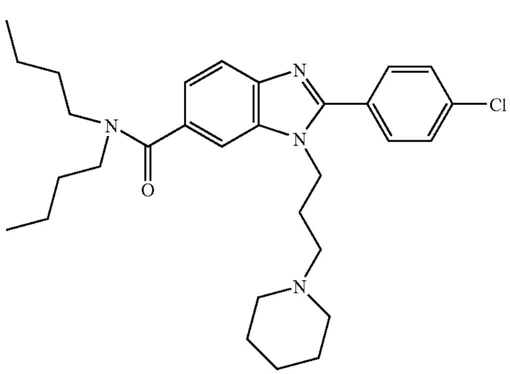 | 509.3 | 8.7 |

-continued

| Examples | Molecular Structures | [M & H]+ | rt (min) |
|---|---|---|---|
| 93 | 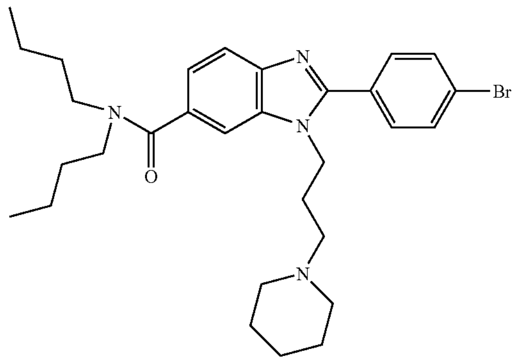 | 555.2 | 8.8 |
| 94 | 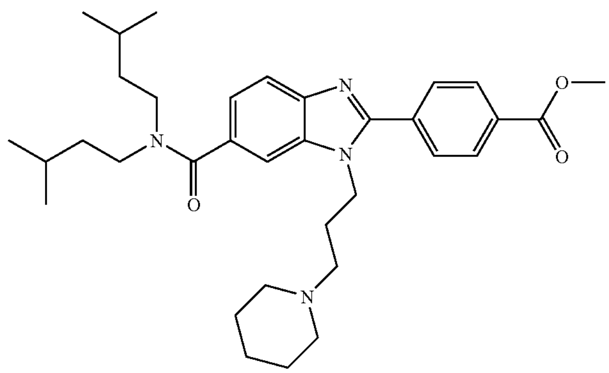 | 561.3 | 9.2 |
| 95 | 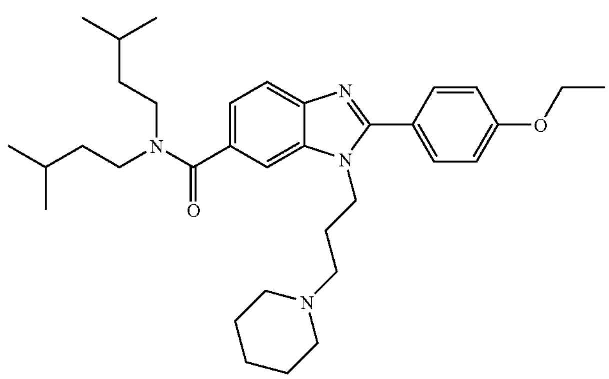 | 547.3 | 8.7 |
| 96 | 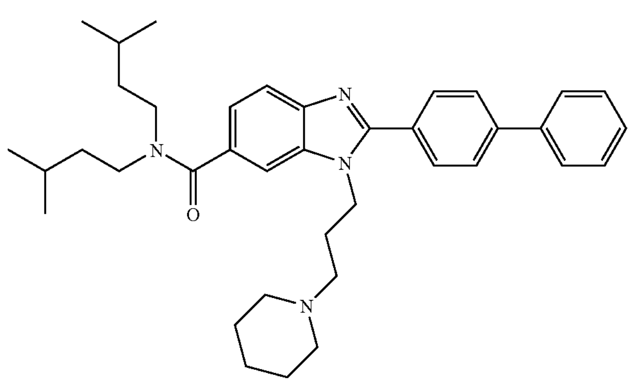 | 579.3 | 9.5 |

-continued
| Examples | Molecular Structures | [M & H]+ | rt (min) |
|---|---|---|---|
| 97 | 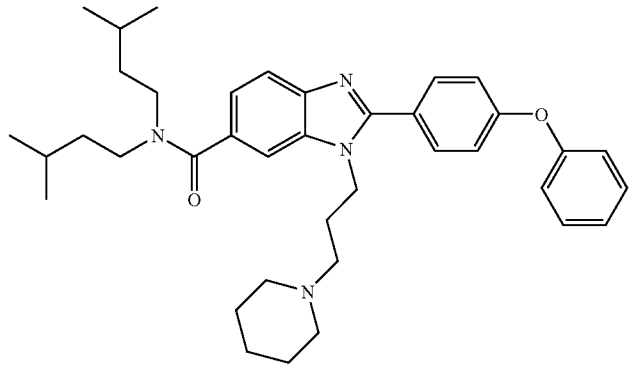 | 595.3 | 9.4 |
| 98 | 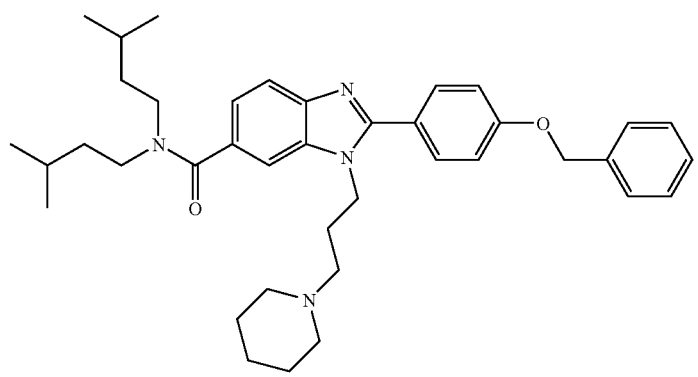 | 609.3 | 9.3 |
| 99 | 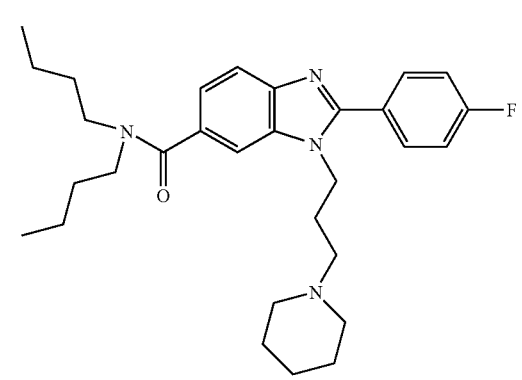 | 493.3 | 8.4 |
| 100 | 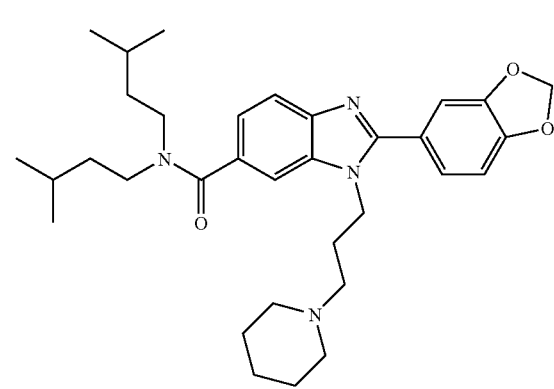 | 547.3 | 8.7 |

-continued

| Examples | Molecular Structures | [M & H]+ | rt (min) |
|---|---|---|---|
| 101 | 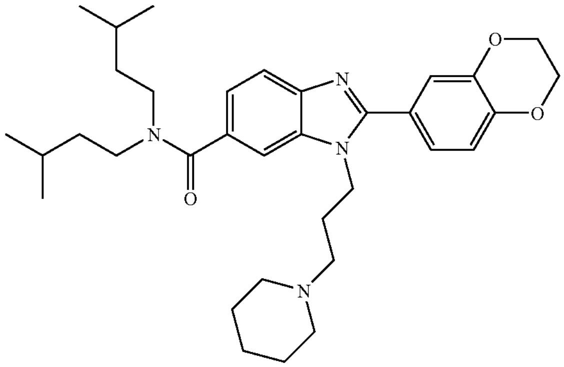 | 561.3 | 8.6 |
| 102 | 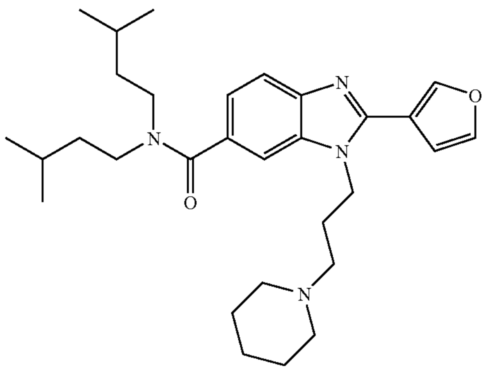 | 493.3 | 8.6 |
| 103 | 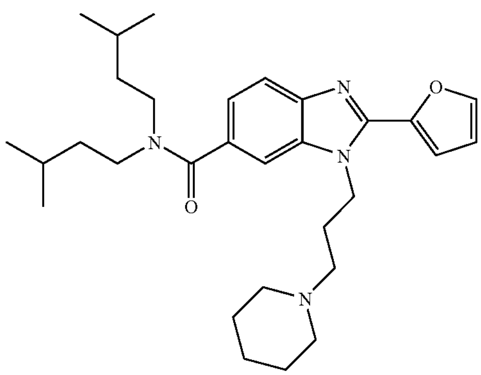 | 509.3 | 8.6 |
| 104 | 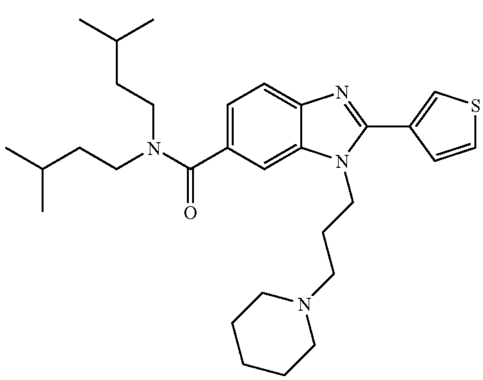 | 509.3 | 8.6 |

-continued
| Examples | Molecular Structures | [M & H]+ | rt (min) |
|---|---|---|---|
| 105 | 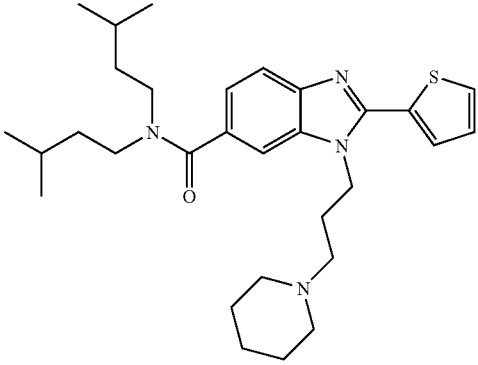 | 509.3 | 8.6 |
| 106 | 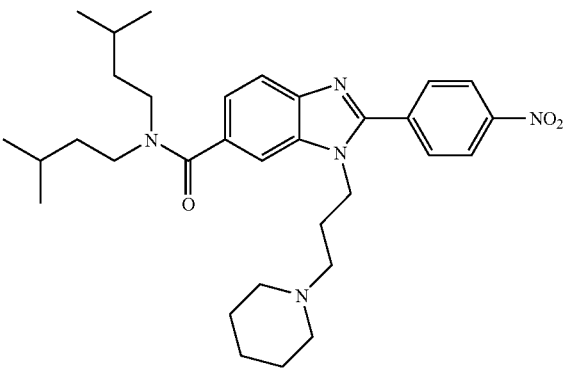 | 548.3 | 9.2 |
| 107 | 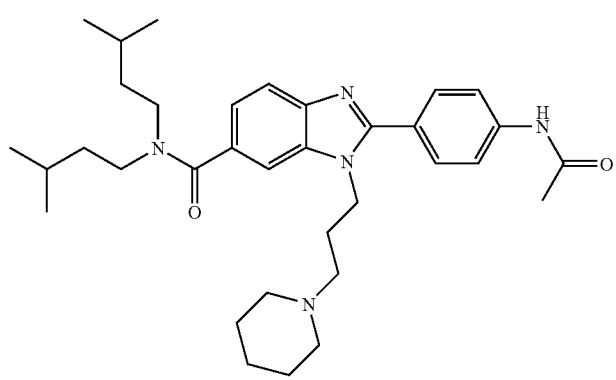 | 560.4 | 8.3 |
| 108 | 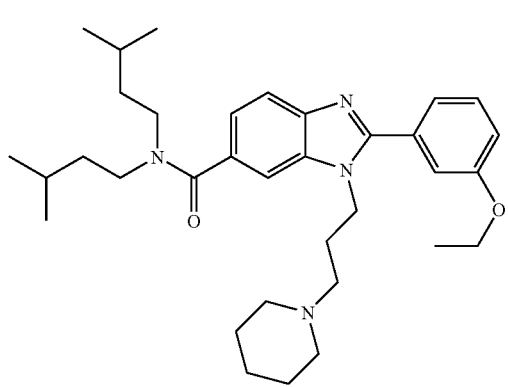 | 547.4 | 8.9 |

-continued

| Examples | Molecular Structures | [M & H]+ | rt (min) |
|---|---|---|---|
| 109 | 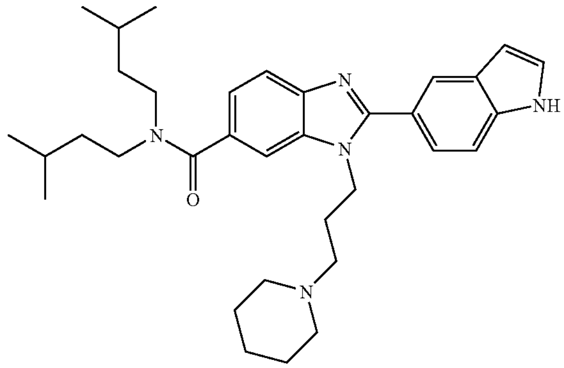 | 542.4 | 8.3 |
| 110 | 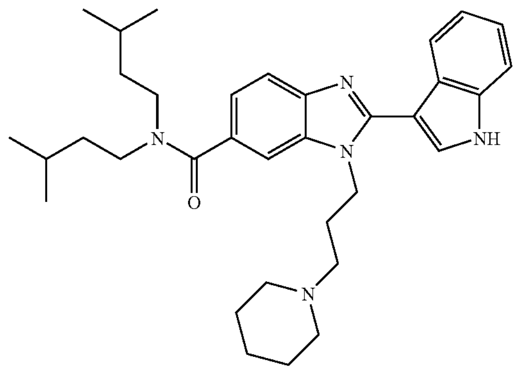 | 542.3 | 8.3 |
| 111 | 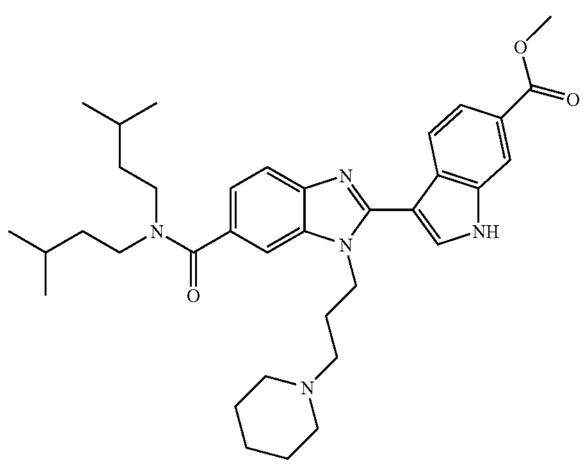 | 600.3 | 8.5 |
| 112 | 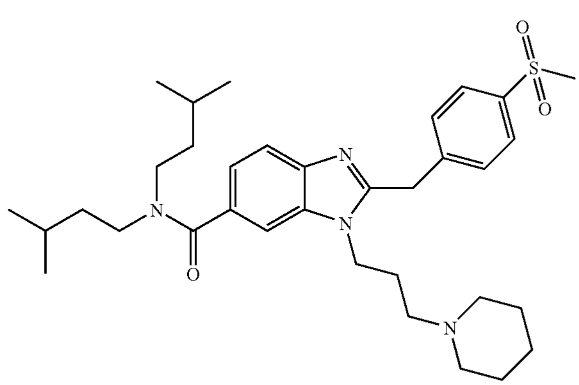 | 595.4 | 8.5 |

-continued

| Examples | Molecular Structures | [M & H]+ | rt (min) |
|---|---|---|---|
| 113 | 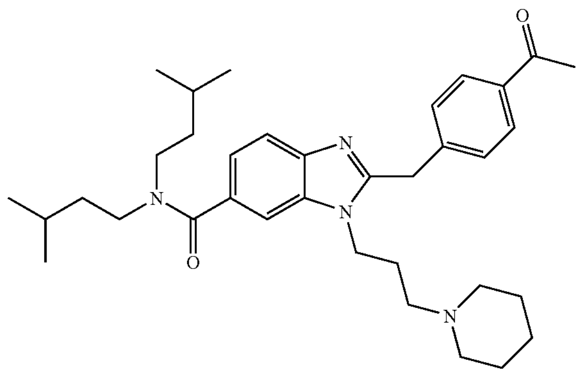 | 559.4 | 8.5 |
| 114 | 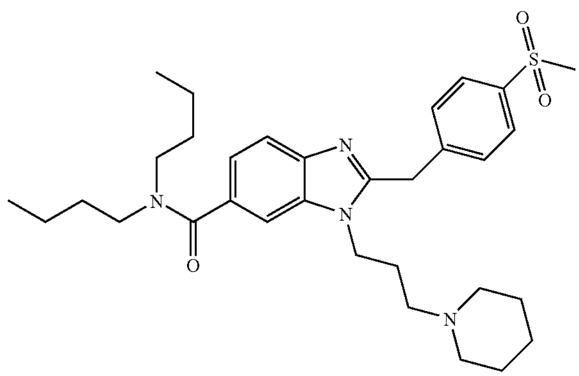 | 567.3 | 8.1 |
| 115 | 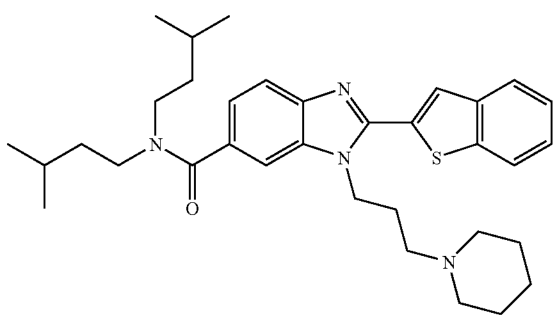 | 559.3 | 9.5 |
| 116 | 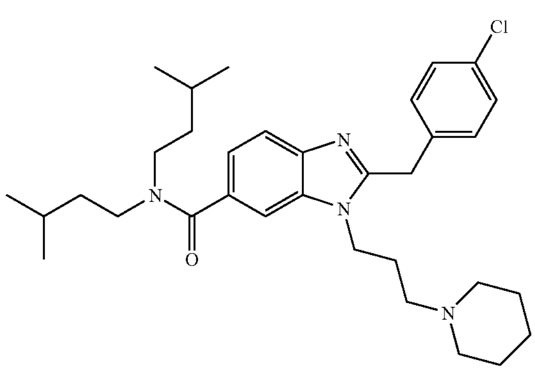 | 551.4 | 8.8 |

-continued

| Examples | Molecular Structures | [M & H]+ | rt (min) |
|---|---|---|---|
| 117 | 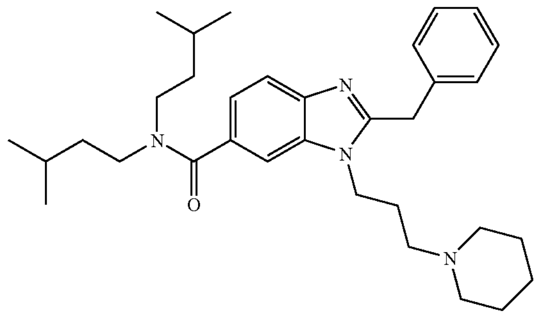 | 517.4 | 8.4 |
| 118 | 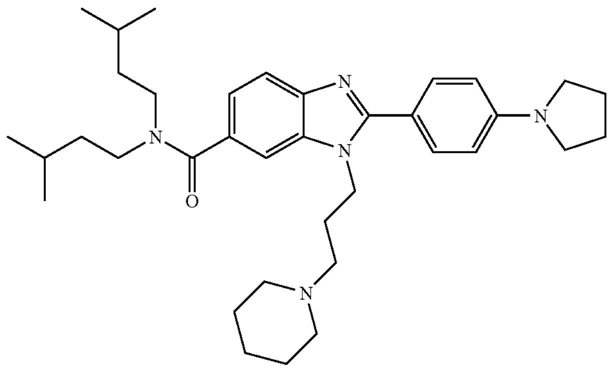 | 572.4 | 8.3 |
| 119 | 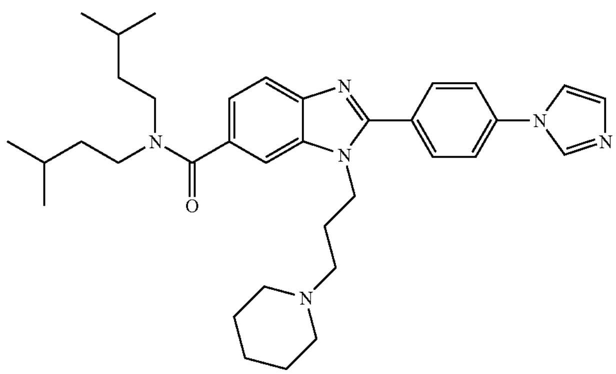 | 569.4 | 8.0 |
| 120 | 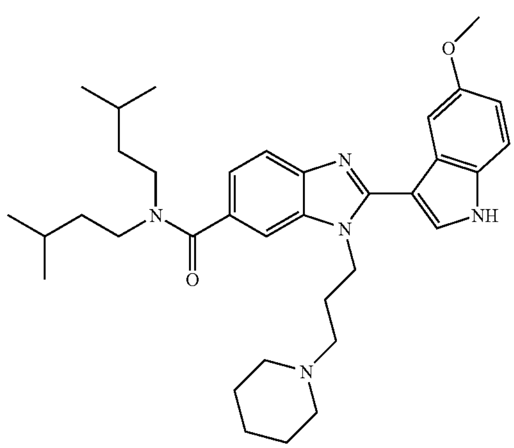 | 572.4 | 8.2 |

-continued

| Examples | Molecular Structures | [M & H]+ | rt (min) |
|---|---|---|---|
| 121 | 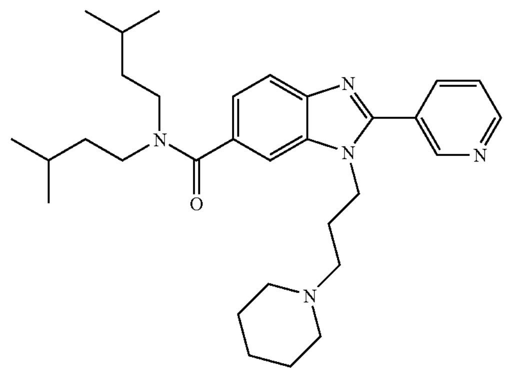 | 504.4 | 8.4 |
| 122 | 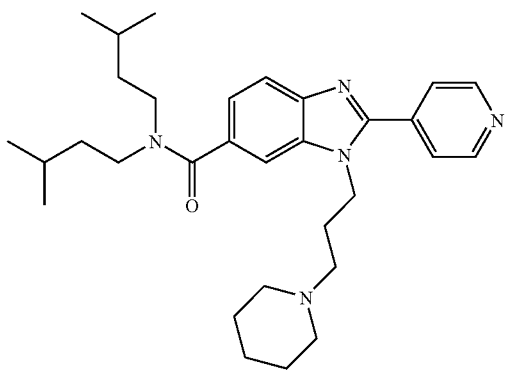 | 504.4 | 8.4 |
| 123 | 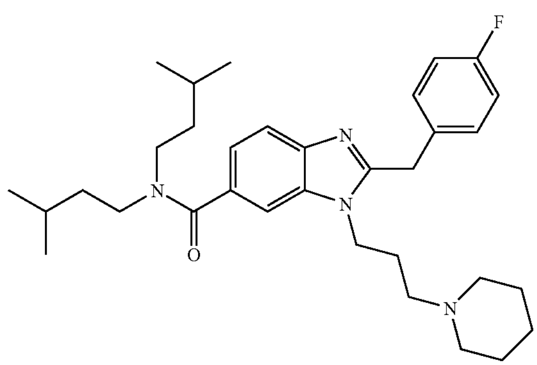 | 535.4 | 8.6 |
| 124 | 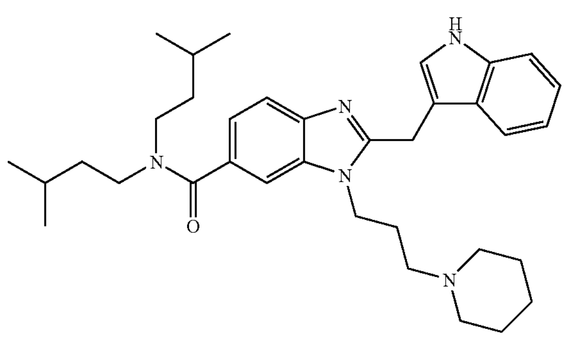 | 556.3 | 8.4 |

-continued
| Examples | Molecular Structures | [M & H]+ | rt (min) |
|---|---|---|---|
| 125 | 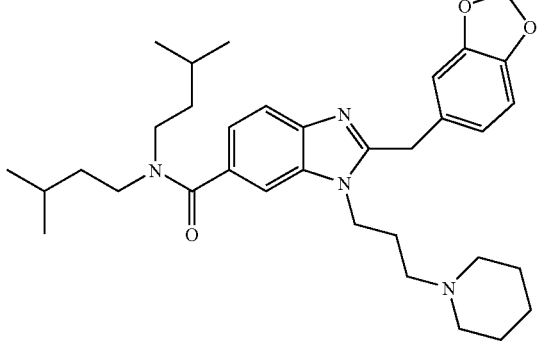 | 561.4 | 8.4 |
| 126 | 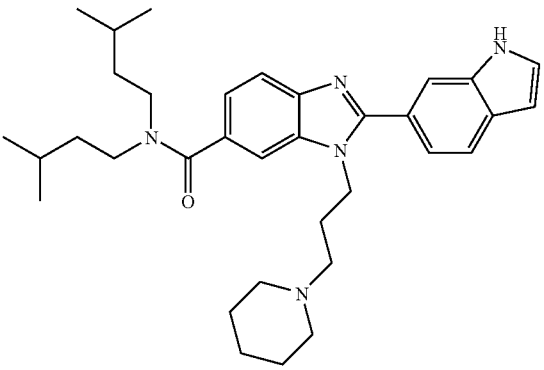 | 542.4 | 8.3 |
| 127 | 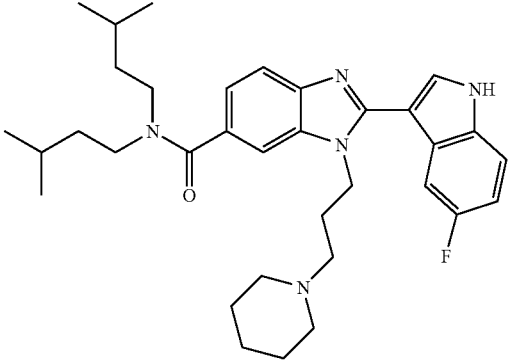 | 560.4 | 8.4 |
| 128 | 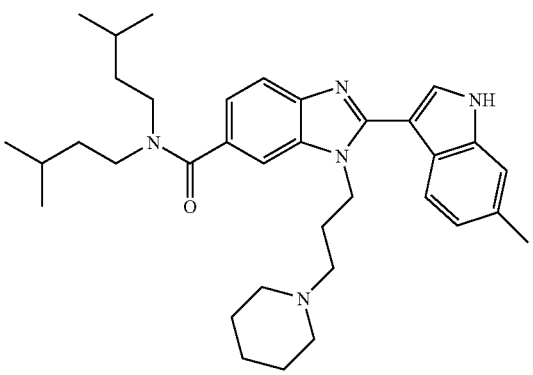 | 556.4 | 8.3 |

-continued
| Examples | Molecular Structures | [M & H]+ | rt (min) |
|---|---|---|---|
| 129 | 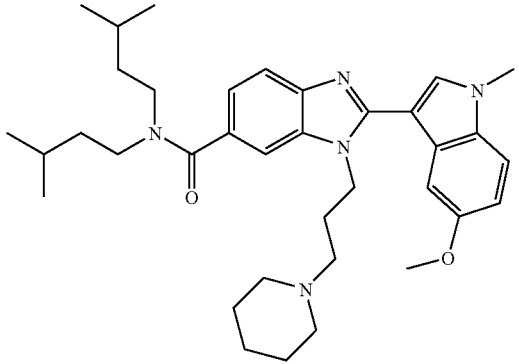 | 586.4 | 8.3 |
| 130 | 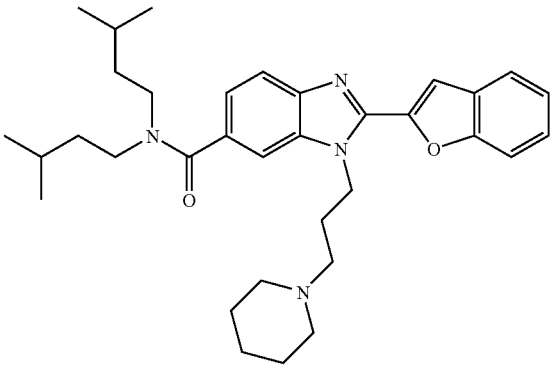 | 543.4 | 9.4 |
| 131 | 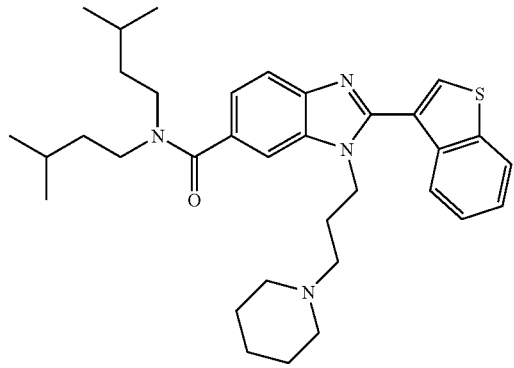 | 559.3 | 9.1 |
| 132 | 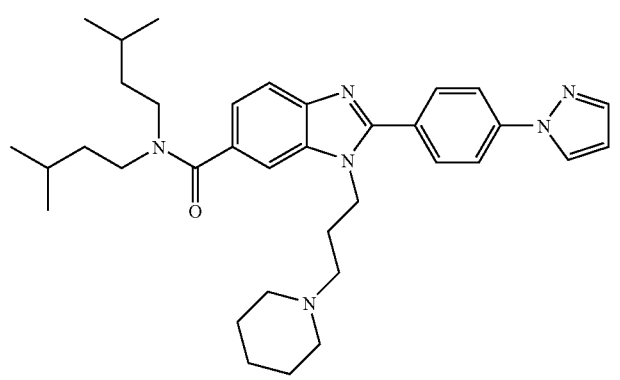 | 569.4 | 8.7 |

-continued
| Examples | Molecular Structures | [M & H]+ | rt (min) |
|---|---|---|---|
| 133 | 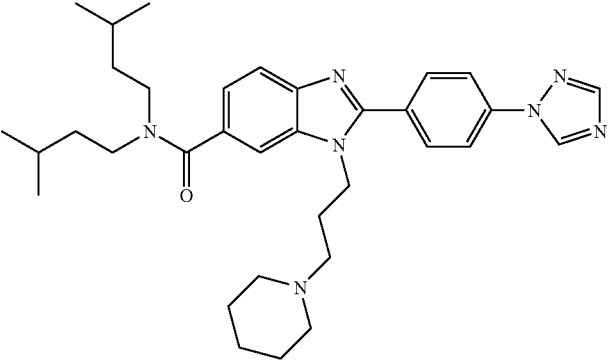 | 570.4 | 8.5 |
| 134 | 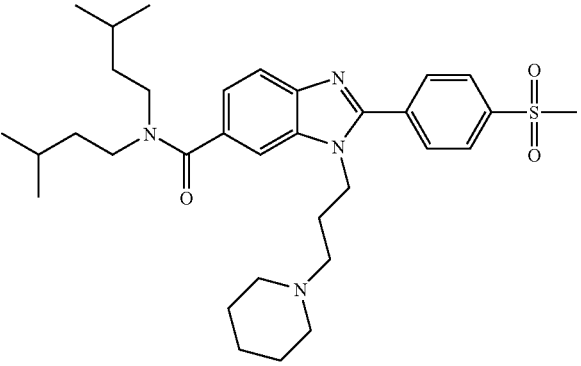 | 581.4 | 8.7 |
| 135 | 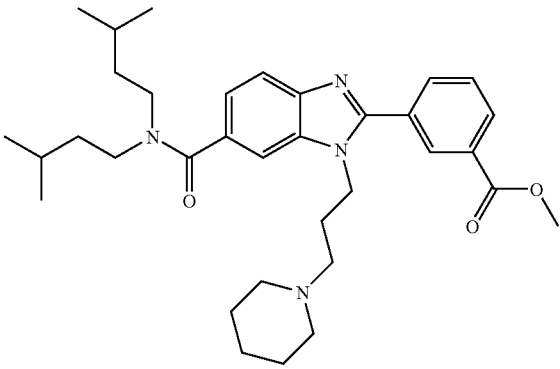 | 561.4 | 8.8 |
| 136 | 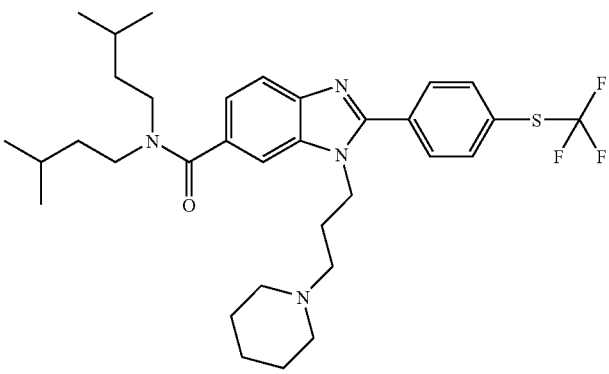 | 603.4 | 9.5 |

-continued
| Examples | Molecular Structures | [M & H]+ | rt (min) |
|---|---|---|---|
| 137 | 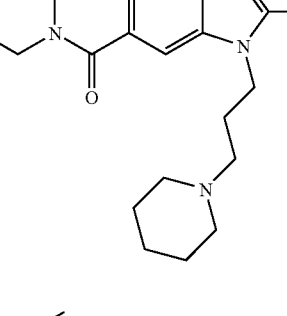 | 556.5 | 8.3 |
| 138 | 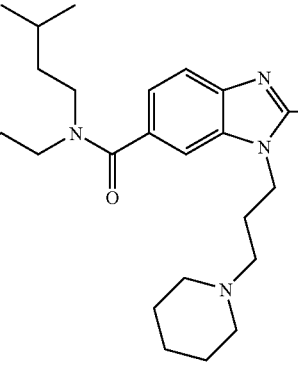 | 504.4 | 8.9 |
| 139 | 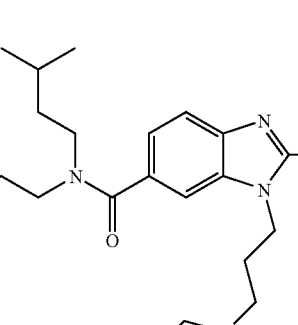 | 503.4 | 8.5 |
| 140 | 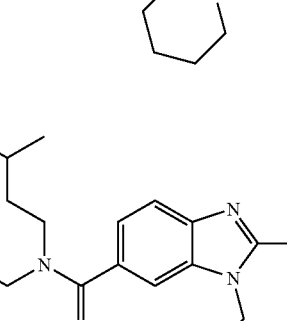 | 560.4 | 8.4 |

-continued
| Examples | Molecular Structures | [M & H]+ | rt (min) |
|---|---|---|---|
| 141 | 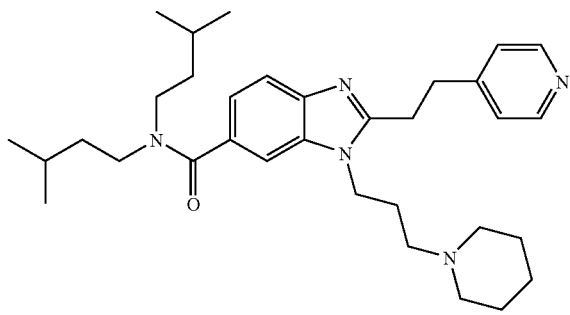 | 532.5 | 7.8 |
| 142 | 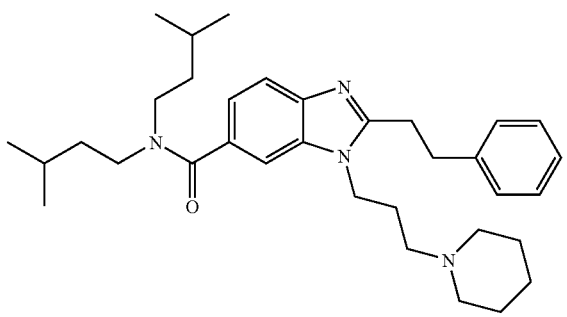 | 531.5 | 8.4 |
| 143 | 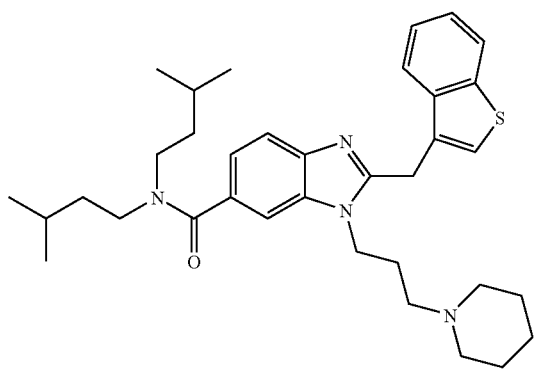 | 573.4 | 8.9 |
| 144 | 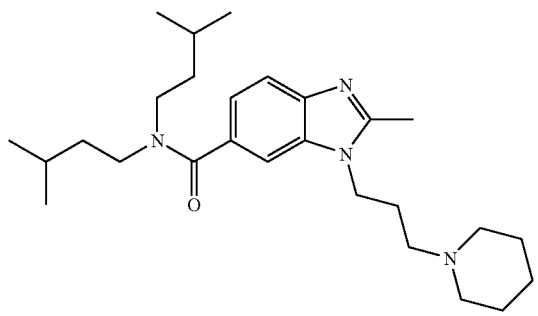 | 441.4 | 7.8 |

-continued

| Examples | Molecular Structures | [M & H]+ | rt (min) |
| --- | --- | --- | --- |
| 145 | 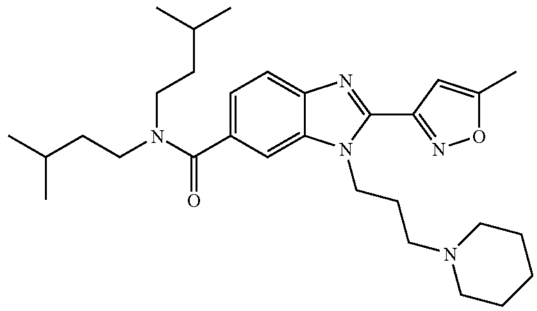 | 508.3 | 9.2 |
| 146 | 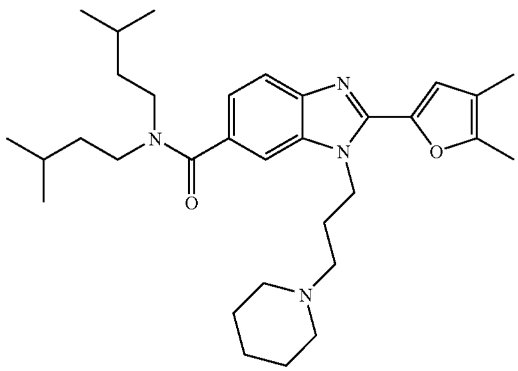 | 521.3 | 8.9 |
| 147 | 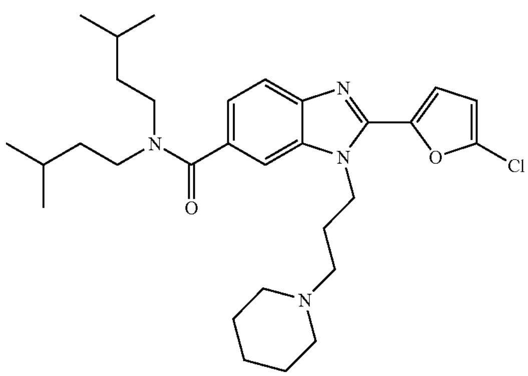 | 527.3 | 9.2 |
| 148 | 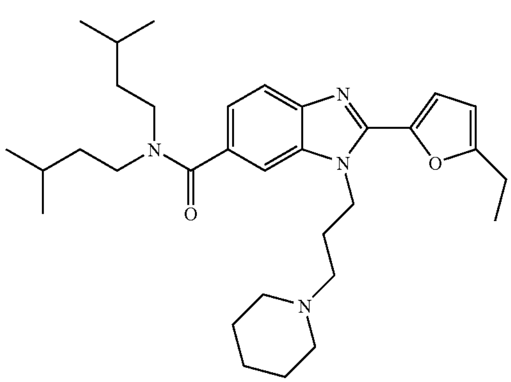 | 521.3 | 9.0 |

-continued

| Examples | Molecular Structures | [M & H]+ | rt (min) |
|---|---|---|---|
| 149 | 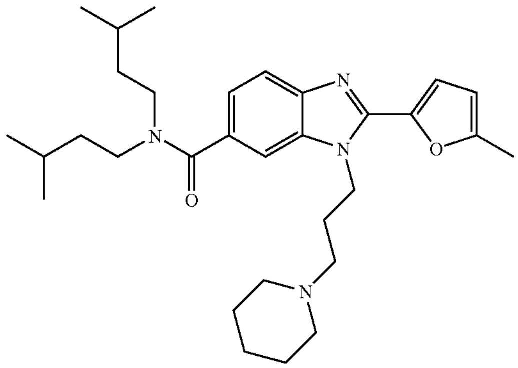 | 507.3 | 8.8 |
| 150 | 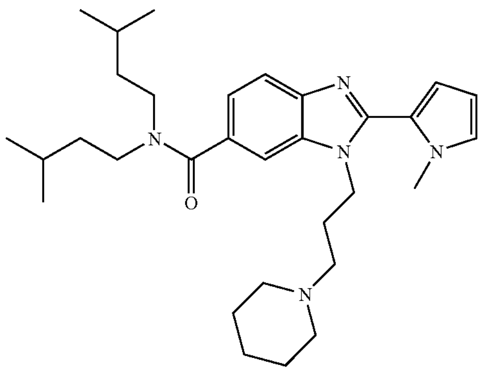 | 506.3 | 8.8 |
| 151 | 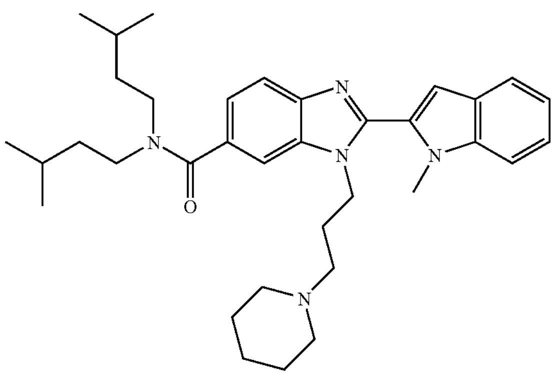 | 556.3 | 9.6 |
| 152 | 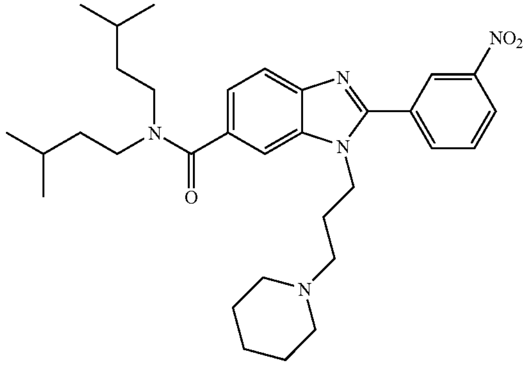 | 548.3 | 9.2 |

-continued

| Examples | Molecular Structures | [M & H]+ | rt (min) |
|---|---|---|---|
| 153 | 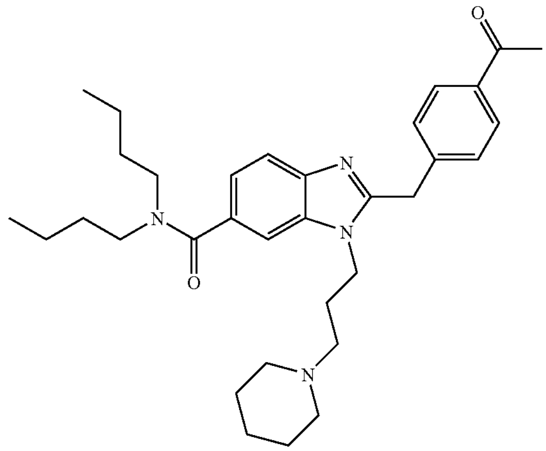 | 531.3 | 8.3 |
| 154 | 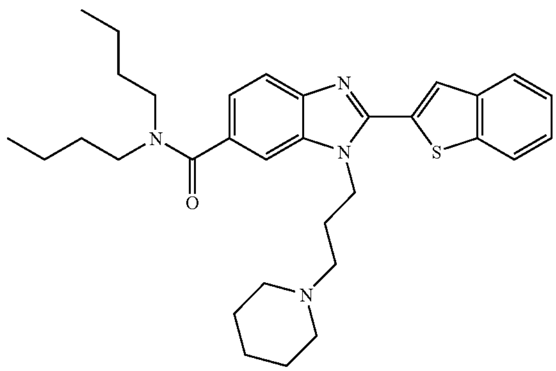 | 531.3 | 9.3 |
| 155 | 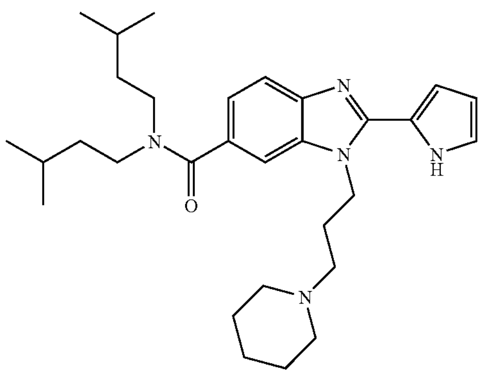 | 492.3 | 8.6 |
| 156 | 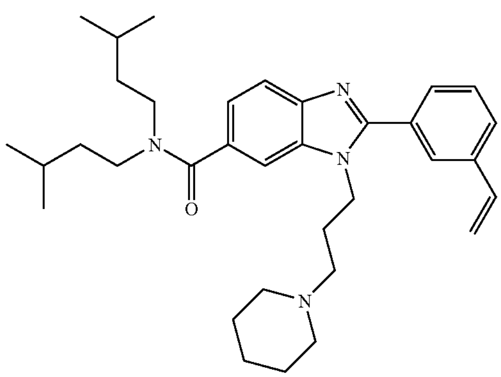 | 529.4 | 9.0 |

-continued
| Examples | Molecular Structures | [M & H]+ | rt (min) |
|---|---|---|---|
| 157 | 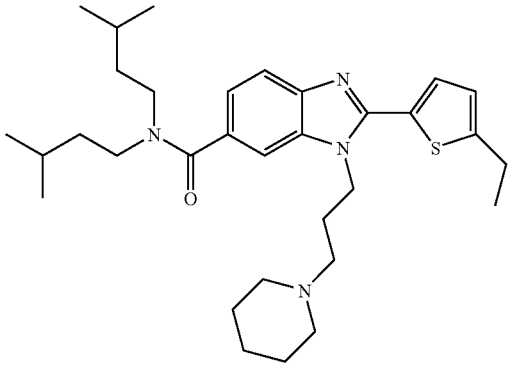 | 537.3 | 9.3 |
| 158 | 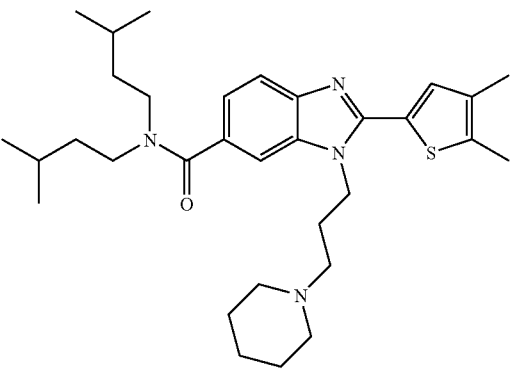 | 537.3 | 9.2 |
| 159 | 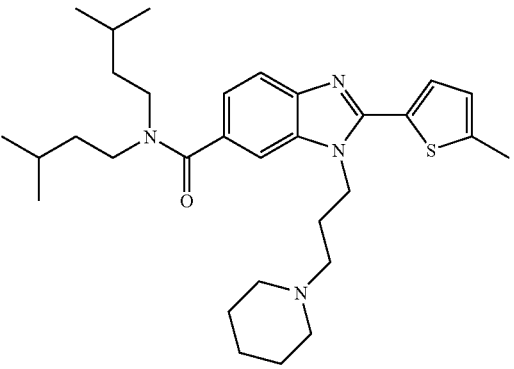 | 523.3 | 9.1 |
| 160 | 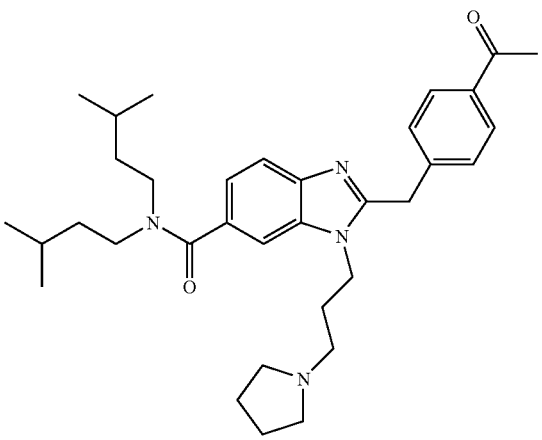 | 545.3 | 8.6 |

| Examples | Molecular Structures | [M & H]+ | rt (min) |
|---|---|---|---|
| 161 | 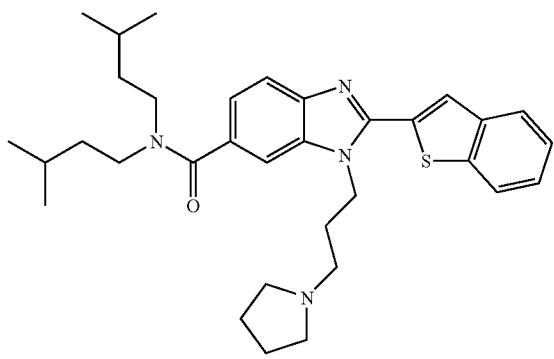 | 545.3 | 9.6 |
| 162 | 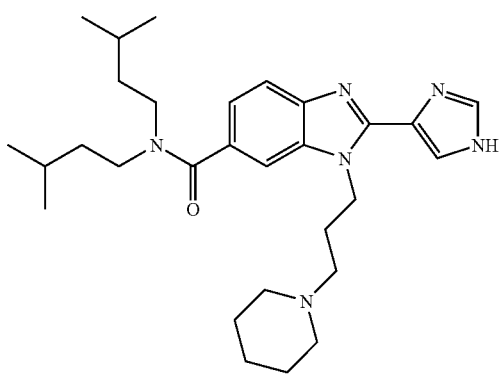 | 493.3 | 8.2 |
| 163 | 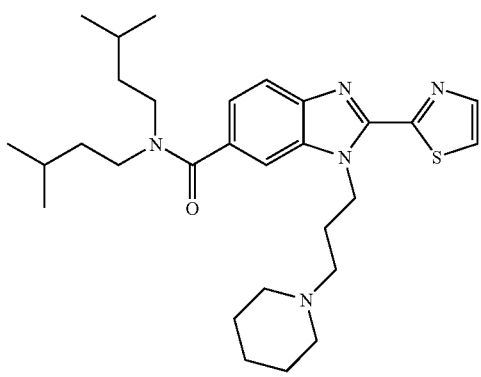 | 510.3 | 9.3 |
| 164 | 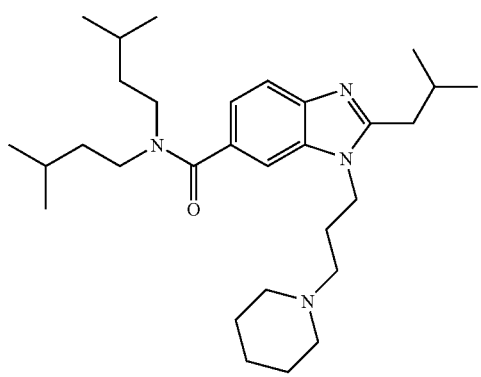 | 483.4 | 8.2 |

-continued

| Examples | Molecular Structures | [M & H]+ | rt (min) |
|---|---|---|---|
| 165 | 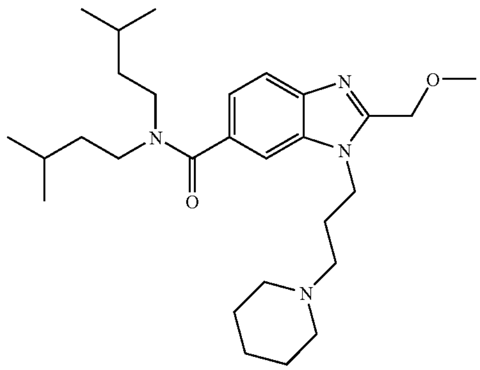 | 471.3 | 8.4 |
| 166 | 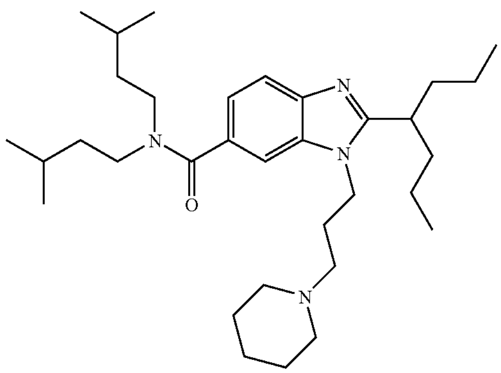 | 525.4 | 8.6 |
| 167 | 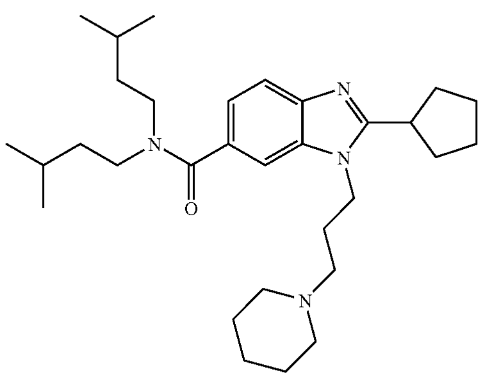 | 495.4 | 8.2 |
| 168 | 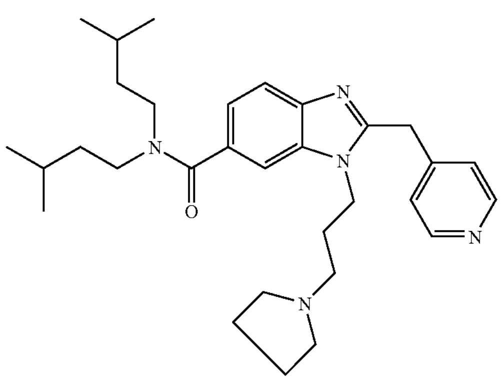 | 504.3 | 8.0 |

-continued
| Examples | Molecular Structures | [M & H]+ | rt (min) |
|---|---|---|---|
| 169 | 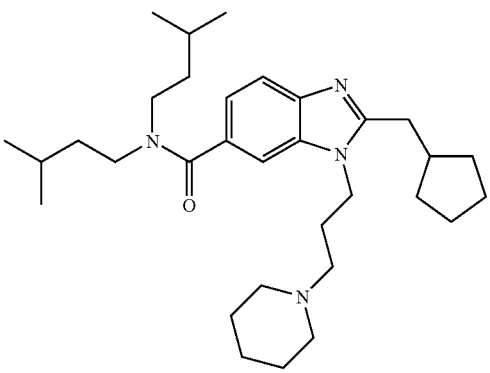 | 509.4 | 8.3 |
| 170 | 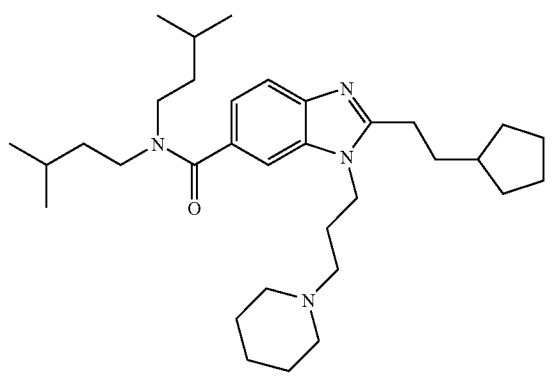 | 523.4 | 8.5 |
| 171 | 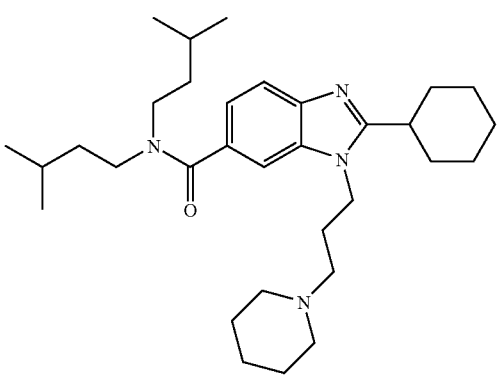 | 509.4 | 8.3 |
| 172 | 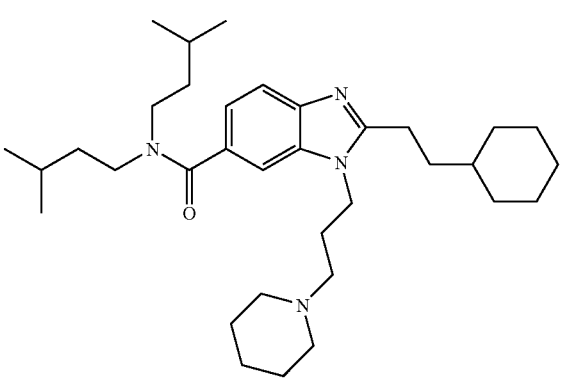 | 537.4 | 8.6 |

| Examples | Molecular Structures | [M & H]+ | rt (min) |
|---|---|---|---|
| 173 | 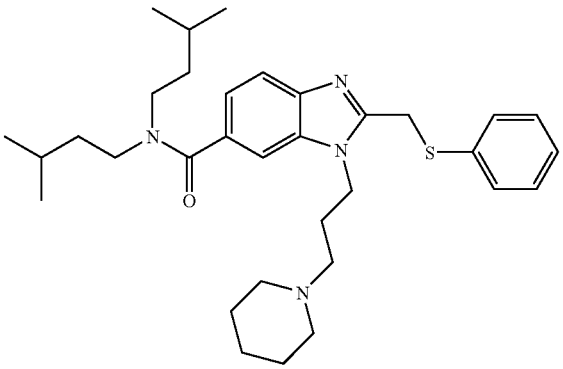 | 549.3 | 9.0 |
| 174 | 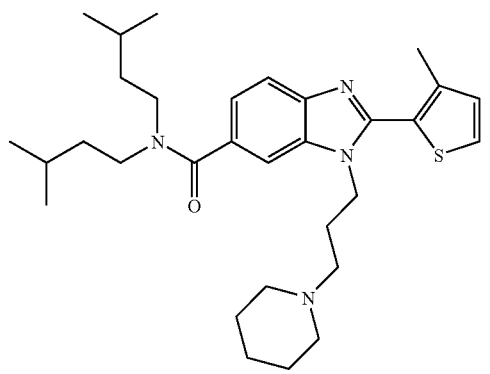 | 523.3 | 8.9 |
| 175 | 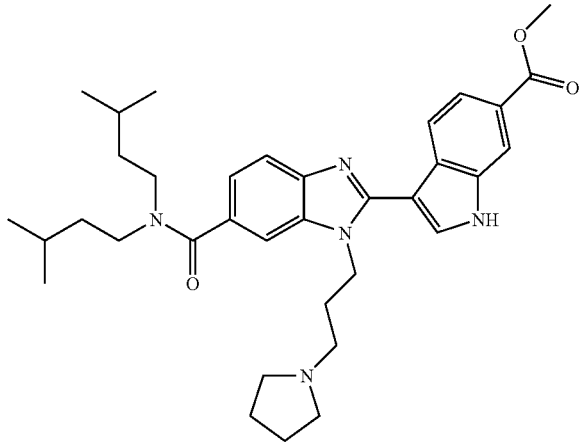 | 586.3 | 8.4 |
| 176 | 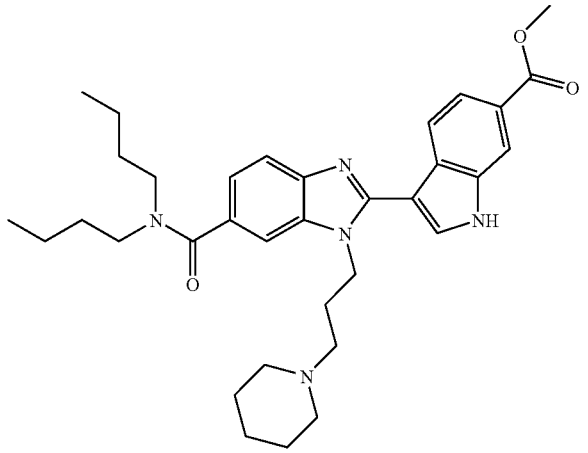 | 572.3 | 8.1 |

-continued
| Examples | Molecular Structures | [M & H]+ | rt (min) |
|---|---|---|---|
| 177 | 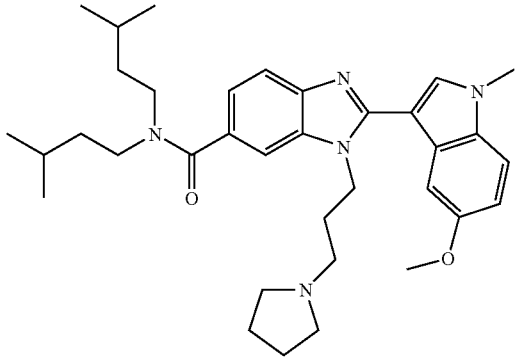 | 572.3 | 8.3 |
| 178 | 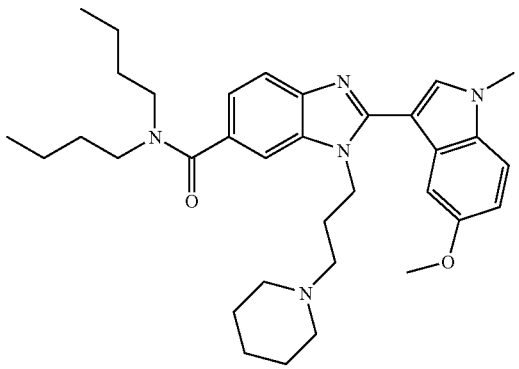 | 558.3 | 8.1 |
| 179 | 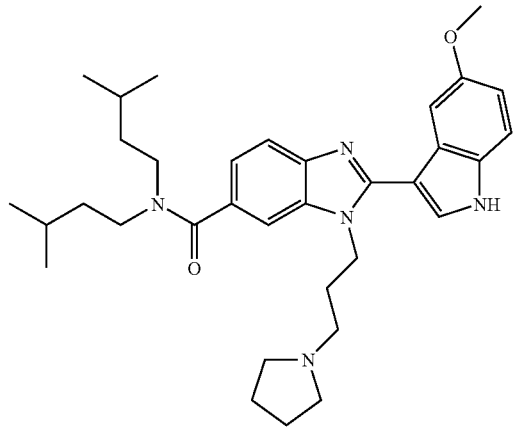 | 558.3 | 8.2 |
| 180 | 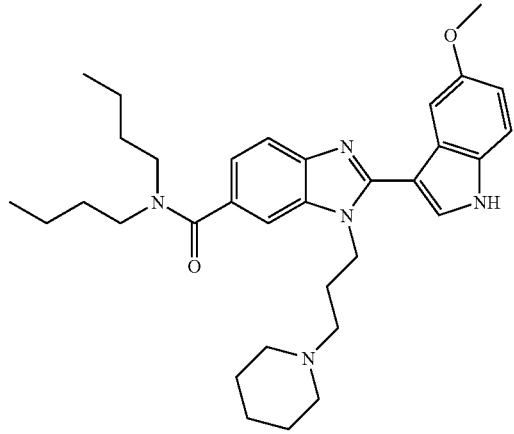 | 544.3 | 8.0 |

-continued

| Examples | Molecular Structures | [M & H]+ | rt (min) |
|---|---|---|---|
| 181 | 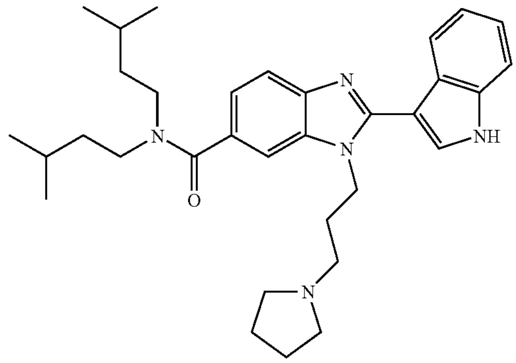 | 528.3 | 8.2 |
| 182 | 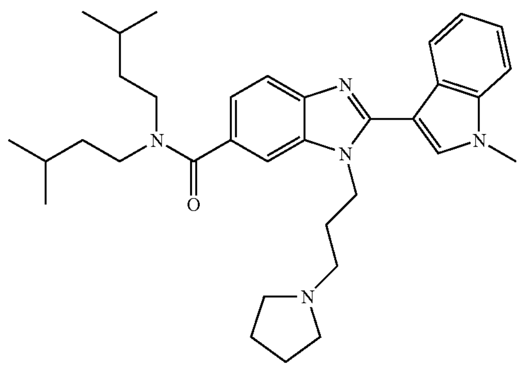 | 542.3 | 8.4 |
| 183 | 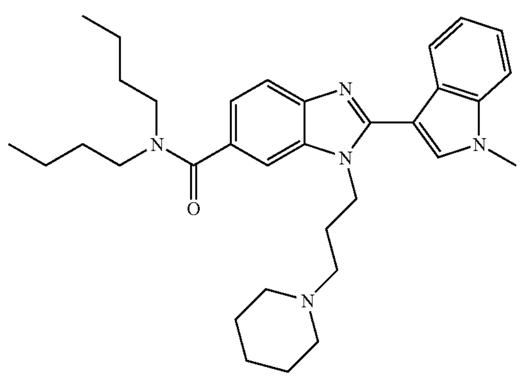 | 528.3 | 8.2 |
| 184 | 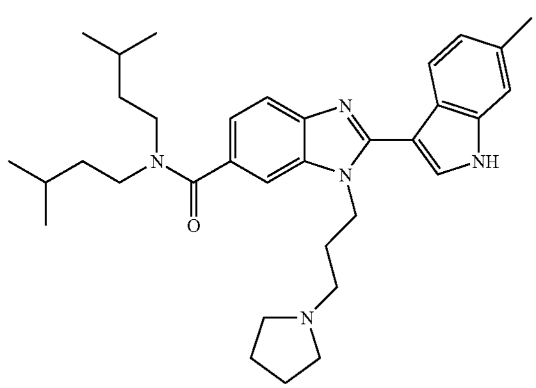 | 542.3 | 8.4 |

-continued
| Examples | Molecular Structures | [M & H]+ | rt (min) |
|---|---|---|---|
| 185 | 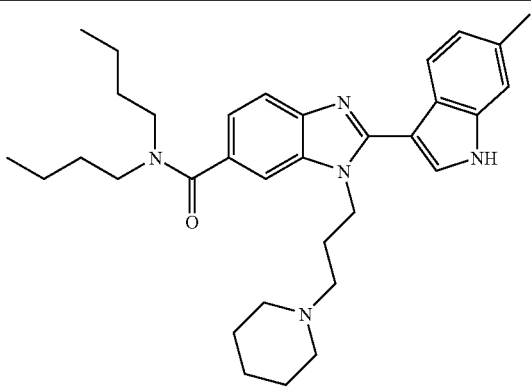 | 528.3 | 8.2 |
| 186 | 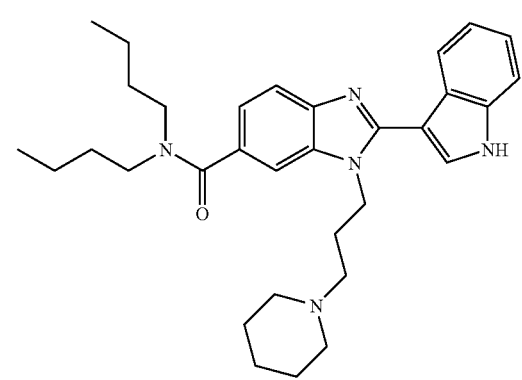 | 514.3 | 8.1 |
| 187 | 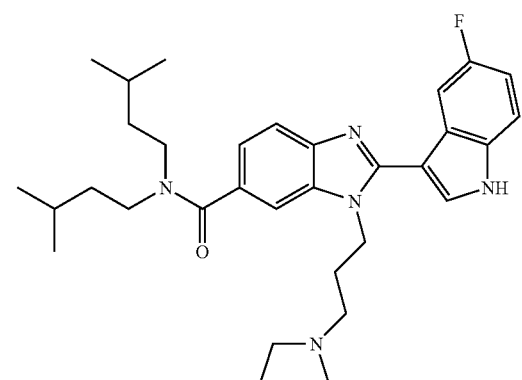 | 546.3 | 8.5 |
| 188 | 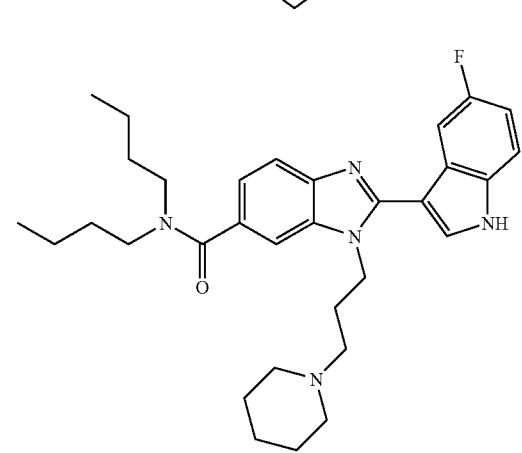 | 532.3 | 8.2 |

-continued

| Examples | Molecular Structures | [M & H]+ | rt (min) |
|---|---|---|---|
| 189 | 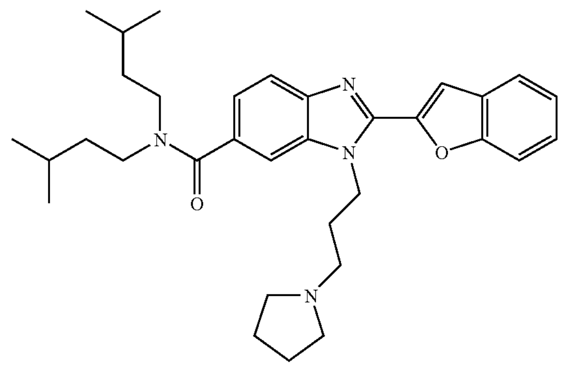 | 529.3 | 9.5 |
| 190 | 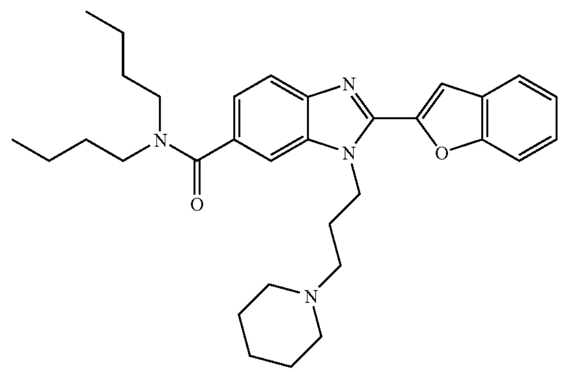 | 515.3 | 9.1 |
| 191 | 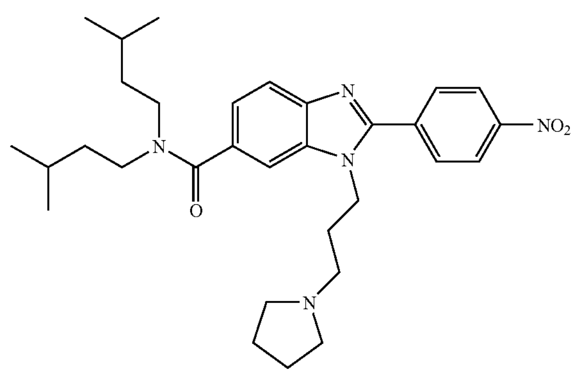 | 534.3 | 9.2 |
| 192 | 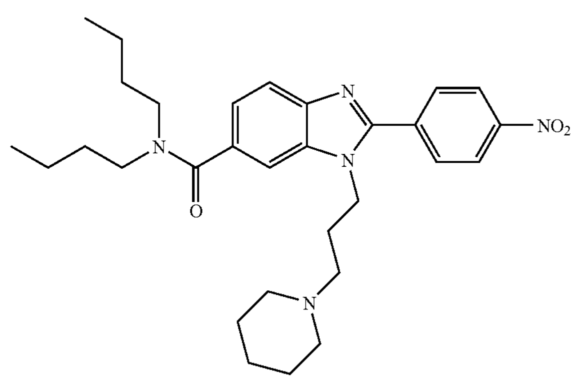 | 520.3 | 8.8 |

-continued
| Examples | Molecular Structures | [M & H]+ | rt (min) |
|---|---|---|---|
| 193 | 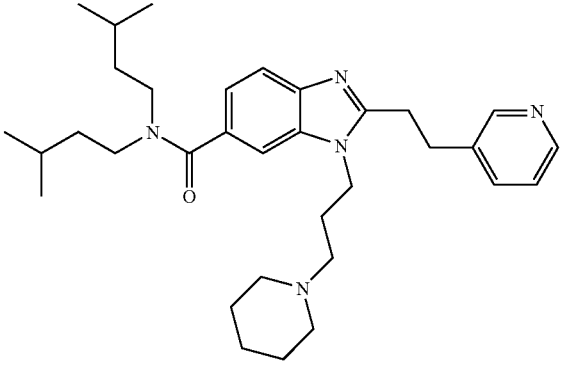 | 532.3 | 8.0 |
| 194 | 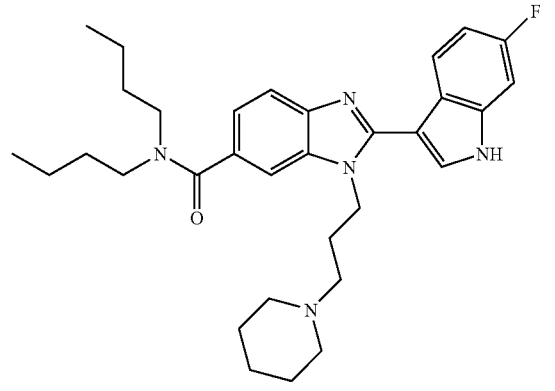 | 532.3 | 8.2 |
| 195 | 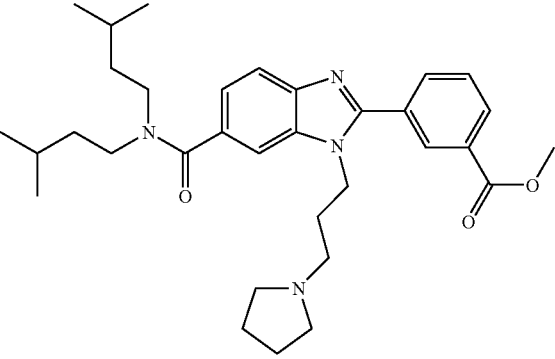 | 547.3 | 8.9 |
| 196 | 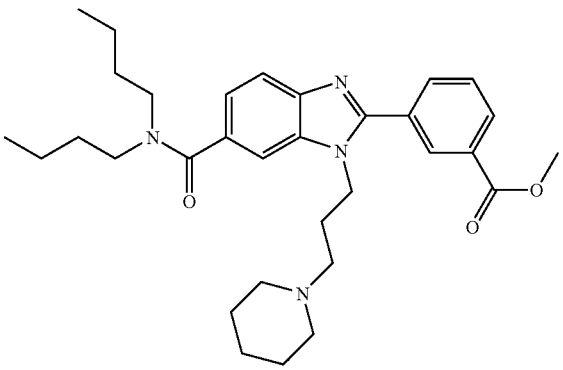 | 533.3 | 8.6 |

-continued

| Examples | Molecular Structures | [M & H]+ | rt (min) |
|---|---|---|---|
| 197 | 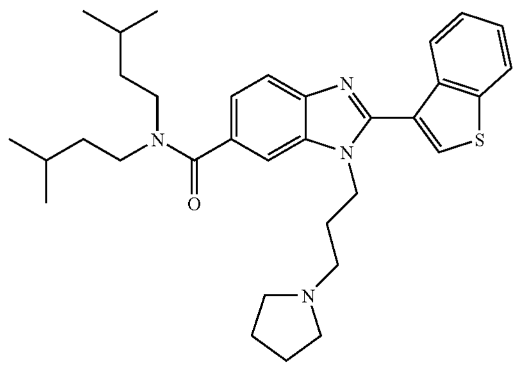 | 545.2 | 9.2 |
| 198 | 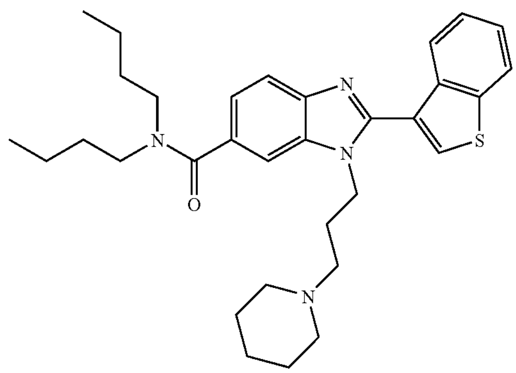 | 531.2 | 8.8 |
| 199 | 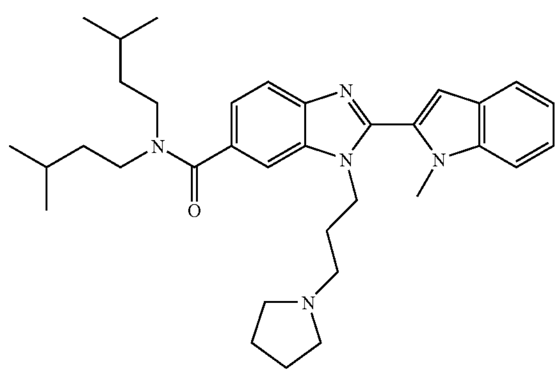 | 542.3 | 9.5 |
| 200 | 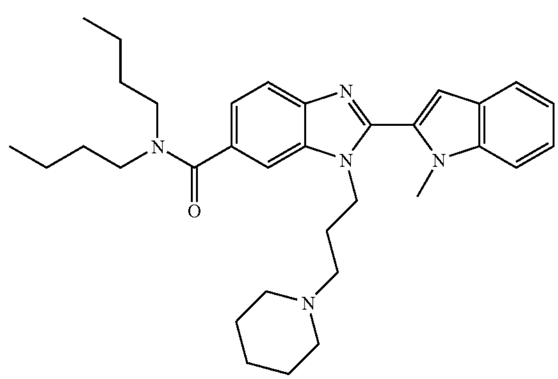 | 528.3 | 9.2 |

-continued
| Examples | Molecular Structures | [M & H]+ | rt (min) |
|---|---|---|---|
| 201 | 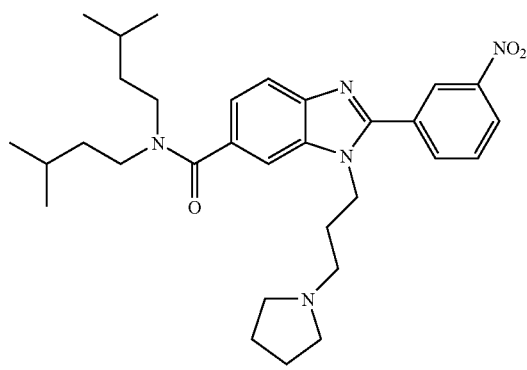 | 534.2 | 9.1 |
| 202 | 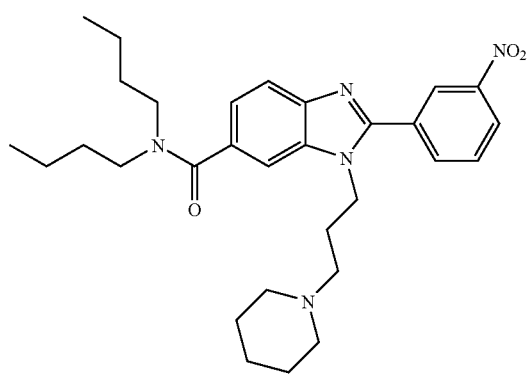 | 520.2 | 8.8 |
| 203 | 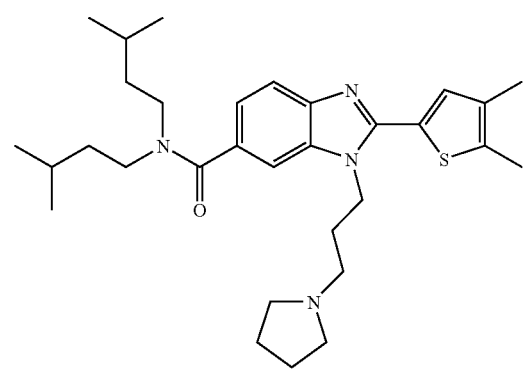 | 523.3 | 9.1 |
| 204 | 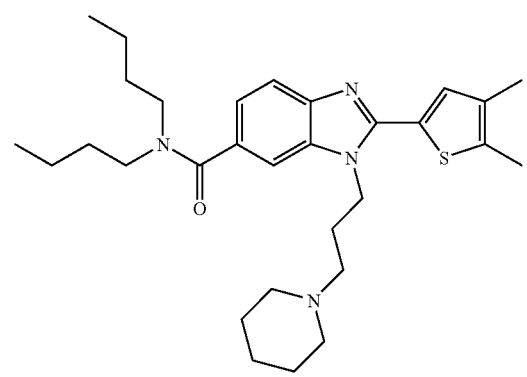 | 509.3 | 8.7 |

| Examples | Molecular Structures | [M & H]+ | rt (min) |
|---|---|---|---|
| 205 | 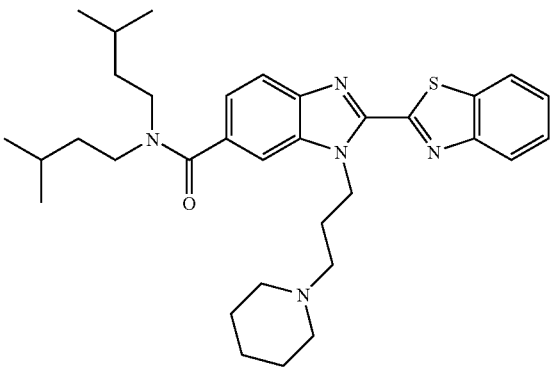 | 560.2 | 10.1 |
| 206 | 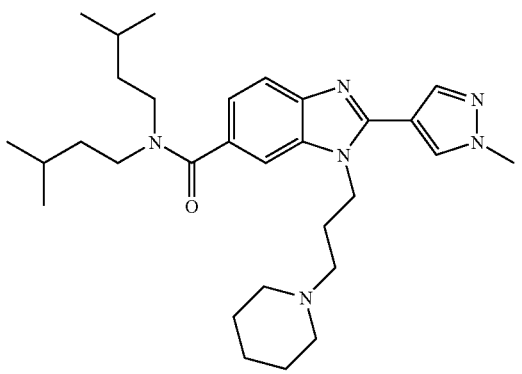 | 507.3 | 8.3 |
| 207 | 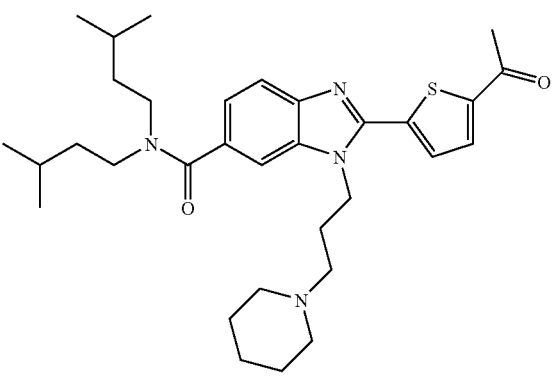 | 551.3 | 9.2 |
| 208 | 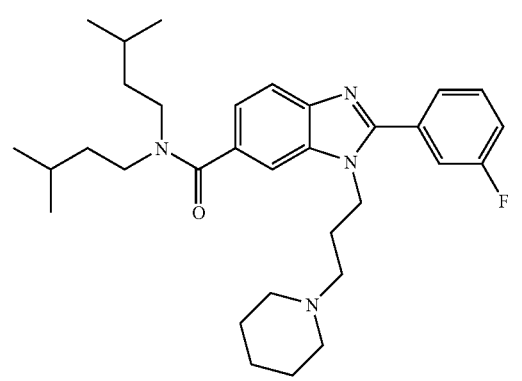 | 521.3 | 9.1 |

-continued

| Examples | Molecular Structures | [M & H]+ | rt (min) |
|---|---|---|---|
| 209 | 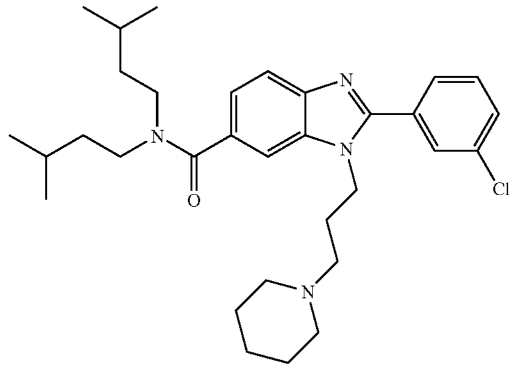 | 537.3 | 9.3 |
| 210 | 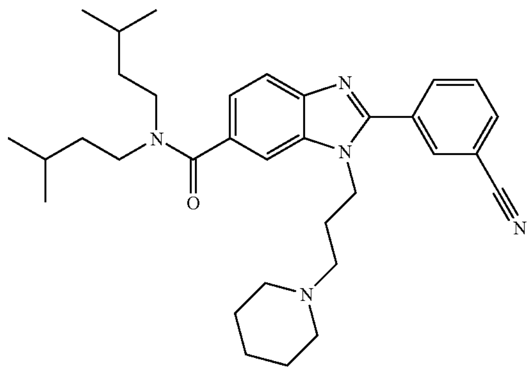 | 528.3 | 9.1 |
| 211 | 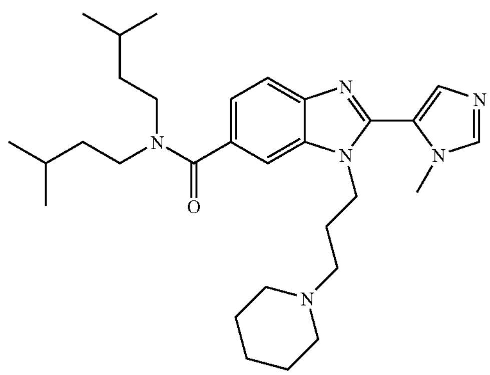 | 507.5 | 8.1 |
| 212 | 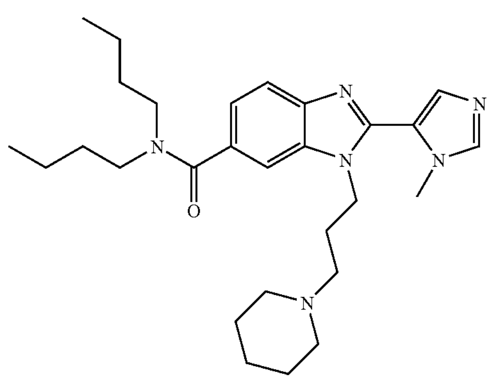 | 479.4 | 7.8 |

-continued

| Examples | Molecular Structures | [M & H]+ | rt (min) |
|---|---|---|---|
| 213 | 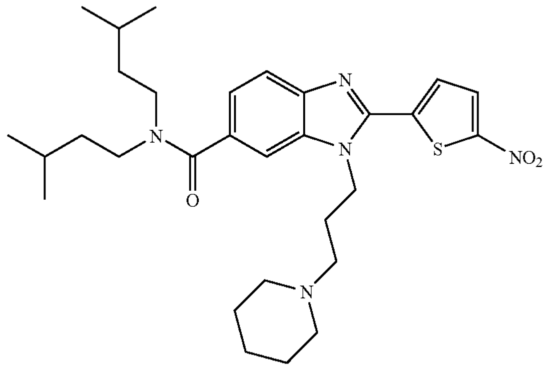 | 554.4 | 9.7 |
| 214 | 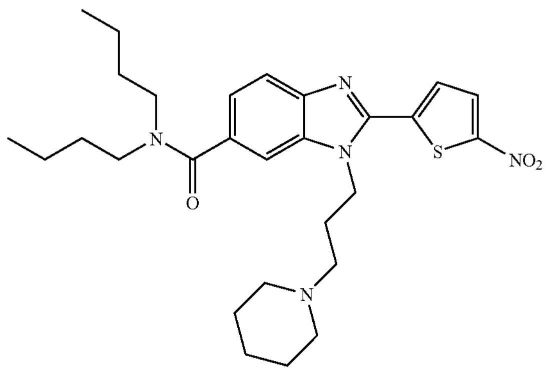 | 526.4 | 9.2 |
| 215 | 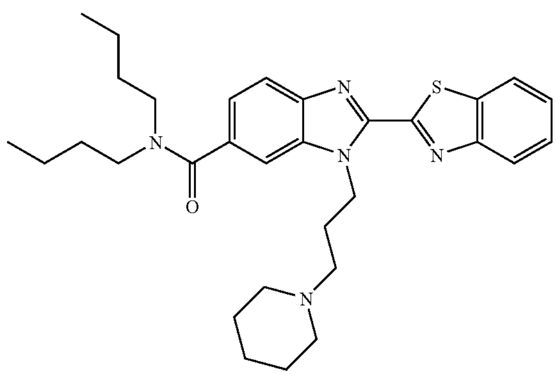 | 532.4 | 9.7 |
| 216 | 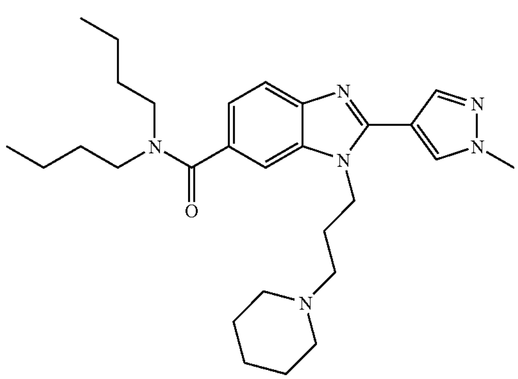 | 479.4 | 7.9 |

-continued
| Examples | Molecular Structures | [M & H]+ | rt (min) |
|---|---|---|---|
| 217 | 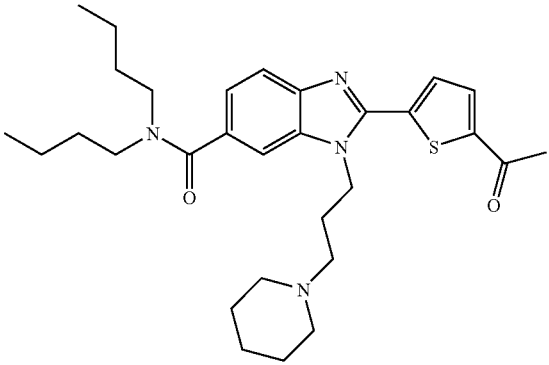 | 523.4 | 8.8 |
| 218 | 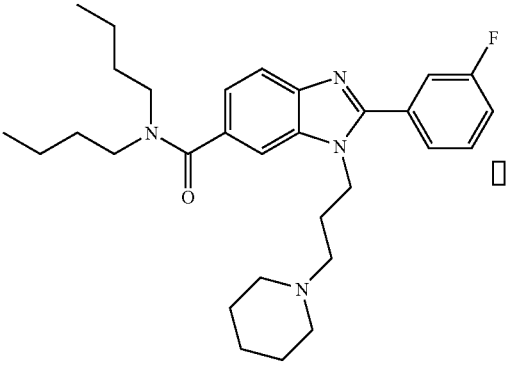 | 493.4 | 8.6 |
| 219 | 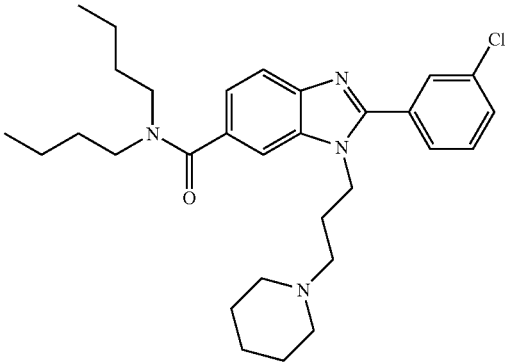 | 509.4 | 8.8 |
| 220 | 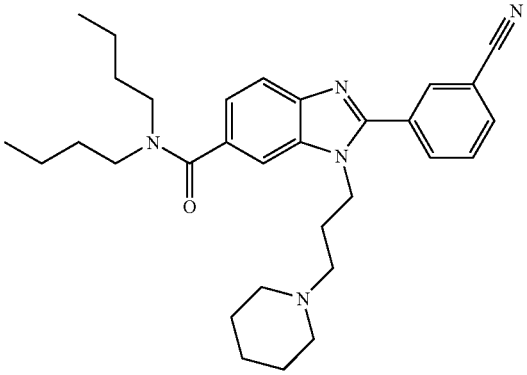 | 500.5 | 8.7 |

-continued

| Examples | Molecular Structures | [M & H]+ | rt (min) |
|---|---|---|---|
| 221 | 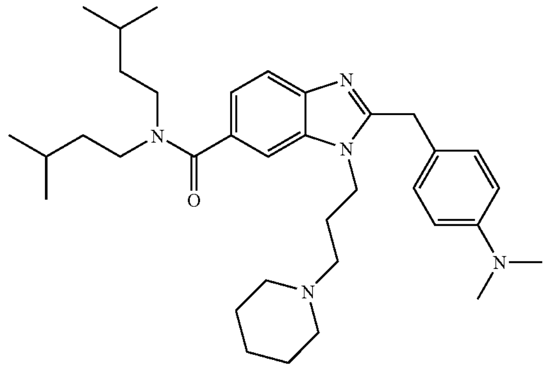 | 560.5 | 8.4 |
| 222 | 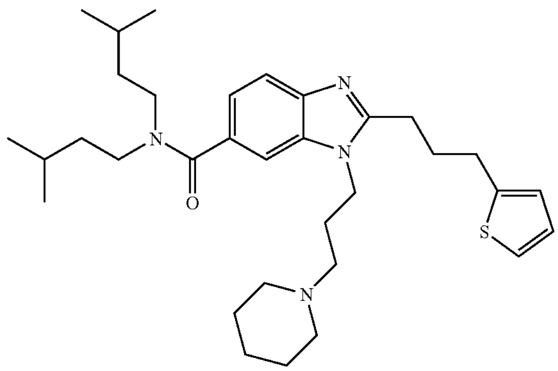 | 551.5 | 8.7 |
| 223 | 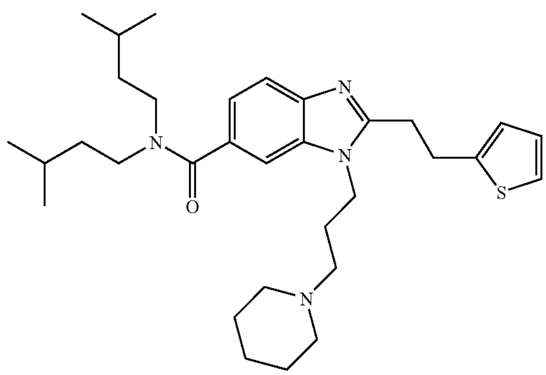 | 537.5 | 8.7 |
| 224 | 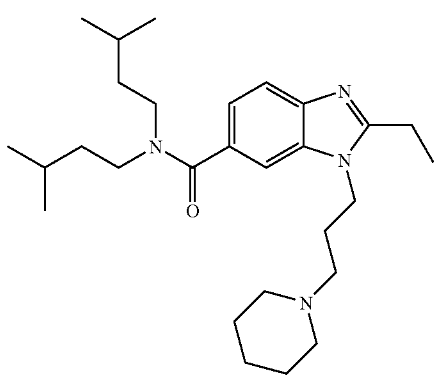 | 455.5 | 8.0 |

| Examples | Molecular Structures | [M & H]+ | rt (min) |
|---|---|---|---|
| 225 | 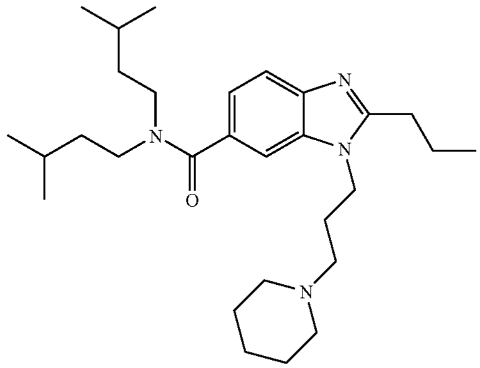 | 469.5 | 8.1 |
| 226 | 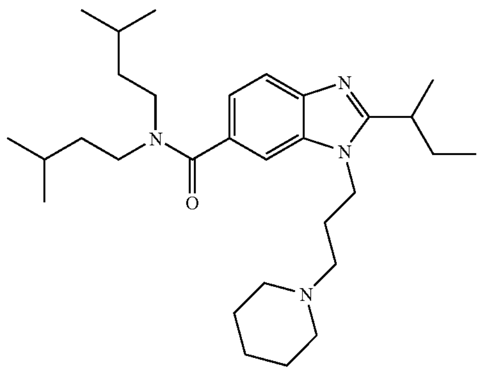 | 483.5 | 8.2 |
| 227 | 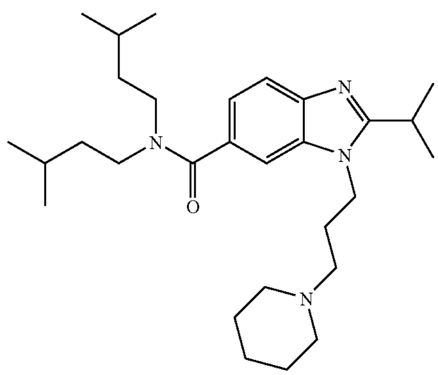 | 469.5 | 8.1 |
| 228 | 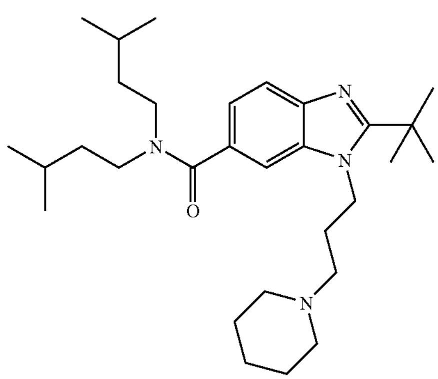 | 483.5 | 8.2 |

-continued

| Examples | Molecular Structures | [M & H]+ | rt (min) |
|---|---|---|---|
| 229 | 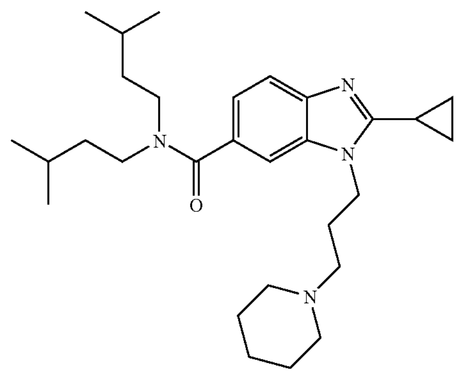 | 467.5 | 8.1 |
| 230 | 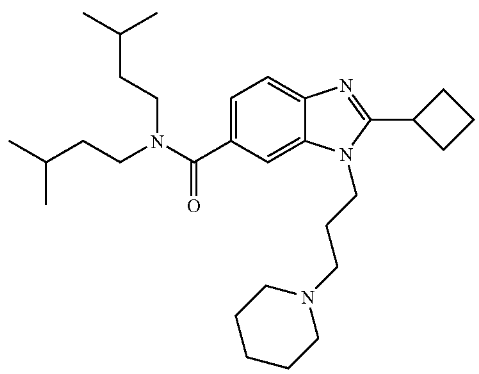 | 481.4 | 8.2 |
| 231 | 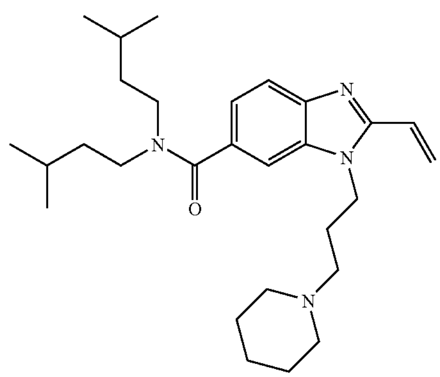 | 453.4 | 8.3 |
| 232 | 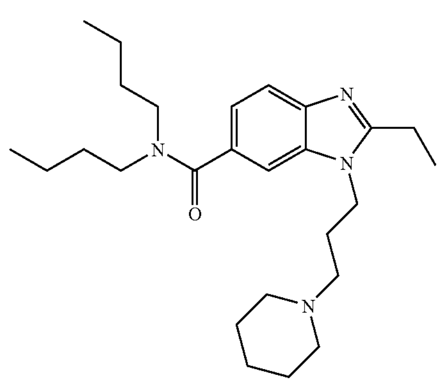 | 427.4 | 7.8 |

-continued

| Examples | Molecular Structures | [M & H]+ | rt (min) |
|---|---|---|---|
| 233 | 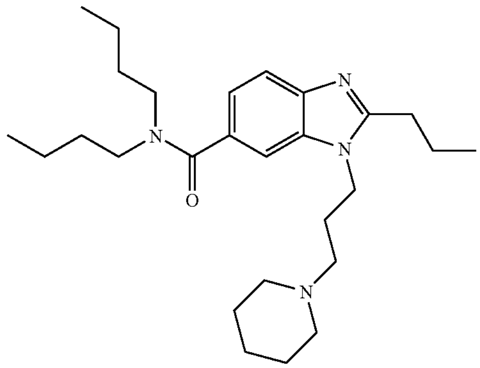 | 441.4 | 7.8 |
| 234 | 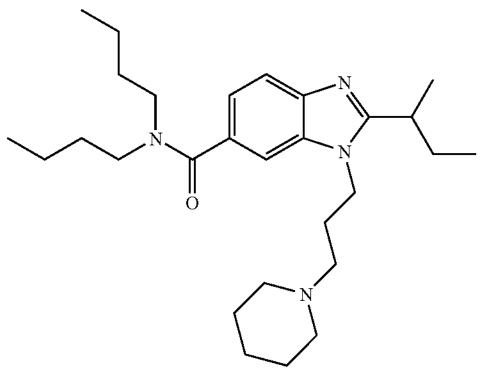 | 455.4 | 7.9 |
| 235 | 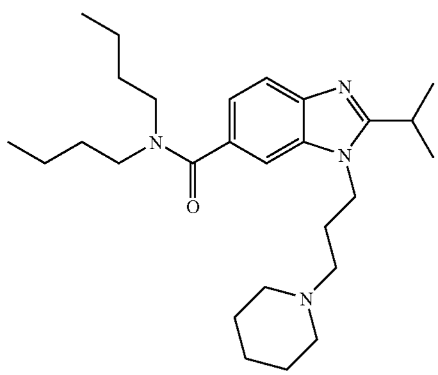 | 441.4 | 7.8 |
| 236 | 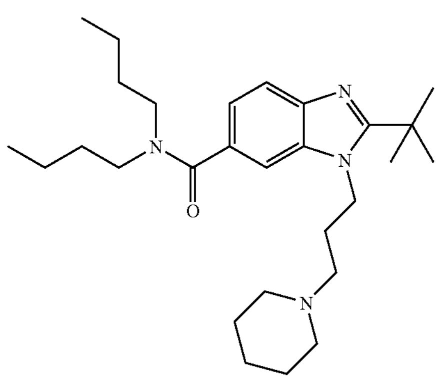 | 455.4 | 7.9 |

-continued

| Examples | Molecular Structures | [M & H]+ | rt (min) |
|---|---|---|---|
| 237 | 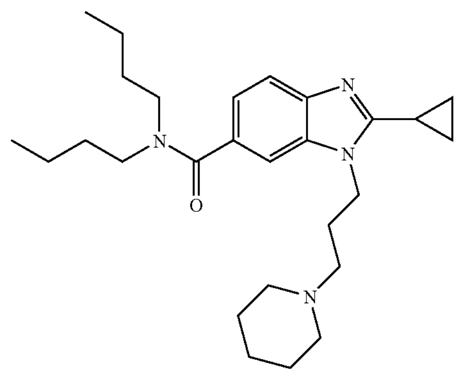 | 439.4 | 7.8 |
| 238 | 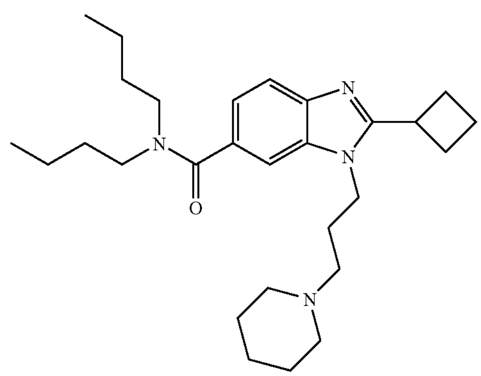 | 453.4 | 7.9 |
| 239 | 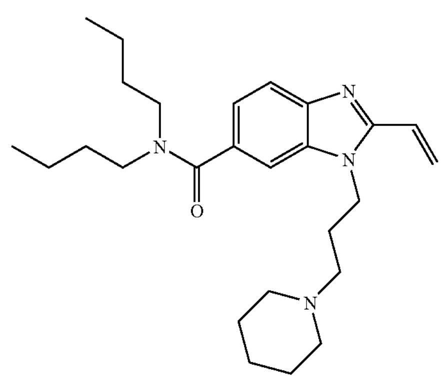 | 425.3 | 8.0 |
| 240 | 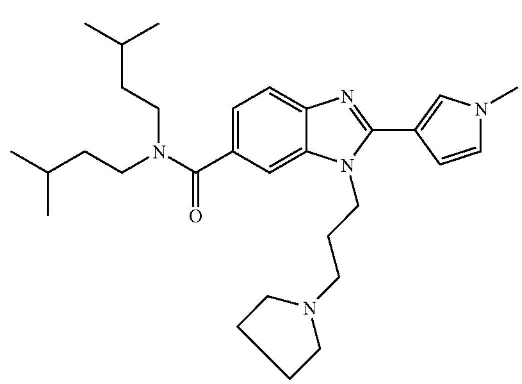 | 492.4 | 8.1 |

| Examples | Molecular Structures | [M & H]+ | rt (min) |
|---|---|---|---|
| 241 | 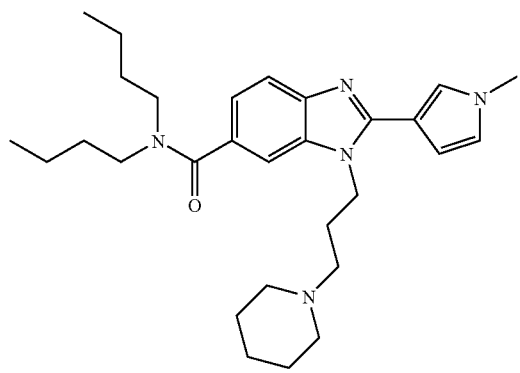 | 478.4 | 7.8 |
| 242 | 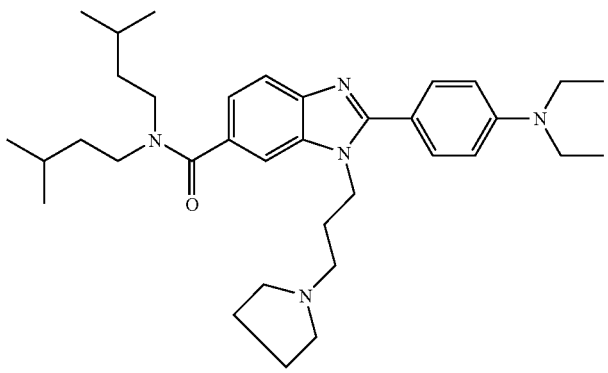 | 560.5 | 8.4 |
| 243 | 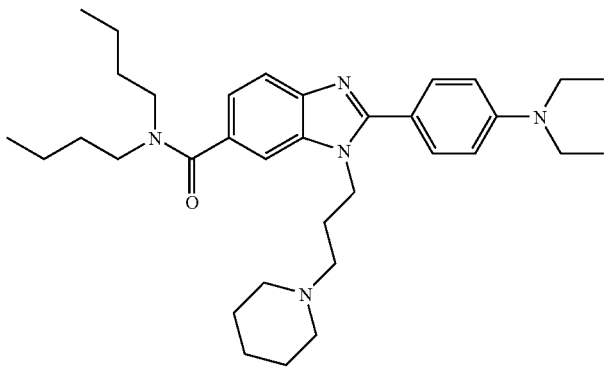 | 546.4 | 8.2 |
| 244 | 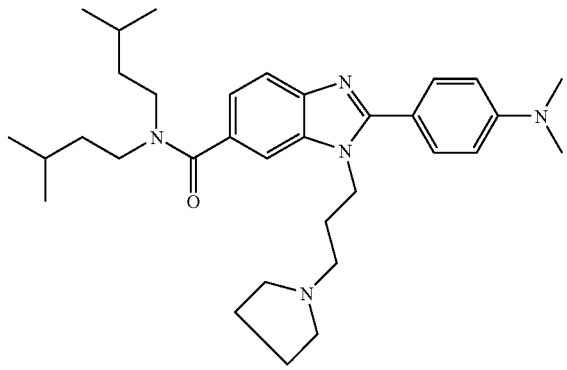 | 532.4 | 8.2 |

-continued
| Examples | Molecular Structures | [M & H]+ | rt (min) |
|---|---|---|---|
| 245 | 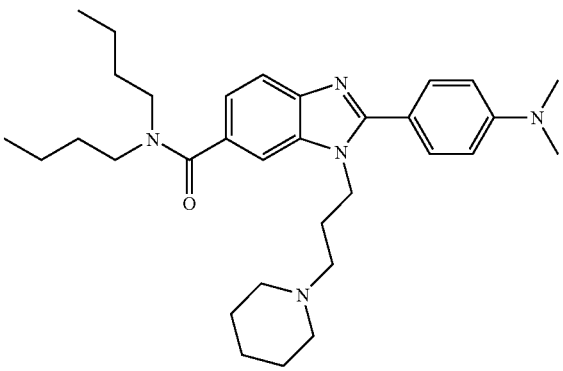 | 518.4 | 8.0 |
| 246 | 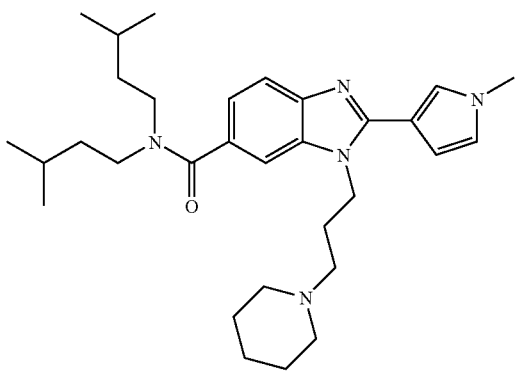 | 506.4 | 8.2 |
| 247 | 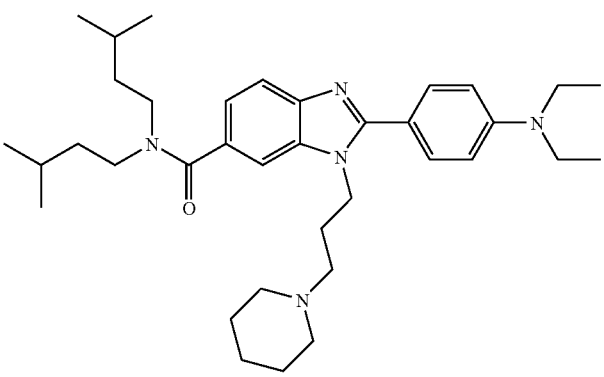 | 574.4 | 8.5 |
| 248 | 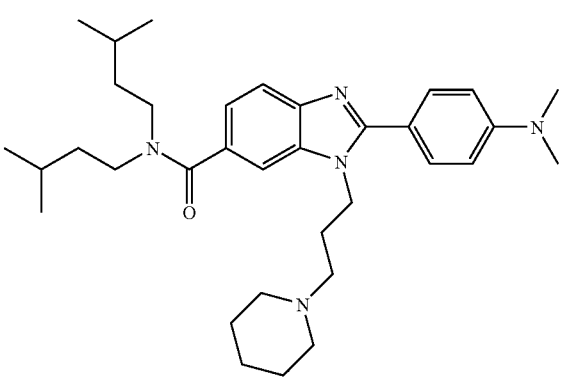 | 546.4 | 8.3 |

| Examples | Molecular Structures | [M & H]+ | rt (min) |
|---|---|---|---|
| 249 | 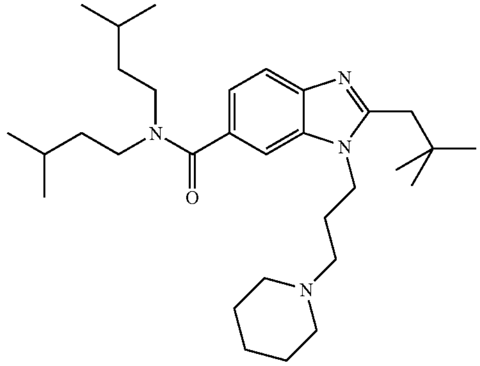 | 497.5 | 8.4 |
| 250 | 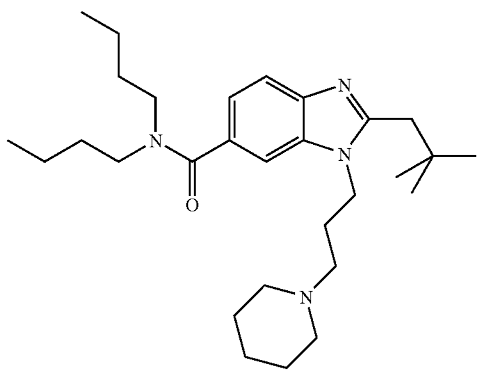 | 469.5 | 8.1 |

Pharmacological Study

The affinity of the compounds of the present invention for the different sub-types of melanocortin receptors was measured according to procedures analogous to those described below for the MC4 receptors.

Study of the Affinity of the Compounds for the MC4 Receptors of Melanocortins:

The affinity of the compounds of the invention for the MC4 receptors is determined by measuring the inhibition of the binding of [$^{125}$I]-[Nle$^3$, D-Phe$^7$]-α-MSH to membrane preparations of transfected CHO-K1 cells.

The CHO-K1 cells expressing in a stable fashion the human MC4 receptors are cultured in an RPMI 1640 medium containing 10% of fœtal calf serum, 2 mM of glutamine, 100 U/ml of penicillin, 0.1 mg/ml of streptomycin and 0.5 mg/ml of G418. The cells are collected with 0.5 mM of EDTA and centrifuged at 500 g for 5 minutes at 4° C. The pellet is resuspended in a phosphate buffered saline (PBS) medium and centrifuged at 500 g for 5 minutes at 4° C. The pellet is resuspended in a Tris 50 mM buffer medium at pH 7.4 and centrifuged at 500 g for 5 minutes at 4° C. The cells are lysed by sonication and centrifuged at 39,000 g for 10 minutes at 4° C. The cells are lysed by sonication and centrifuged at 39,000 g for 10 minutes at 4° C. The pellet is resuspended in the Tris 50 mM buffer medium at pH 7.4 and centrifuged at 50,000 g for 10 min at 4° C. The membranes obtained in this last pellet are stored at −80° C.

The measurement of the competitive inhibition of the binding of [$^{125}$I]-[Nle$^4$, D-Phe$^7$]-αMSH (Amersham Biosciences) to the MC4 receptors is carried out in duplicate using polypropylene 96-well plates. The cell membranes (50 μg of proteins/well) are incubated with [$^{125}$I]-[Nle$^4$, D-Phe$^7$]-α-MSH(0.5 nM) for 90 minutes at 37° C. in a Tris-HCl 50 mM buffer medium, pH 7.4, comprising 0.2% of bovine serum albumin (BSA), 5 mM of MgCl$_2$ and 0.1 mg/ml of bacitracin.

The bonded [$^{125}$I]-[Nle$^4$, D-Phe$^7$]-α-MSH is separated from the free [$^{125}$I]-[Nle$^4$, D-Phe$^7$]-α-MSH by filtration through GF/C glass fibre filters (Unifilter, PerkinElmer) pre-impregnated with 0.1% of polyethylenimine (P.E.I.), using a filtermate 196 (PerkinElmer). The filters are washed with Tris-HCl 50 mM buffer, pH 7.4 at 0-4° C. and the radioactivity present is determined using a counter (Top Count, PerkinElmer).

The specific binding is obtained by subtracting the non-specific binding (determined in the presence of 0.1 μM of Nle$^4$, D-Phe$^7$-α-MSH) from the total binding. The data are analyzed by computer-aided non-linear regression (MDL) and the values of the inhibition constants (Ki) are determined.

The agonist or antagonist activity of the MC4 receptors of the compounds of the present invention was determined by measuring the production of cyclic AMP by the CHO-K1 cells transfected by the MC4 receptor.

Measurement of the Production of Intracellular Cyclic Amp Via the MC4 Receptors:

The CHO-K1 cells expressing the MC4 receptors of the melanocortins are cultured in 384-well plates in an RPMI 1640 medium with 10% of fœtal calf serum and 0.5 mg/ml of G418. The cells are washed twice with 50 μl of RPMI medium comprising 0.2% BSA and 0.5 mM of 3-isobutyl-1-methylxanthine (IBMX).

In order to measure the agonist effect of a compound, the cells are incubated for 5 minutes at 37° C. in the presence of 0.5 mM of IBMX, then stimulation of the production of cyclic AMP is obtained by adding the compound at concentrations comprised between 1 pM and 10 μM in duplicate for 20 minutes at 37° C. The antagonist effect of a compounds is measured by inhibiting stimulation of the production of cyclic AMP induced by Nle⁴, D-Phe⁷-α-MSH at concentrations comprised between 1 pM and 10 μm, in the presence of the compound to be tested, at concentrations comprised between 1 nM and 10 μM in duplicate for 20 minutes at 37° C.

The reaction medium is eliminated and 80 μl of lysis buffer is added. The intracellular cyclic AMP level is measured by a competition test with fluorescent cyclic AMP (CatchPoint, Molecular Devices).

The tests carried out according to the protocols described above have made it possible to show that the products according to the present invention have a good affinity for the MC4 receptors, the inhibition constant $K_i$ on these receptors being less than the micromolar for the majority of the compounds exemplified.

The invention claimed is:

1. Compound of general formula (I)

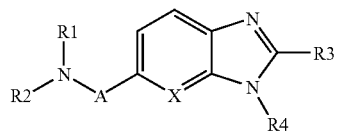
(I)

in racemic, enantiomeric form or any combinations thereof and in which:

A represents —CH$_2$—, —C(O)—, or —C(O)—C(R$_a$)(R$_b$)—;

X represents a —CH— radical or a nitrogen atom;

R$_a$ and R$_b$ represent, independently, a hydrogen atom or a (C$_1$-C$_6$)alkyl radical;

R$_1$ represents a hydrogen atom or a (C$_1$-C$_8$)alkyl radical;

R$_2$ represents a (C$_1$-C$_8$)alkyl radical;

or R$_1$ and R$_2$ form together with the nitrogen atom to which they are attached, a heterobicycloalkyl or a heterocycloalkyl optionally substituted by one or more identical or different (C$_1$-C$_6$)alkyl substituents;

R$_3$ represents —(CH$_2$)$_p$—Z$_3$;

Z$_3$ represents a heteroaryl radical, Z$_3$ being linked to the —(CH$_2$)$_p$— radical by a carbon atom;

the heteroaryl radical being optionally substituted by one or more identical or different substituents including halo, nitro or —(CH$_2$)$_p$-V$_{30}$—Y$_3$ where V$_{30}$ represents —O—, —C(O)—, —C(O)—O— or a covalent bond;

Y$_3$ represents a hydrogen atom or a (C$_1$-C$_6$)alkyl radical optionally substituted by one or more identical or different halo radicals p' represents an integer from 0 to 4; and R$_4$ represents a radical of formula —(CH$_2$)$_s$—R'$_4$, where R'$_4$ represents a heterocycloalkyl containing at least one nitrogen atom and optionally substituted by (C$_1$-C$_6$) alkyl and s represents an integer from 2 to 6;

or a pharmaceutically acceptable salt thereof.

2. Compound according to claim 1, wherein X represents the —CH— radical; or a pharmaceutically acceptable salt thereof.

3. Compound according to claim 1, wherein R$_1$ represents the hydrogen atom or a (C$_1$-C$_8$)alkyl radical, and R$_2$ represents a (C$_1$-C$_8$)alkyl radical; or a pharmaceutically acceptable salt thereof.

4. Compound according to claim 1, wherein R$_1$ represents a (C$_1$-C$_6$)alkyl radical; R$_2$ represents a (C$_1$-C$_6$)alkyl radical; or a pharmaceutically acceptable salt thereof.

5. Compound according to claim 1, wherein A represents —CH$_2$—; or a pharmaceutically acceptable salt thereof.

6. Compound according to claim 1, wherein A represents —C(O)—C(R$_a$)(R$_b$)— and R$_a$ and R$_b$, represent, independently, a methyl radical; or a pharmaceutically acceptable salt thereof.

7. Compound according to claim 1, wherein A represents —C(O)—; or a pharmaceutically acceptable salt thereof.

8. Compound according to claim 1, wherein R'$_4$ represents a piperidine or pyrrolidine ring; s represents an integer from 1 to 4; or a pharmaceutically acceptable salt thereof.

9. Compound according to claim 1, wherein

V$_{30}$ represents —O—, —C(O)—, —C(O)—O— or a covalent bond; and

Y$_3$ represents a (C$_1$-C$_6$)alkyl radical;

or a pharmaceutically acceptable salt thereof.

10. Compound according to claim 1, wherein Z$_3$ represents a thienyl, furyl, benzofuryl, benzothienyl, thiazolyl, pyrazolyl, imidazolyl, pyridinyl, indolyl radical; or a pharmaceutically acceptable salt thereof.

11. Pharmaceutical composition comprising, as an active ingredient, at least one compound according to claim 1, in combination with a pharmaceutically acceptable support.

12. Process for the preparation of a compound of formula (I) according to claim 1, comprising treating a compound of general formula:

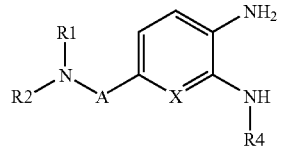

in which A, X, R$_1$, R$_2$, R$_4$ have the meaning indicated in claim 1, i) either by an aldehyde of general formula R$_3$CHO in which R$_3$ has the meaning indicated in claim 1, in the presence of an oxidizing agent;

ii) or by an acid chloride of general formula R$_3$COCl in which R$_3$ has the meaning indicated in claim 1, in the presence of an acid.

13. A method of treating a condition selected from the group consisting of obesity, anxiety, depression, neuropathic pain and erectile dysfunction in warm-blooded animals comprising administering to said warm-blooded animals in need thereof, an amount of a compound of claim 1 sufficient to treat said condition.

14. The method according to claim 13; wherein the condition is obesity.

15. The method according to claim 13, wherein the condition is anxiety or depression.

16. The method according to claim 13, wherein the condition is neuropathic pain.

17. The method according to claim 13, wherein condition is erectile dysfunction.

* * * * *